(12) United States Patent
Dull et al.

(10) Patent No.: US 10,556,880 B2
(45) Date of Patent: Feb. 11, 2020

(54) NICOTINE SALTS, CO-CRYSTALS, AND SALT CO-CRYSTAL COMPLEXES

(71) Applicant: R.J. Reynolds Tobacco Company, Winston-Salem, NC (US)

(72) Inventors: Gary M. Dull, Lewisville, NC (US); Andrew Carr, Cambridge (GB); Emma Sharp, Cambridgeshire (GB)

(73) Assignee: R.J. Reynolds Tobacco Company, Winston-Salem, NC (US)

(*) Notice: Subject to any disclaimer, the term of this patent is extended or adjusted under 35 U.S.C. 154(b) by 0 days.

(21) Appl. No.: 15/671,722

(22) Filed: Aug. 8, 2017

(65) Prior Publication Data

US 2017/0334881 A1 Nov. 23, 2017

Related U.S. Application Data

(63) Continuation of application No. 14/721,283, filed on May 26, 2015, now Pat. No. 9,738,622.

(60) Provisional application No. 62/003,295, filed on May 27, 2014.

(51) Int. Cl.
| | |
|---|---|
| *C07D 401/04* | (2006.01) |
| *C07C 65/03* | (2006.01) |
| *C07C 65/11* | (2006.01) |
| *A61K 9/00* | (2006.01) |
| *A24B 13/00* | (2006.01) |
| *A24B 15/38* | (2006.01) |
| *A24F 47/00* | (2006.01) |
| *A61M 15/06* | (2006.01) |
| *A61M 11/04* | (2006.01) |

(52) U.S. Cl.
CPC ............ *C07D 401/04* (2013.01); *A24B 13/00* (2013.01); *A24B 15/38* (2013.01); *A61K 9/0056* (2013.01); *C07C 65/03* (2013.01); *C07C 65/11* (2013.01); *A24F 47/008* (2013.01); *A61M 11/042* (2014.02); *A61M 15/06* (2013.01); *A61M 2205/8206* (2013.01); *C07B 2200/13* (2013.01)

(58) Field of Classification Search
CPC .................................................... C07D 401/04
USPC ....................................... 546/279.4; 514/343
See application file for complete search history.

(56) References Cited

U.S. PATENT DOCUMENTS

| | | |
|---|---|---|
| 2,033,909 A | 3/1936 | Cox et al. |
| 2,822,306 A | 2/1958 | Thienemann et al. |
| 4,153,063 A | 5/1979 | Roselius et al. |
| 4,830,028 A | 5/1989 | Lawson et al. |
| 4,967,771 A | 11/1990 | Fagg et al. |
| 5,031,646 A | 7/1991 | Lippiello et al. |
| 7,008,742 B2 | 3/2006 | Molaire |
| 7,452,555 B2 | 11/2008 | Childs |
| 7,650,891 B1 | 1/2010 | Groves et al. |
| 7,927,613 B2 | 4/2011 | Almarsson et al. |
| 7,935,817 B2 | 5/2011 | Blazecka et al. |
| 8,058,437 B2 | 11/2011 | Bauer et al. |
| 8,163,790 B2 | 4/2012 | Childs |
| 8,173,625 B2 | 5/2012 | Brittain et al. |
| 8,197,592 B2 | 6/2012 | Thompson et al. |
| 8,212,079 B2 | 7/2012 | Childs |
| 8,241,371 B2 | 8/2012 | Hanna et al. |
| 8,350,085 B2 | 1/2013 | Childs |
| 8,415,507 B2 | 4/2013 | Schultheiss et al. |
| 8,466,280 B2 | 6/2013 | Grunenberg et al. |
| 8,470,832 B2 | 6/2013 | George et al. |
| 8,513,236 B2 | 8/2013 | Schultheiss et al. |
| 8,999,405 B1 | 4/2015 | Bachman |
| 9,724,341 B2 | 8/2017 | Myers et al. |
| 2002/0048610 A1 | 4/2002 | Cima et al. |
| 2003/0224006 A1 | 12/2003 | Zaworotko et al. |
| 2006/0018840 A1 | 1/2006 | Lechuga-Ballesteros et al. |
| 2007/0287194 A1 | 12/2007 | Childs et al. |
| 2008/0280858 A1 | 11/2008 | Hanna et al. |
| 2008/0302377 A1 | 12/2008 | Nauryzbaev et al. |
| 2010/0204204 A1 | 8/2010 | Zaworotko et al. |
| 2011/0152266 A1 | 6/2011 | Grunenberg et al. |
| 2011/0174323 A1 | 7/2011 | Coleman, III et al. |
| 2011/0236478 A1 | 9/2011 | Dokou et al. |

(Continued)

FOREIGN PATENT DOCUMENTS

| | | |
|---|---|---|
| WO | WO 03/101454 | 12/2003 |
| WO | WO 2006/004646 | 1/2006 |

(Continued)

OTHER PUBLICATIONS

Halebian et al., Pharmaceutical Applications, etc., Pharmaceutical Sciences 58(8), 1969, 911-929.*

(Continued)

*Primary Examiner* — Patricia L Morris
(74) *Attorney, Agent, or Firm* — Womble Bond Dickinson (US) LLP

(57) ABSTRACT

The invention provides certain nicotine salts, co-crystals, and salt co-crystals and provides novel polymorphic forms of certain nicotine salts. In particular, nicotine salts with mucic acid, 3,5-dihydroxybenzoic acid, and 2,3-dihydroxybenzoic acid, and crystalline polymorphic forms of nicotine 4-acetamidobenzoate, nicotine gentisate, and nicotine 1-hydroxy-2-naphthoate are described. The invention further provides methods of preparation and characterization of such nicotine salts, co-crystals, and salt co-crystals and polymorphic forms thereof. In addition, tobacco products, including smoking articles, smokeless tobacco products, and electronic smoking articles comprising nicotine salts, co-crystals, and/or salt co-crystals are also provided.

14 Claims, 23 Drawing Sheets

(56) References Cited

U.S. PATENT DOCUMENTS

| | | |
|---|---|---|
| 2011/0251426 A1 | 10/2011 | Childs et al. |
| 2011/0257430 A1 | 10/2011 | Childs |
| 2011/0259353 A1 | 10/2011 | Coleman, III et al. |
| 2011/0268809 A1 | 11/2011 | Brinkley et al. |
| 2012/0022117 A1 | 1/2012 | Gruss et al. |
| 2012/0028930 A1 | 2/2012 | Kalofonos et al. |
| 2012/0028998 A1 | 2/2012 | Sansone et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. et al. |
| 2012/0258170 A1 | 10/2012 | Kruthiventi et al. |
| 2013/0040970 A1 | 2/2013 | Cosgrove et al. |
| 2013/0072440 A1 | 3/2013 | Dokou et al. |
| 2013/0078307 A1 | 3/2013 | Holton, Jr. et al. |
| 2013/0203806 A1 | 8/2013 | Chorlton et al. |
| 2013/0274296 A1 | 10/2013 | Jackson et al. |
| 2014/0000638 A1 | 1/2014 | Sebastian et al. |
| 2014/0088044 A1 | 3/2014 | Rigas et al. |
| 2016/0185750 A1 | 6/2016 | Dull et al. |
| 2018/0051002 A1 | 2/2018 | Dull et al. |

FOREIGN PATENT DOCUMENTS

| | | |
|---|---|---|
| WO | WO 2006/053082 | 5/2006 |
| WO | WO 2010/044736 | 4/2010 |
| WO | WO 2011/017533 | 2/2011 |
| WO | WO 2013/158643 | 10/2013 |
| WO | WO 2014/006604 | 9/2014 |
| WO | WO 2014/182736 | 11/2014 |
| WO | WO 2015/166350 | 11/2015 |
| WO | WO 2015/183801 | 12/2015 |
| WO | WO 2016/071705 | 5/2016 |
| WO | WO 2016/071706 | 5/2016 |
| WO | WO 2017/051181 | 3/2017 |
| WO | WO 2017/055866 | 4/2017 |
| WO | WO 2017/089931 | 6/2017 |

OTHER PUBLICATIONS

Dean "Analytical Chem . . . " p. 10.24-10.26 (1995).*
Seddon "Pseudopolymorph . . . " Crystal Growth & design v.4(6) p. 1087 (2004) (2 pages from internet).*
Ivanisevic et al., "Use of X-ray . . . " Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare:NY 2009 p. 318-335.*
Aakeroy, "Crystal Engineering, etc.," Acta Cryst. (1997) B53, 569-586.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Stahly, "Diversity in Single-, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Weyna et al., "Synthesis and Structural, etc.," Crystal Growth & Design, 2009, 9(2), 1106-1123.*
www.jce.divched.org "Nicotine Volatilization in Tobacco Matrix," *Journal of Chemical Education*, 2005, vol. 82, No. 10, pp. 1577-1578.
http://www.fda.gov/Drugs/GuidanceComplianceRegulatoryInformation/Guidance/default.htm; "Gudiance for Industry, Regulatory Classification of Pharmaceutical Co-Crystals," U.S. Department of Health and Human Services, Food and Drug Administration, Center for Drug Evaluation and Research, (CDER), Apr. 2013, pp. 1-5.
Challener, "API Synthesis & Manufacturing: Scientific Advances in Cocrystals are Offset by Regulatory Uncertainty," *Pharmaceutical Technology*, May 2014, pp. 42-45. www.PharmTech.com.
Dezelic et al. "Nicotine Compounds with Aromatic Acids," *Kem. Vjestnik*, 17, 1943, 39-57.
Dezelic et al., "Nicotine Compounds with Aromatic Acids. Part II," *Glasnik Drustva Hemicara Technol. NR Bosne Hercegovine*, 1961, vol. 10, pp. 55-62.
Dezelic et al., "Determination of the Composition and the Molecualar Weights of Some Salts of Heterocyclic Bases from the UV Spectra" *Glasnik Hemicara i Tehnologa BiH, Sarajevo*, 1964-1965, 13-14, 27-36.
Dezelic et al., "Determination of Structure of Some Salts of Nicotine, pyridine and N-Methylpyrrolidine on the Basis of Their Infra-Red Spectra," *Spectrochimica Acta, Part A: Molecular and Biomolecular Spectroscopy* (1967), 23(A), 1149-53.
Kim et al., "The Crystal Structure of a 1:1 Nicotine-Salicylic Acid Complex (Nicotinyl Salicylate)," *Acta Cryst.*, 1971, B27, pp. 1123-1131.
Lasslo et al., "Salts of p-Acetamidobenzoic Acid," *J. Amer. Pharm. Assoc.* (1912-1977), 1959, 48, 345-7.
Nikolin et al., "Structure of Some Nicotine Salts and Their Fungicidal Action," *Glasnik Hemicara i Tehnologa BiH, Sarajevo*, 18, (1970) pp. 17-24.
Perfetti, "Structural Study of Nicotine Salts," *Beitrage Tabakforschung Int.*, vol. 12, No. 2, 43-54 (1983).
Perfetti, "The Transfer of Nicotine from Nicotine Salts to Mainstream Smoke," *Beitrage Tabakforschung Int.,Contributions to Tobacco Research*, vol. 19, No. 3, 2000, pp. 141-158.
Seeman et al., "The Form of Nicotine in Tobacco. Thermal Transfer of Nicotine and Nicotine Acid Salts to Nicotine in the Gas Phase," *J. Agric. Food Chem.* 1999, vol. 47, pp. 5133-5145.
Bernstein, "Polymorphism in Molecular Crystals," pp. 115-118, 272, (2002).

* cited by examiner

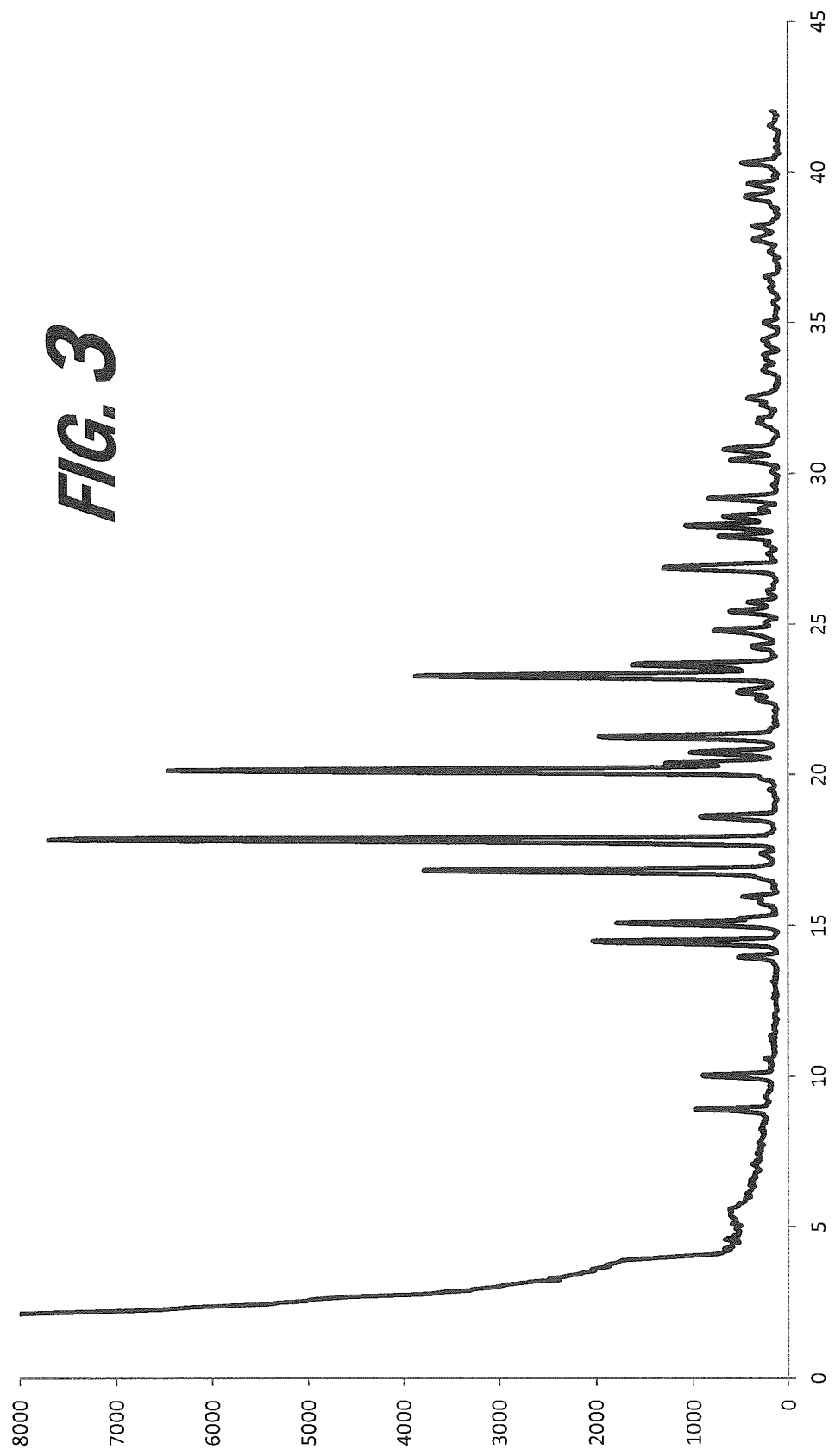

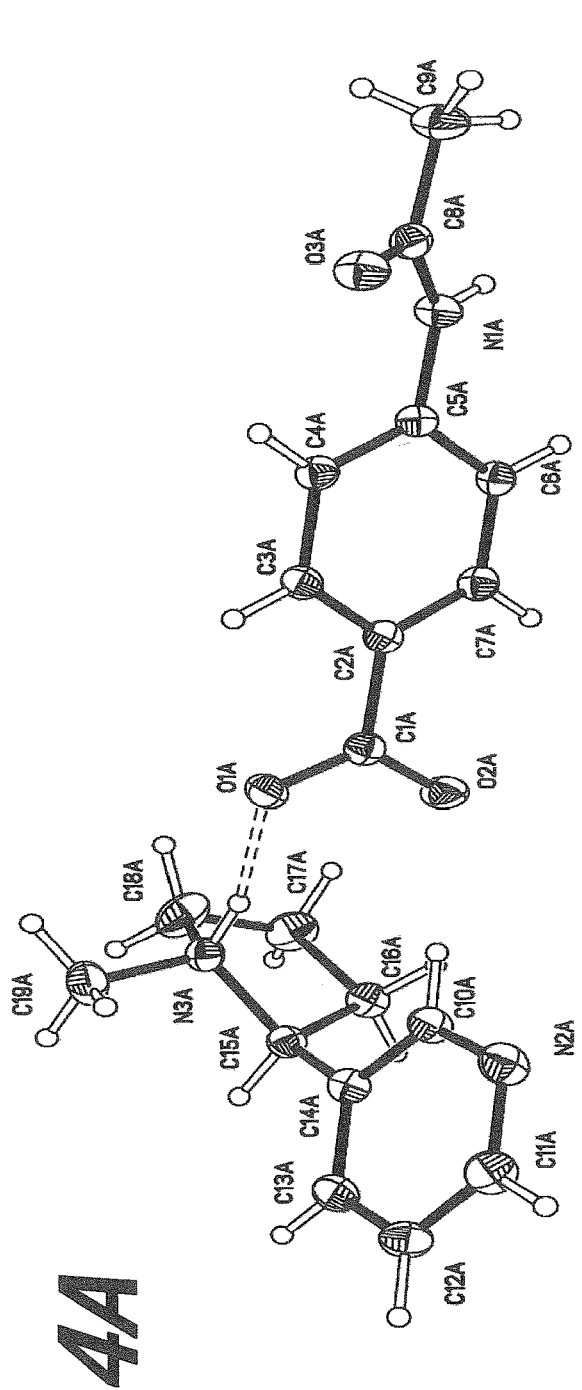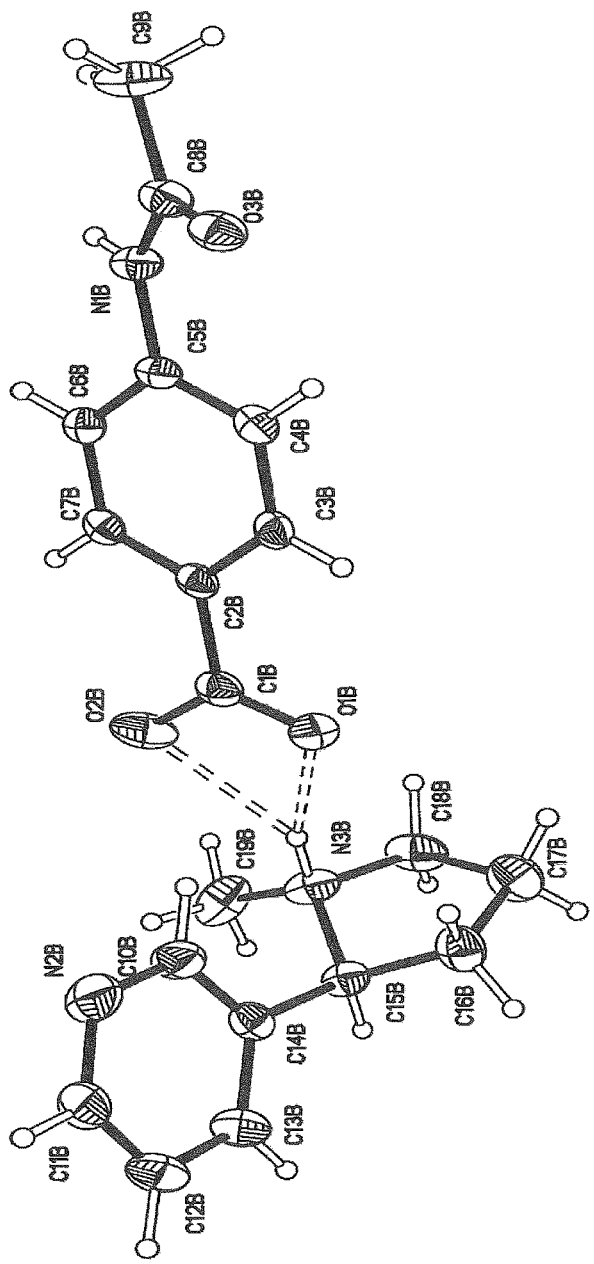
FIG. 4A
FIG. 4B

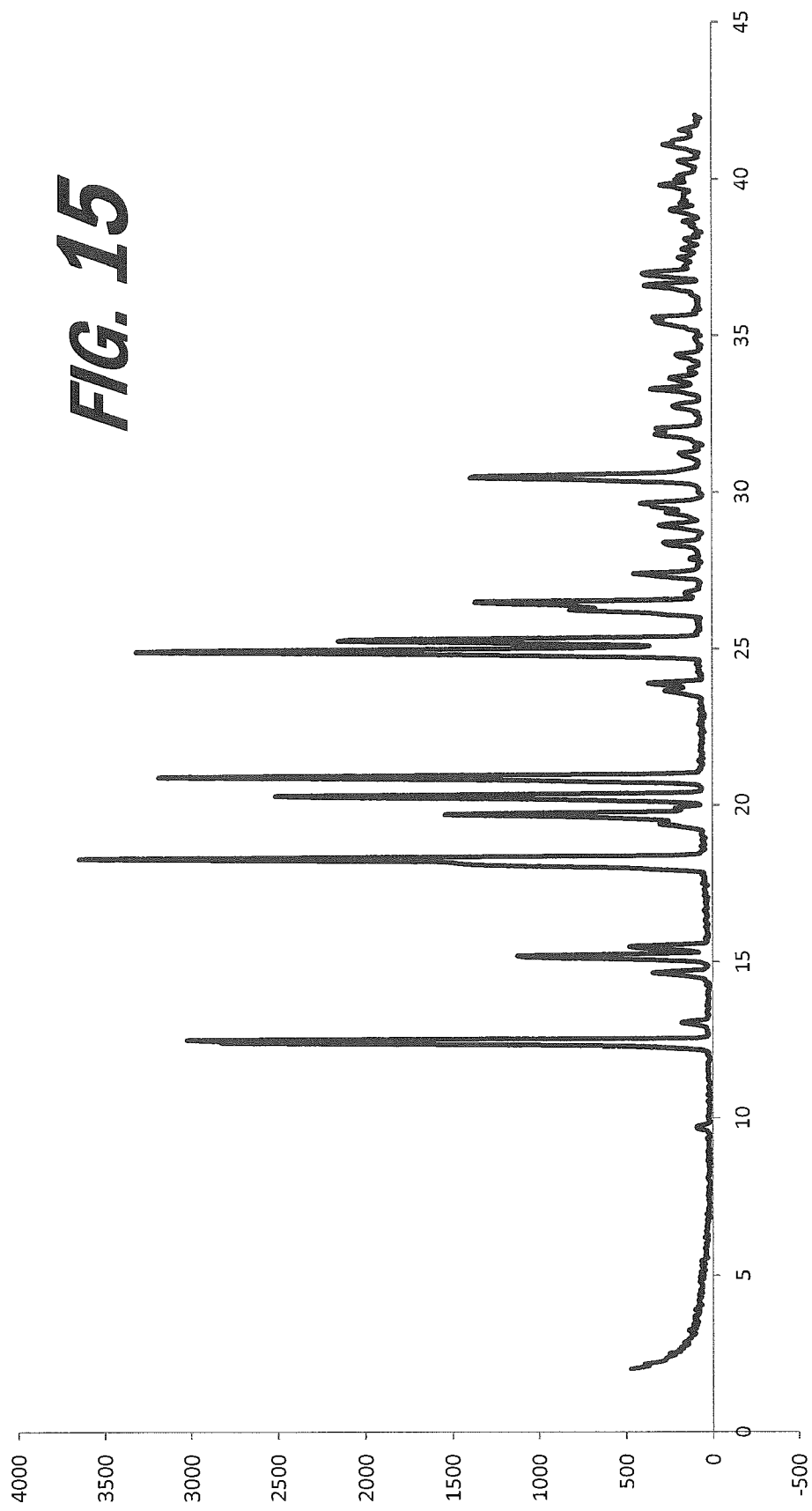

NICOTINE SALTS, CO-CRYSTALS, AND SALT CO-CRYSTAL COMPLEXES

CROSS-REFERENCE TO RELATED APPLICATIONS

The present application is a continuation of U.S. patent application Ser. No. 14/721,283, filed May 26, 2015, which claims priority to U.S. Provisional Application No. 62/003,295, filed May 27, 2014, which are incorporated by reference herein in their entireties.

FIELD OF THE INVENTION

The present invention relates to various salts, co-crystals, and salt co-crystals of nicotine and to compositions and products (e.g., tobacco products) into which such salts, co-crystals, and salt co-crystals can be incorporated.

BACKGROUND OF THE INVENTION

Cigarettes, cigars and pipes are popular smoking articles that employ tobacco in various forms. Such smoking articles are used by heating or burning tobacco, and aerosol (e.g., smoke) is inhaled by the smoker. Electronic smoking articles are a further type of tobacco product, which comprise a reservoir and heating system for the delivery of aerosolizable materials. Tobacco also may be enjoyed in a so-called "smokeless" form. Particularly popular smokeless tobacco products are employed by inserting some form of processed tobacco or tobacco-containing formulation into the mouth of the user.

Various types of cigarette components, including tobacco types, tobacco blends, top dressing and casing materials, blend packing densities and types of paper wrapping materials for tobacco rods, are set forth in the art. See, for example, the various representative types of cigarette components, as well as the various cigarette designs, formats, configurations and characteristics, that are set forth in Johnson, Development of Cigarette Components to Meet Industry Needs, $52^{nd}$ T.S.R.C. (September 1998); U.S. Pat. No. 5,101,839 to Jakob et al.; U.S. Pat. No. 5,159,944 to Arzonico et al.; U.S. Pat. No. 5,220,930 to Gentry and U.S. Pat. No. 6,779,530 to Kraker; U.S. Pat. App. Pub. Nos. 2005/0016556 to Ashcraft et al.; 2005/0066986 to Nestor et al.; 2005/0076929 to Fitzgerald et al.; 2006/0272655 to Thomas et al.; 2007/0056600 to Coleman, III et al.; and 2007/0246055 to Oglesby, each of which is incorporated herein by reference.

Exemplary smokeless tobacco formulations, ingredients, and processing methodologies are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; U.S. Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al. and 2011/0139164 to Mua et al.; PCT WO 04/095959 to Arnarp et al. and WO 2010/132444 A2 to Atchley; each of which is incorporated herein by reference. Exemplary smokeless tobacco products that have been marketed include those referred to as CAMEL Snus, CAMEL Orbs, CAMEL Strips and CAMEL Sticks by R. J. Reynolds Tobacco Company; GRIZZLY moist tobacco, KODIAK moist tobacco, LEVI GARRETT loose tobacco and TAYLOR'S PRIDE loose tobacco by American Snuff Company, LLC; KAYAK moist snuff and CHATTANOOGA CHEW chewing tobacco by Swisher International, Inc.; REDMAN chewing tobacco by Pinkerton Tobacco Co. LP; COPENHAGEN moist tobacco, COPENHAGEN Pouches, SKOAL Bandits, SKOAL Pouches, RED SEAL long cut and REVEL Mint Tobacco Packs by U.S. Smokeless Tobacco Company; and MARLBORO Snus and Taboka by Philip Morris USA.

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. Pub. No. 2013/0255702 to Griffith Jr. et al., U.S. Pat. Pub. Nos. 2014/0000638 to Sebastian et al., 2014/0060554 to Collett et al., 2014/0060555 to Chang et al., 2014/0096781 to Sears et al., 2014/0096782 to Ampolini et al., and 2015/0059780 to Davis et al., which are incorporated herein by reference in their entireties.

Certain of these types of smoking articles, smokeless tobacco products, and electronic smoking articles comprise a tobacco extract, which in some products may be purified such that the extract is comprised primarily of nicotine. However, tobacco extracts comprising a high percentage of nicotine (including extracts comprising at least about 90%, at least about 95%, and at least about 99% nicotine by weight) are typically in oil form. As such, nicotine extracts can be difficult to handle and incorporate into certain tobacco products.

It would be desirable to provide such nicotine-based extracts in a form that is amenable to incorporation in tobacco products. It would further be desirable to incorporate such extracts into an enjoyable form of a tobacco product and to provide processes for preparing such forms of nicotine-based extracts as well as for preparing various types of compositions and products incorporating such forms of nicotine-based extracts.

SUMMARY OF THE INVENTION

The present invention provides various forms of nicotine that can be applicable to a wide range of products, including tobacco products. Particularly, the present application describes nicotine salts, co-crystals, and salt co-crystals and the preparation of such nicotine salts, co-crystals, and salt co-crystals. It also describes the incorporation of such nicotine salts, co-crystals, and/or salt co-crystals into various products including tobacco products (e.g., smoking articles, smokeless tobacco products, and electronic smoking articles) and pharmaceutical products.

In a first aspect of the invention is provided a nicotine salt or crystalline polymorphic form selected from the group consisting of: a salt of nicotine and mucic acid; a salt of nicotine and 3,5-dihydroxybenzoic acid; a salt of nicotine and 2,3-dihydroxybenzoic acid; a crystalline polymorphic form of nicotine 1-hydroxy-2-naphthoate, wherein the form is characterized by an X-ray powder diffraction pattern having peaks at one or more (including all) of the following 2-theta diffraction angles: 15.6, 16.1, 20.5, 22.5, and 27.1; a crystalline polymorphic form of nicotine 4-acetamidobenzoate, wherein the form is characterized by an X-ray powder diffraction pattern having peaks at one or more (including all) of the following 2-theta diffraction angles: 16.839, 17.854, 20.134, and 23.265; and a crystalline polymorphic form of nicotine gentisate, wherein the form is characterized by an X-ray powder diffraction pattern having peaks at one or more (including all) of the following 2-theta diffraction angles: 13.000, 19.017, 20.194, and 21.000. A given percentage of the material, e.g., at least about 50% of the material, can be in crystalline form.

In one embodiment, a salt formed from nicotine and mucic acid, characterized by an X-ray powder diffraction pattern having peaks at one or more of the following 2-theta diffraction angles: 14.289, 15.449, 19.66, and 20.412 is provided. In an additional embodiment, a salt formed from nicotine and 2,3-dihydroxybenzoic acid is provided, wherein the form is characterized by an X-ray powder diffraction pattern having peaks at one or more of the following 2-theta diffraction angles: 12.4, 12.5, 15.2, 18.3, 19.7, 20.3, 20.9, 24.9, 25.2, 26.5, and 30.4.

In another embodiment, a salt formed from nicotine and 3,5-dihydroxybenzoic acid is provided, wherein the form is an anhydrous form characterized by an X-ray powder diffraction pattern having peaks at one or more of the following 2-theta diffraction angles: 12.7, 17.8, 19.7, 20.2, 21.3, 24.5, 24.9, 25.8, and 29.8. In a further embodiment, a salt formed from nicotine and 3,5-dihydroxybenzoic acid is provided, wherein the form is a hydrated form characterized by an X-ray powder diffraction pattern having peaks at one or more of the following 2-theta diffraction angles: 10.7, 13.4, 15.0, 17.2, 17.3, 19.0, 21.4, 21.6, 22.2, 22.6, 22.9, 24.3, 25.1, 25.5, and 29.7. A given sample of salt formed from nicotine and 3,5-dihydroxybenzoic acid can comprise completely and/or substantially one single form, or can comprise a mixture of two or more forms (including, but not limited to, the anhydrous and dihydrate forms referenced above) in varying amounts.

The nicotine salts, co-crystals, and salt co-crystals described in the present application are generally applicable for use in a range of products including, but not limited to, smoking articles, electronic smoking articles, smokeless tobacco products (e.g., lozenges and gums), pharmaceutical products, and the like. Accordingly, in another aspect of the invention is provided a product incorporating one or more nicotine salts, co-crystals, and/or salt co-crystals as described herein. In various embodiments, electronic smoking articles, smokeless tobacco products, and/or pharmaceutical products incorporating one or more of the salts, co-crystals, and/or salt co-crystal complexes disclosed herein are provided.

For example, in one aspect, the disclosure provides an electronic smoking article comprising an inhalable substance medium contained within a cartridge body and a heating member positioned to provide heat to at least a portion of the inhalable substance medium, wherein the inhalable substance medium comprises a nicotine salt or crystalline polymorphic form as disclosed herein (e.g., one or more salts or crystalline polymorphic forms selected from the group consisting of: a salt of nicotine and mucic acid; a salt of nicotine and 3,5-dihydroxybenzoic acid; a salt of nicotine and 2,3-dihydroxybenzoic acid; a crystalline polymorphic form of nicotine 1-hydroxy-2-naphthoate, wherein the form is characterized by an X-ray powder diffraction pattern having peaks at one or more (including all) of the following 2-theta diffraction angles: 15.6, 16.1, 20.5, 22.5, and 27.1; a crystalline polymorphic form of nicotine 4-acetamidobenzoate, wherein the form is characterized by an X-ray powder diffraction pattern having peaks at one or more (including all) of the following 2-theta diffraction angles: 16.839, 17.854, 20.134, and 23.265; and a crystalline polymorphic form of nicotine gentisate, wherein the form is characterized by an X-ray powder diffraction pattern having peaks at one or more (including all) of the following 2-theta diffraction angles: 13.000, 19.017, 20.194, and 21.000).

The inhalable substance medium can further comprise, for example, one or more of glycerin, water, and a flavorant. The amount of nicotine salt or polymorph form incorporated can vary and, in some embodiments, can be that amount sufficient to provide nicotine in an amount of about 0.01 mg to about 0.5 mg, about 0.05 mg to about 0.3 mg, or about 0.1 mg to about 0.2 mg per puff on the article.

In another aspect, the disclosure provides a smokeless tobacco product comprising a nicotine salt or crystalline polymorphic form as described herein (e.g., one or more salts or crystalline polymorphic forms selected from the group consisting of: a salt of nicotine and mucic acid; a salt of nicotine and 3,5-dihydroxybenzoic acid; a salt of nicotine and 2,3-dihydroxybenzoic acid a crystalline polymorphic form of nicotine 1-hydroxy-2-naphthoate, wherein the form is characterized by an X-ray powder diffraction pattern having peaks at one or more (including all) of the following 2-theta diffraction angles: 15.6, 16.1, 20.5, 22.5, and 27.1; a crystalline polymorphic form of nicotine 4-acetamidobenzoate, wherein the form is characterized by an X-ray powder diffraction pattern having peaks at one or more (including all) of the following 2-theta diffraction angles: 16.839, 17.854, 20.134, and 23.265; and a crystalline polymorphic form of nicotine gentisate, wherein the form is characterized by an X-ray powder diffraction pattern having peaks at one or more (including all) of the following 2-theta diffraction angles: 13.000, 19.017, 20.194, and 21.000). Exemplary smokeless tobacco products include, but are not limited to, loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; and capsule-like materials possessing an outer shell and an inner region.

In a further aspect, the disclosure provides a pharmaceutical product comprising a nicotine salt or crystalline polymorphic form as described herein (e.g., one or more salts or crystalline polymorphic forms selected from the group consisting of: a salt of nicotine and mucic acid; a salt of nicotine and 3,5-dihydroxybenzoic acid; a salt of nicotine and 2,3-dihydroxybenzoic acid; a salt of nicotine and 1-hydroxy-2- naphthoic acid; a crystalline polymorphic form of nicotine 4-acetamidobenzoate, wherein the form is characterized by an X-ray powder diffraction pattern having peaks at one or more of the following 2-theta diffraction angles: 16.839, 17.854, 20.134, and 23.265; and a crystalline polymorphic form of nicotine gentisate, wherein the form is characterized by an X-ray powder diffraction pattern having peaks at one or more of the following 2-theta diffraction angles: 13.000, 19.017, 20.194, and 21.000). Such products can be, for example, in a form selected from the group consisting of a pill, tablet, lozenge, capsule, caplet, pouch, gum, inhaler, solution, and cream. One exemplary lozenge formulation comprises one or more of the nicotine salts or crystalline polymorphic forms disclosed herein and at least about 50% by weight isomalt.

Additionally, in a still further aspect, the disclosure provides methods of preparing certain nicotine salts and crystalline polymorphic forms. For example, the disclosure provides methods of preparing nicotine mucate, comprising combining mucic acid and nicotine to form a solid and isolating the solid. The disclosure provides methods of preparing nicotine 3,5-dihydroxybenzoate, comprising combining 3,5-dihydroxybenzoic acid and nicotine to form a solid and isolating the solid. In some embodiments, the resulting salt can comprise an anhydrous form. A hydrated form (e.g., a dihydrate form) can, in certain embodiments, be prepared by exposing the anhydrous form to humidity as disclosed herein. The disclosure provides methods of preparing nicotine 2,3-dihydroxybenzoate, comprising combining 2,3-dihydroxybenzoic acid and nicotine to form a solid and isolating the solid.

The disclosure also provides methods of preparing a crystalline polymorphic form of nicotine 1-hydroxy-2-naphthoate, comprising combining 1-hydroxy-2-naphthoic acid and nicotine to form a solid and isolating the solid. The disclosure further provides a method of preparing a crystalline polymorphic form of nicotine 4-acetamidobenzoate, comprising combining 4-acetamidobenzoic acid and nicotine in equimolar amounts in a solvent (e.g., tetrahydrofuran) to form a solid and isolating the solid. The disclosure also provides a method of preparing a crystalline polymorphic form of nicotine gentisate, comprising combining gentisic acid and nicotine in equimolar amounts in a solvent (e.g., tetrahydrofuran) to form a solid and isolating the solid.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

FIG. 3 is an x-ray powder diffraction pattern of crystalline nicotine 4-acetamidobenzoate, showing the experimental pattern and the pattern calculated from the single crystal x-ray structure;

FIGS. 4A and 4B are views of crystal structures obtained for two independent molecules of nicotine 4-acetamidobenzoate and FIG. 4C is a view of the crystal packing of nicotine 4-acetamidobenzoate;

FIG. 15 is an x-ray powder diffraction pattern of nicotine 2,3-dihydroxybenzoate;

DETAILED DESCRIPTION OF THE PREFERRED EMBODIMENTS

Figure 1:
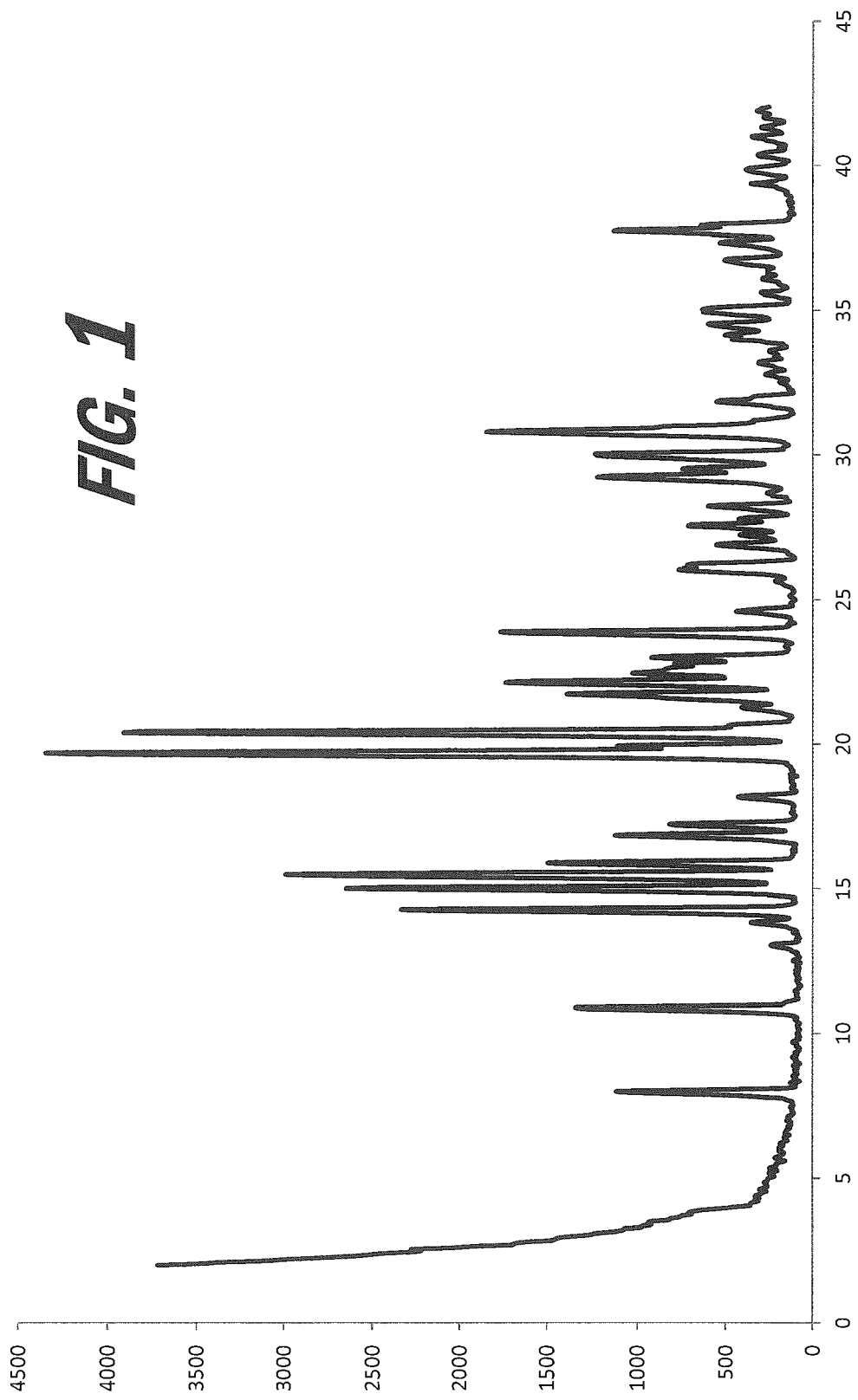
FIG. 1 is an x-ray powder diffraction pattern of nicotine mucate.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention relates to nicotine salts, co-crystals, and salt co-crystals and methods of preparation thereof. It also relates to products (including tobacco products and pharmaceutical products) that comprise one or more nicotine salts, co-crystals, and/or salt co-crystals. In certain embodiments, nicotine provided in one or more such forms can advantageously be isolated in a physical form that is an improvement over neat nicotine, which is a hygroscopic, oily liquid. For example, in certain embodiments, nicotine salts, co-crystals, and/or salt co-crystals as described herein can be in an easier to handle form than neat nicotine (e.g., a solid or semi-solid form), can be provided in a higher purity form than neat nicotine, and/or can exhibit greater thermodynamic, physical, and/or chemical stability (e.g., a higher resistance to oxidation, reduced risk of hydrate formation, and/or a longer shelf life) than neat nicotine. In some embodiments, nicotine salts, co-crystals, and/or salt co-crystals can provide increased stability in the presence of relevant excipients in the product into which the salt, co-crystal, and/or salt co-crystal will be incorporated, as compared to neat nicotine. In some embodiments, nicotine salts, co-crystals, and salt co-crystals can exhibit a significant degree of water-solubility, rendering them applicable for incorporation within a wide range of compositions and products.

Nicotine itself can be isolated and/or treated such that it is in one of two enantiomeric forms or it may be provided in racemic form. Nicotine is naturally occurring in levorotatory, (L)-nicotine form (also known as (−)-nicotine or S-nicotine). In the salts, co-crystals, and salt co-crystals provided herein, the nicotine is generally in the form of (L)-nicotine, although this disclosure is not intended to preclude the preparation and application of dextrorotatory ((D)-nicotine) salts, co-crystals, and salt co-crystals or racemic forms of nicotine in the disclosed salts, co-crystals, and salt co-crystals. Accordingly, nicotine salts, co-crystals, and salt co-crystals can be in an enantiomerically highly pure form (i.e., (L)- or (D)-form) or in racemic form as described herein.

A "nicotine salt" is a form of nicotine characterized by the interaction between nicotine in ionic form and a coformer in ionic form (e.g., an acid) via the transfer of one or more protons from the coformer donor to the nicotine acceptor. The structure of nicotine is such that it comprises two nitrogen atoms that are capable of accepting protons from a coformer and, accordingly, it can be present in non-protonated, mono-protonated, and/or di-protonated form in a given sample.

Certain nicotine salts are presently known. For example, nicotine sulfate has been sold as a pesticide and nicotine bitartrate dihydrate (also known as nicotine hydrogen tartrate) is a commercially available, water-soluble nicotine salt. Various other salts have been studied, including a nicotine acetic acid salt (which forms a viscous oil) as well as, for example, nicotine citrates and nicotine malates. See, for example, the types of ingredients and techniques set forth in U.S. Pat. No. 2,033,909 to Cox et al. and Perfetti, *Beitrage Tabakforschung Int.*, 12, 43-54 (1983). Additionally, certain salts of nicotine have been available from sources such as Pfaltz and Bauer, Inc. and K&K Laboratories, Division of ICN Biochemicals, Inc. Exemplary known nicotine salts include nicotine salts such as nicotine tartrate and nicotine bitartrate, nicotine chloride (e.g., nicotine hydrochloride and nicotine dihydrochloride), nicotine sulfate, nicotine perchlorate, nicotine ascorbate, nicotine fumarate, nicotine citrate, nicotine malate, nicotine lactate, nicotine aspartate, nicotine salicylate, nicotine tosylate, nicotine succinate, nicotine pyruvate, and nicotine salt hydrates (e.g., nicotine zinc chloride monohydrate). A nicotine salt with levulinic acid is discussed in U.S. Pat. App. Pub. No. 2011/0268809 and Int. App. Pub. No. PCT/U.S.2011/033928, both to Brinkley et al., which are incorporated herein by reference. See also, for example, U.S. Pat. No. 4,830,028 to Lawson et al. and U.S. Pat. No. 5,031,646 to Lippiello et al. and Leonard, Ind. Eng. Chem. 48: 1331-1341 (1956). However, certain previously disclosed nicotine salts of organic acids are not commonly crystalline and can exhibit a range of stoichiometries, which may make them unsuitable for use in certain applications.

A "nicotine co-crystal" is a form of nicotine comprising nicotine and at least one other component ("coformer"), both in neutral form. Co-crystals are typically characterized by a crystalline structure, which is generally held together by freely reversible, non-covalent interactions. Co-crystals are typically made up of nicotine and at least one other component in a defined stoichiometric ratio. In some embodiments, co-crystals can encompass hydrates, solvates, and clathrates. Co-crystals can comprise nicotine in combination with an organic and/or an inorganic component. Co-crystals can generally be distinguished from salts by the absence of a proton transfer between the components (i.e., the nicotine and the one or more coformers) in a co-crystal. According to the U.S. Food and Drug Administration's Guidance for Industry (April 2013), a co-crystal is defined as a solid that is a crystalline material composed of two or more molecules in the same crystal lattice, where the components are in a neutral state and interact via nonionic interactions. See U.S. Department of Health and Human Services, Food and Drug Administration, Guidance for Industry: Regulatory Classification of Pharmaceutical Co-Crystals (April 2013), which is incorporated herein by reference.

A "nicotine salt co-crystal" is a type of hybrid structure with both salt and co-crystal characteristics. Typically, a nicotine molecule within a salt co-crystal is associated with at least two coformers (which may be the same or different), wherein one coformer is in ionic form (e.g., an acid) and transfers a proton to the nicotine molecule and wherein a second coformer does not transfer a proton to the nicotine molecule.

The stoichiometry of the salts, co-crystals, and salt co-crystals described herein can vary. For example, in certain embodiments, where two components (i.e., nicotine and one coformer) are present, the nicotine: coformer stoichiometry can range in certain embodiments from about 5:1 to about 1:5 nicotine: coformer. Where more than one coformer is used to form a nicotine salt, co-crystal, or salt co-crystal, the ratios of the coformers with respect to both the nicotine and to one another can also vary. In preferable embodiments, a given sample of the salts, co-crystals, and salt co-crystals provided according to the present disclosure exhibit substantially one single stoichiometry.

The salts, co-crystals, and salt co-crystals described herein can, in some embodiments, exist in various polymorphic and pseudopolymorphic forms. Polymorphism is the ability of a crystalline material to exist in more than one form or crystal structure. Polymorphism can result, e.g., from the existence of different crystal packing structures (packing polymorphism) or from the existence of different conformers of the same molecule (conformational polymorphism). Pseudopolymorphism is the result of hydration or solvation of a material and is also referred to as solvomorphism.

The salts, co-crystals, and salt co-crystals of the present disclosure can incorporate nicotine derived from some form of a plant of the *Nicotiana* species (e.g., some form of tobacco). The nicotine can be, for example, in the form of a highly purified tobacco extract. Various methods are known for the isolation and purification of nicotine from tobacco (including, but not limited to, extraction from tobacco with water; extraction from tobacco with organic solvents; steam distillation from tobacco; or pyrolytic degradation of tobacco and distillation of nicotine therefrom). For exemplary extraction methods, see for example, U.S. Pat. Nos.

2,822,306 and 4,153,063 to Roselius et al. and U.S. Pat. App. Pub. No. 2008/0302377 to Kauryzbaev et al., which are incorporated herein by reference.

The selection of the plant from the *Nicotiana* species (from which such extracts and other tobacco materials that can be combined with the salts, co-crystals, and/or salt co-crystals described herein are obtained) can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). Additional information on types of *Nicotiana* species suitable for use in the present invention can be found in U.S. Pat. App. Pub. No. 2012/0192880 to Dube et al., which is incorporated by reference herein. Tobacco plants can be grown in greenhouses, growth chambers, or outdoors in fields, or grown hydroponically.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *Nicotiana* species. See, for example, the portions of tobacco plants set forth in U.S. Pat. App. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green form or a cured form, as described in 2012/0192880 to Dube et al., which is incorporated by reference herein. The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. Exemplary processing techniques are described, for example, in U.S. Pat. App. Pub. Nos. 2009/0025739 to Brinkley et al. and 2011/0174323 to Coleman, III et al., which are incorporated by reference herein. At least a portion of the plant of the *Nicotiana* species can be treated with enzymes and/or probiotics before or after harvest, as discussed in U.S. Pat. App. Pub. Nos. 2013/0269719 to Marshall et al. and 2014/0020694 to Moldoveanu, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant. As such, harvested portion or portions of the plant can be used as such as components of tobacco products, or processed further.

To provide a nicotine extract, the plant of the *Nicotiana* species or portions thereof is typically subjected to one or more types of processing conditions. Typical separation processes can include one or more process steps (e.g., solvent extraction using polar solvents, organic solvents, and/or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), halogenated hydrocarbons (e.g., monofluorotrichloromethane (Freon 11), dichlorotrifluoroethane (Freon 123), and the like), diethyl ether, methylene chloride, and supercritical carbon dioxide. See, for example, the description of isolated tobacco components and techniques for isolation in U.S. Pat. No. 4,967,771 to Fagg et al., U.S. Pat. App. Pub. Nos. 2011/0174323 to Coleman, III et al.; 2011/0259353 to Coleman, III et al.; 2012/0192880 to Dube et al.; 2012/0192882 to Dube et al.; and 2012/0211016 to Byrd, Jr. et al., which are incorporated by reference herein.

Although the nicotine incorporated within the salts, co-crystals, and salt co-crystals of the present disclosure are commonly derived from some form of a plant of the *Nicotiana* species as outlined above, the source of the nicotine is not limited thereto. For example, in some embodiments, nicotine may be provided synthetically. In some embodiments, nicotine may be obtained from another source (e.g., another type of plant).

Nicotine is typically isolated (e.g., as described above) in neat (liquid) form. According to the present invention, nicotine is modified such that it is provided in other forms by incorporating the nicotine as a component of a salt, co-crystal, or salt co-crystal, e.g., in the form of an oil, solid, semi-solid, etc. In some embodiments, certain salts, co-crystals, and salt co-crystals are desirably provided in solid form, e.g., solid, crystalline form. Advantageously (although not necessarily), coformers (including acids) that are combined with nicotine to form such nicotine salts, co-crystals, or salt co-crystals are "GRAS" (Generally Regarded As Safe) according to the U.S. Food and Drug Administration. Furthermore, it is beneficial (although again, not necessary) for the nicotine salts, co-crystals, and/or salt co-crystals produced thereby to also be GRAS.

In one embodiment, nicotine mucate (also called nicotine galactarate) is provided. Nicotine mucate is formed from nicotine and mucic acid (also known as (2S,3R,4S,5R)-2,3,4,5-tetrahydroxyhexanedioic acid, hexaric acid, galactaric acid, meso-galactaric acid, saccharolactic acid, tetrahydroxyadipic acid, tetrahydroxyhexanedioic acid). In one aspect, a nicotine mucate salt is provided having a stoichiometry of from about 2:1 nicotine:acid to about 1:2 nicotine to acid. In certain embodiments, a nicotine mucate salt is provided having a stoichiometry of between about 2:1 nicotine:acid and about 1:1 nicotine:acid (i.e., having no more than 1 equivalent of acid per nicotine).

It is noted that, in some embodiments, the exact form of nicotine mucate prepared according to the present disclosure may not be known. As described in Example 1, in one embodiment, nicotine mucate was prepared and analyzed by $^1$H NMR, which indicated that the solid consisted of 0.72 equivalents of acid. Although not intending to be limited, this determination may be consistent with a nicotine mucate salt co-crystal, e.g., having a hemi mucate salt structure with additional mucic acid molecules associated therewith (by hydrogen bonding). However, it is possible that the nicotine mucate prepared and reported herein is, in fact, a hemi mucate salt (i.e., consisting of 0.5 equivalents of acid).

In certain embodiments, nicotine mucate is provided in solid form and may be in crystalline and/or amorphous form. An exemplary x-ray powder diffraction (XRPD) pattern of a sample comprising crystalline and amorphous forms of nicotine mucate is provided in FIG. 1. The nicotine mucate can be described as exhibiting an XRPD pattern having peaks at one or more of the following 2-theta diffraction angles: 14.289°, 15.449°, 19.66°, and 20.412°. Full characterization data, including a table of all relevant peaks in the x-ray diffraction pattern, is provided in Example 1. A $^1$H NMR spectrum of this material is provided in FIG. 2.

Advantageously, in certain embodiments, a sample of nicotine mucate is provided wherein at least a particular percentage comprises the form described herein. For example, in some embodiments, nicotine mucate comprising at least about 70%, at least about 75%, at least about 80%, at least about 85%, at least about 90%, at least about 95%, at least about 97%, at least about 98%, or at least about 99% of the form described herein by weight is provided Consistent with a crystalline form, nicotine mucate may, in some embodiments, exhibit a relatively sharp melting point. For example, in certain embodiments, nicotine mucate can exhibit a discrete melting point with an onset between about 120° C. and about 125° C. (e.g., about 123° C.). Consistent with an amorphous form, nicotine mucate may, in certain embodiments, lack a discrete melting point. Amorphous nicotine mucate may exhibit a broad melting range. In certain embodiments, nicotine mucate can exhibit a melting range with an onset of about 133° C. Samples that exist as a mixture of amorphous and crystalline nicotine mucate may exhibit both a relatively sharp melting point and a broad melting range. The ratio of crystalline to amorphous nicotine mucate can vary and may be, for example, between about 10:90 and about 90:10.

In certain embodiments, polarized light microscopy (PLM) of nicotine mucate displays irregular birefringent particles, typically less than about 10 µm. However, it is noted that the particles may exhibit different sizes and/or shapes, which may be dependent upon the method of preparation and/or the ratio of amorphous to crystalline solid present in the analyzed sample.

In another aspect of the present disclosure, a specific crystalline form of nicotine 4-acetamidobenzoate has been isolated and identified. Salts of acetamidobenzoic acid have been previously described. See, e.g., Lasslo et al., *J. Amer. Pharm. Assoc.* (1912-1977) (1959), 48, 345-7 and Gialdi et al., Farmaco, Edizione Scientifica (1959), 14, 15-24, which are incorporated herein by reference. According to certain aspects of the present invention, a novel crystalline form is provided and described according to certain parameters described herein.

This novel crystalline form of nicotine 4-acetamidobenzoate can, in some embodiments, be characterized by the x-ray powder diffraction (XRPD) pattern, as shown in FIG. 3. Agreement is good between the experimental pattern from the bulk sample and the pattern calculated from the single crystal x-ray structure. The XRPD patterns are obtained as described in the Experimental section of the present disclosure.

Full characterization data for nicotine 4-acetamidobenzoate, including a table of all relevant peaks in the x-ray diffraction pattern of nicotine 4-acetamidobenzoate, is provided in Example 2. The nicotine 4-acetamidobenzoate can be described as exhibiting an XRPD pattern having peaks at one or more of the following 2-theta diffraction angles: 16.839°, 17.854°, 20.134°, and 23.265°. Consistent with a crystalline form, this nicotine 4-acetamidobenzoate form exhibits a discrete melting point with an onset between about 130° C. and about 135° C. (e.g., about 134° C.).

Advantageously, in certain embodiments, a sample of nicotine 4-acetamidobenzoate is provided wherein at least a particular percentage comprises the crystalline polymorphic form described herein. For example, in some embodiments, nicotine 4-acetamidobenzoate comprising at least about 70%, at least about 75%, at least about 80%, at least about 85%, at least about 90%, at least about 95%, at least about 97%, at least about 98%, or at least about 99% of the polymorphic form described herein by weight is provided.

A single crystal x-ray diffraction (SCXRD) structure has been obtained for this crystalline form of nicotine 4-acetamidobenzoate, as shown in FIGS. 4A and 4B (showing two independent molecules of nicotine 4-acetamidobenzoate). The SCXRD structure was obtained as described in the Experimental section of the present disclosure. Anisotropic atomic displacement ellipsoids for the non-hydrogen atoms are shown at the 50% probability level. Hydrogen bonds are shown as dashed lines. Hydrogen atoms are displayed with an arbitrarily small radius. In certain embodiments, at least a given percentage of the crystalline nicotine 4-acetamidobenzoate provided as described herein is a single crystalline form. For example, in some embodiments, at least about 50%, at least about 60%, at least about 70%, at least about 80%, or at least about 90% of the crystalline 4-acetamidobenzoate is in a single crystalline form.

It is apparent from the x-ray structure that a proton has been transferred, confirming that the form is a salt. The x-ray structure further indicates that the nicotine is the S enantiomer. The SCXRD structure of the nicotine 4-acetamidobenzoate further indicates a hydrogen bonded head to tail arrangement of the acid molecules (with the acid carbonyl of one molecule hydrogen bonding to an NH functionality in a second), with nicotine molecules attached at regular intervals. This form of nicotine 4-acetamidobenzoate can be described has having a monoclinic crystal system.

In certain embodiments, the disclosed nicotine 4-acetamidobenzoate exhibits physical properties that render it suitable for incorporation into various products. For example, in some embodiments, the disclosed form is not significantly hygroscopic, with the bulk of its observed water uptake coming in the 80-90% relative humidity range. Accordingly, storage of this form is possible, given appropriate controls on the relative humidity level of the environment in which it is stored.

In another aspect of the present disclosure, a specific crystalline form of nicotine 2,5-dihydroxybenzoate (i.e., nicotine gentisate) has been isolated and identified. Salts of nicotine gentisate have been previously described. See, e.g., Perfetti, Beitraege zur Tabakforschung International (1983), 12(2), 43-54; Dezelic et al., Spectrochimica Acta, Part A: Molecular and Biomolecular Spectroscopy (1967), 23(4), 1149-53; Nikolin et al., Arhiv za Higijenu Rada i Toksikologiju (1966), 17(3), 303-8; Dezelic et al., Glasnik Hemicara Technol. Bosne Hercegovine et al. (1965), 13-14, 27-36; and Dezelic et al., Glasnik Drustva Hem. Technol. NR Bosne Hercegovine (1961), 10, 55-62, which are incorporated herein by reference. According to certain aspects of the present invention, a novel crystalline form of nicotine gentisate is provided and described according to certain parameters described herein.

Figure 5:
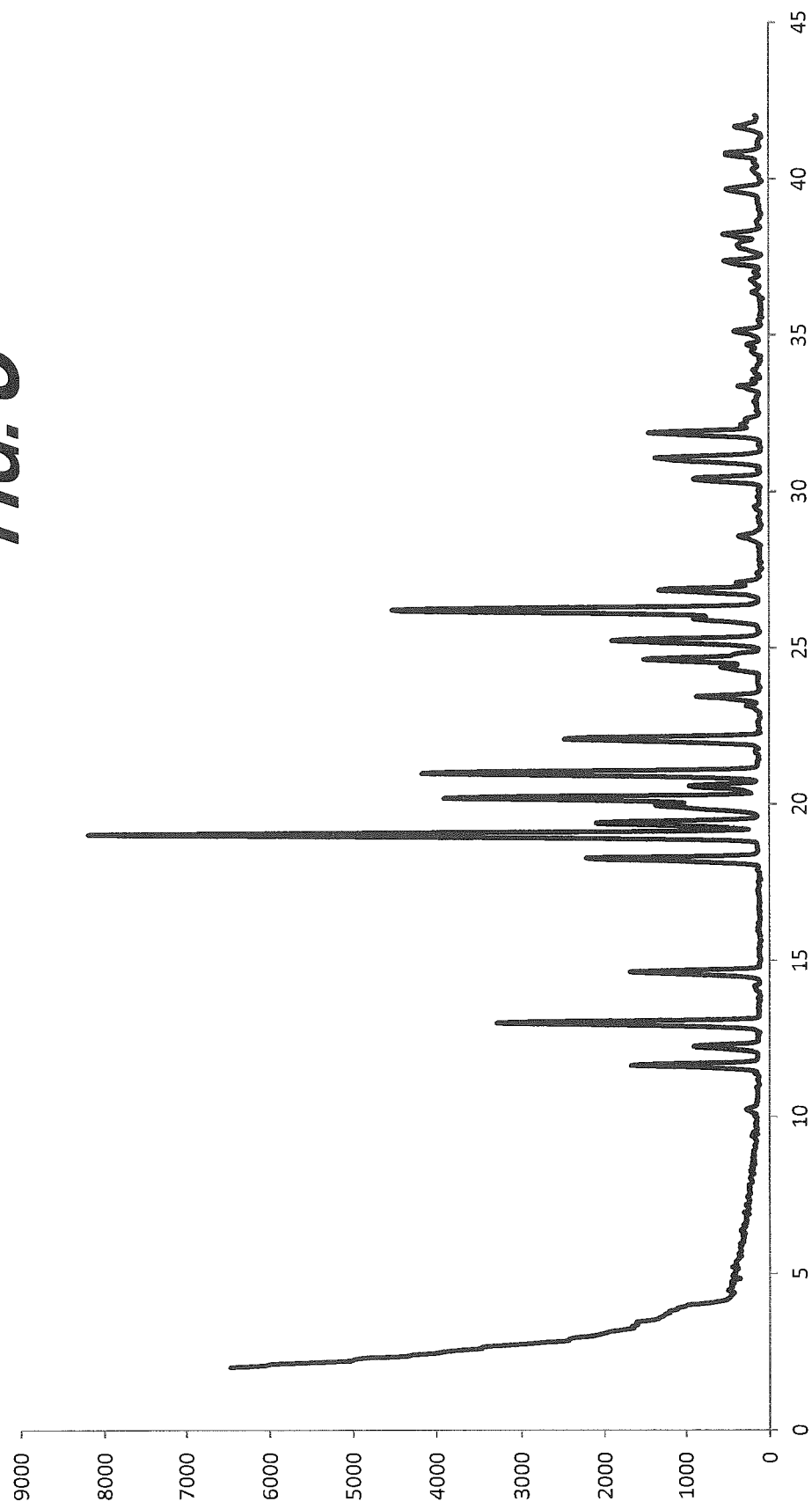
FIG. 5 is an x-ray powder diffraction pattern of crystalline nicotine gentisate, showing the experimental pattern and the pattern calculated from the single crystal x-ray structure.

This novel crystalline form of nicotine gentisate can, in some embodiments, be characterized by the x-ray powder diffraction (XRPD) pattern, as shown in FIG. 5. Agreement is good between the experimental pattern from the bulk sample and the pattern calculated from the single crystal x-ray structure. The XRPD patterns are obtained as described in the Experimental section of the present disclosure. Full characterization data, including a table of all relevant peaks in the x-ray diffraction pattern, is provided in Example 3. The nicotine gentisate can be described as exhibiting an XRPD pattern having peaks at one or more of the following 2-theta diffraction angles: 13.000°, 19.017°, 20.194°, and 21.000°. Consistent with a crystalline form, this nicotine 2,5-hydroxybenzoate form exhibits a discrete melting point with an onset between about 145° C. and about 150° C. (e.g., about 149° C.).

Advantageously, in certain embodiments, a sample of nicotine gentisate is provided wherein at least a particular percentage comprises the crystalline polymorphic form described herein. For example, in some embodiments, nicotine gentisate comprising at least about 70%, at least about 75%, at least about 80%, at least about 85%, at least about 90%, at least about 95%, at least about 97%, at least about 98%, or at least about 99% of the polymorphic form described herein by weight is provided.

Figure 6B:
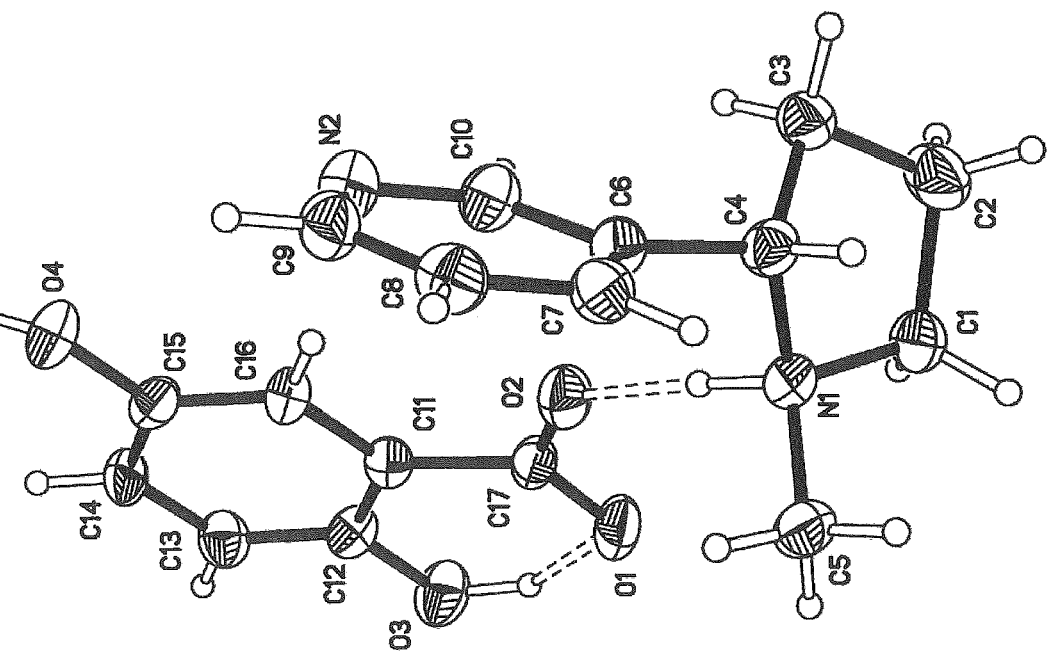
FIG. 6A is a view of a crystal structure obtained for nicotine gentisate and FIG. 6B is a view of the crystal packing of nicotine gentisate.
Figure 6A:
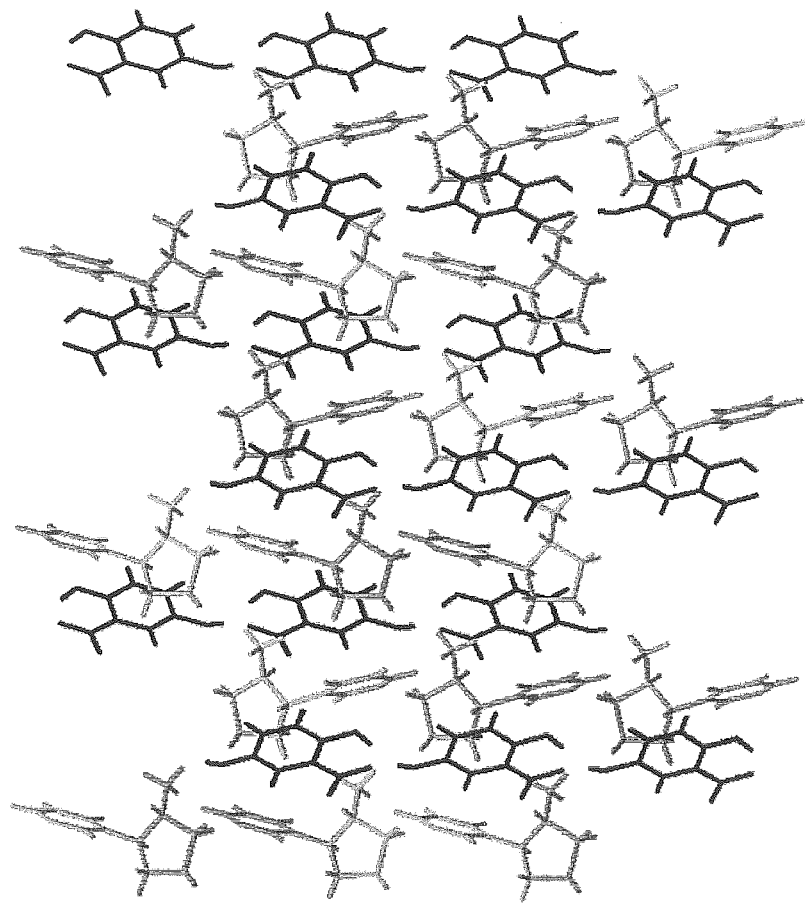

A single crystal x-ray diffraction (SCXRD) structure has been obtained for this crystalline form of nicotine gentisate, as shown in FIG. 6A. The SCXRD structure was obtained as described in the Experimental section of the present disclosure. Anisotropic atomic displacement ellipsoids for the non-hydrogen atoms are shown at the 50% probability level. Hydrogen bonds are shown as dashed lines. Hydrogen atoms are displayed with an arbitrarily small radius. In certain embodiments, at least a given percentage of the crystalline nicotine gentisate provided as described herein is a single crystalline form. For example, in some embodiments, at least about 50%, at least about 60%, at least about 70%, at least about 80%, or at least about 90% of the crystalline gentisate is in a single crystalline form. The crystal packing of the nicotine gentisate obtained is provided in FIG. 6B.

It is apparent from the x-ray structure of nicotine gentisate that a proton has been transferred, confirming that the form is a salt. The SCXRD structure of the nicotine gentisate further indicates a hydrogen bonded head to tail arrangement of the acid molecules (with one molecule hydrogen bonding to a second molecule), with nicotine molecules attached at regular intervals. This form of nicotine gentisate can be described as having a monoclinic crystal system.

In certain embodiments, the disclosed nicotine gentisate exhibits physical properties that render it suitable for incorporation into various products. In fact, the disclosed form of nicotine gentisate exhibits lower hygroscopicity and better thermal stability than the commercially available ditartrate dihydrate, e.g., as evidenced by the thermogravimetric analysis (TGA) and differential scanning calorimetry (DSC) studies described herein.

In further aspects, nicotine 3-hydroxybenzoate and nicotine malate are provided. XRPD patterns for these salts are provided at FIGS. 7 and 8, respectively. Additional data for these salts is provided in Examples 4 and 5.

In another aspect of the invention, nicotine 3,5-dihydroxybenzoate is provided. Nicotine 3,5-dihydroxybenzoate is formed from nicotine and 3,5-dihydroxybenzoic acid. In one aspect, a nicotine 3,5-dihydroxybenzoate salt is provided having a stoichiometry of about 1:1 nicotine:acid. In certain embodiments, nicotine 3,5-dihydroxybenzoate is provided in solid form and may be in crystalline and/or amorphous form.

In some embodiments, nicotine 3,5-dihydroxybenzoate can exist in anhydrous and/or one or more hydrated (e.g., dihydrate) forms. Accordingly, nicotine 3,5-dihydroxybenzoate salts can undergo form changes when exposed to varying humidity levels. An exemplary powder diffraction (XRPD) pattern of a sample of anhydrous nicotine 3,5-dihydroxybenzoate is provided in FIG. 9. Agreement is good between the experimental pattern from the bulk sample and the pattern calculated from the single crystal x-ray structure. The anhydrous nicotine 3,5-dihydroxybenzoate can be described as exhibiting an XRPD pattern having peaks at one or more of the following 2-theta diffraction angles: 12.7°, 17.8°, 19.7°, 20.2°, 21.3°, 24.5°, 24.9°, 25.8°, and 29.8°. Full characterization data, including a table of all relevant peaks in the x-ray diffraction pattern, is provided in Example 6. A $^1$H NMR spectrum of the anhydrous form of this material is provided in FIG. 10.

Figure 11:
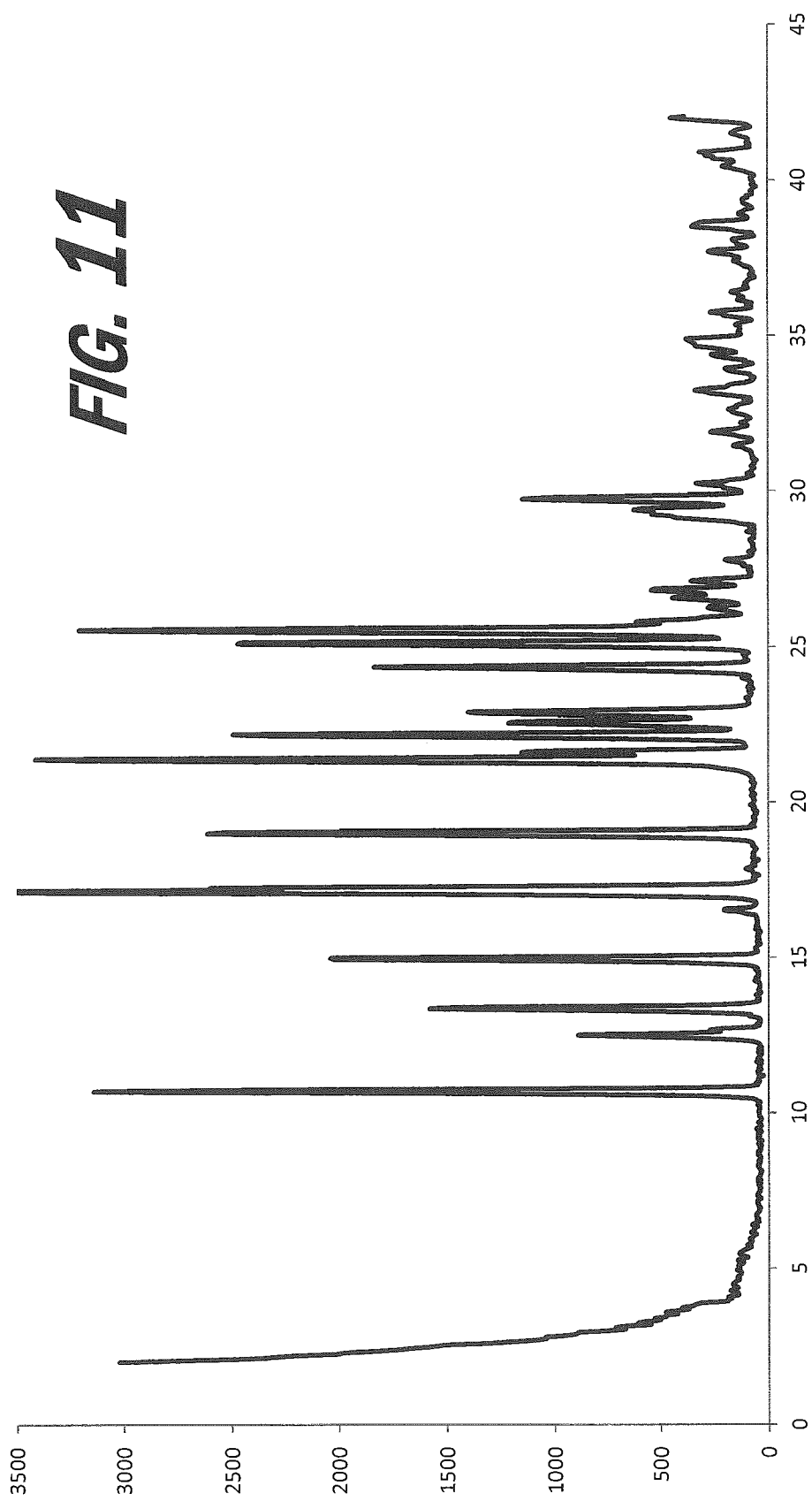
FIG. 11 is an x-ray powder diffraction pattern of nicotine 3,5-dihydroxybenzoate dihydrate.

An XRPD pattern of nicotine 3,5-dihydroxybenzoate dihydrate (prepared by exposure of the anhydrous form to humidity) is provided in FIG. 11. The nicotine 3,5-dihydroxybenzoate dihydrate can be described as exhibiting an XRPD pattern having peaks at one or more of the following 2-theta diffraction angles: 10.7°, 13.4°, 15.0°, 17.2°, 17.3°, 19.0°, 21.4°, 21.6°, 22.2°, 22.6°, 22.9°, 24.3°, 25.1°, 25.5°, and 29.7°. Full characterization data, including a table of all relevant peaks in the x-ray diffraction pattern, is provided in Example 6. A $^1$H NMR spectrum of the dihydrate form of this material is provided in FIG. 12. It is noted that VH-XRPD experiments confirmed the existence of this dihydrate form (exhibiting the same XRPD diffractogram as the material resulting from storage of the anhydrous form at 25° C./96% relative humidity). The dihydrate form in some embodiments can be converted back to the anhydrous form referenced above upon heating.

Figure 13:
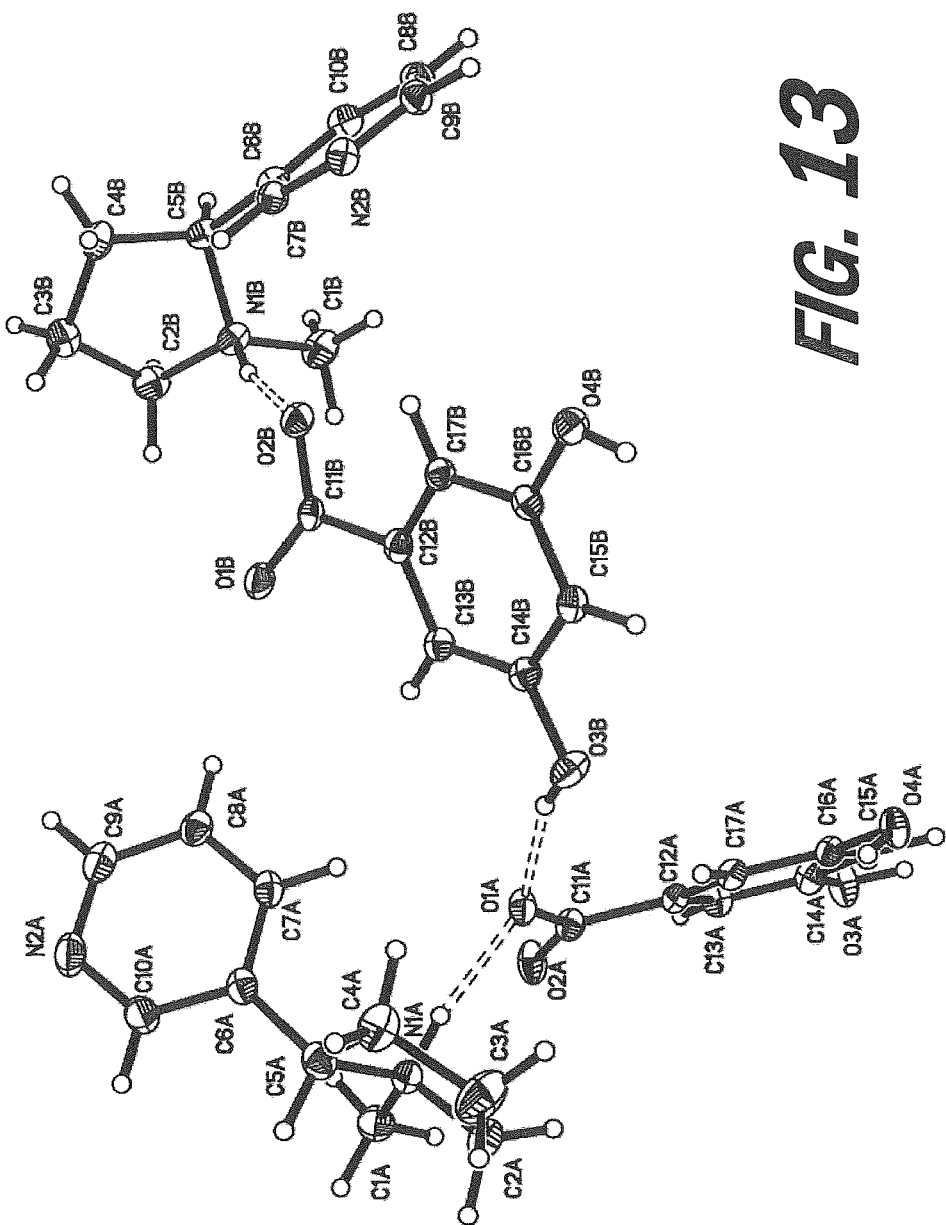
FIG. 13 is a view of a crystal structure obtained for anhydrous nicotine 3,5-dihydroxybenzoate.
Figure 14A:
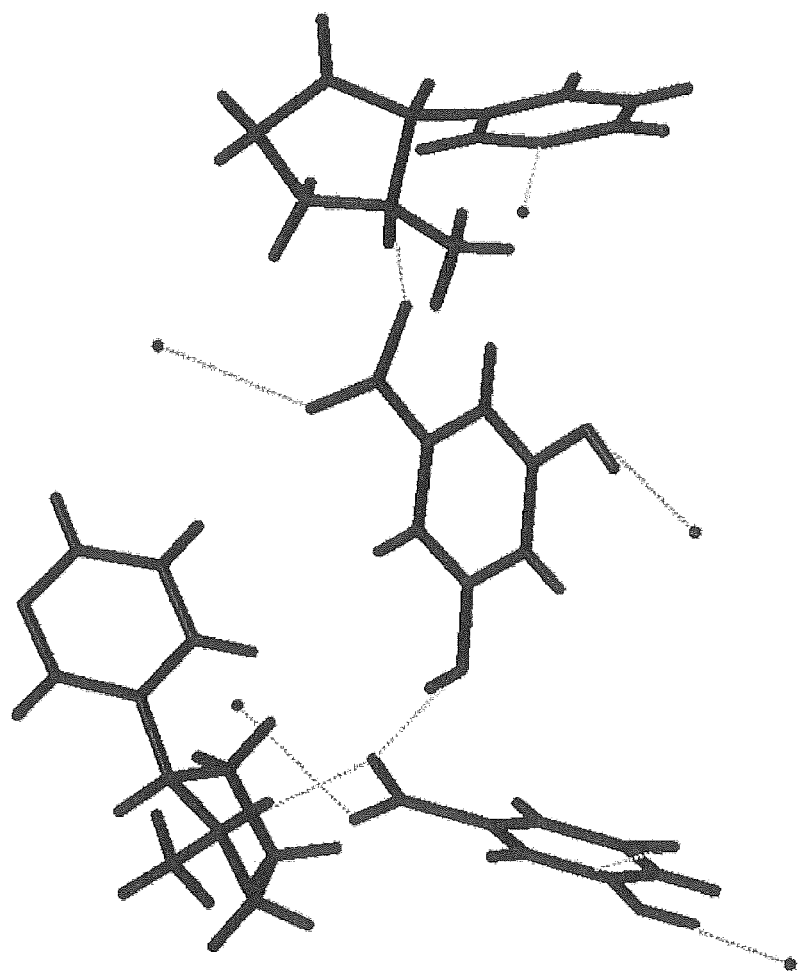
FIG. 14A is a plot showing hydrogen bonding in the asymmetric unit of anhydrous nicotine 3,5-dihyroxybenzoate
Figure 14B:
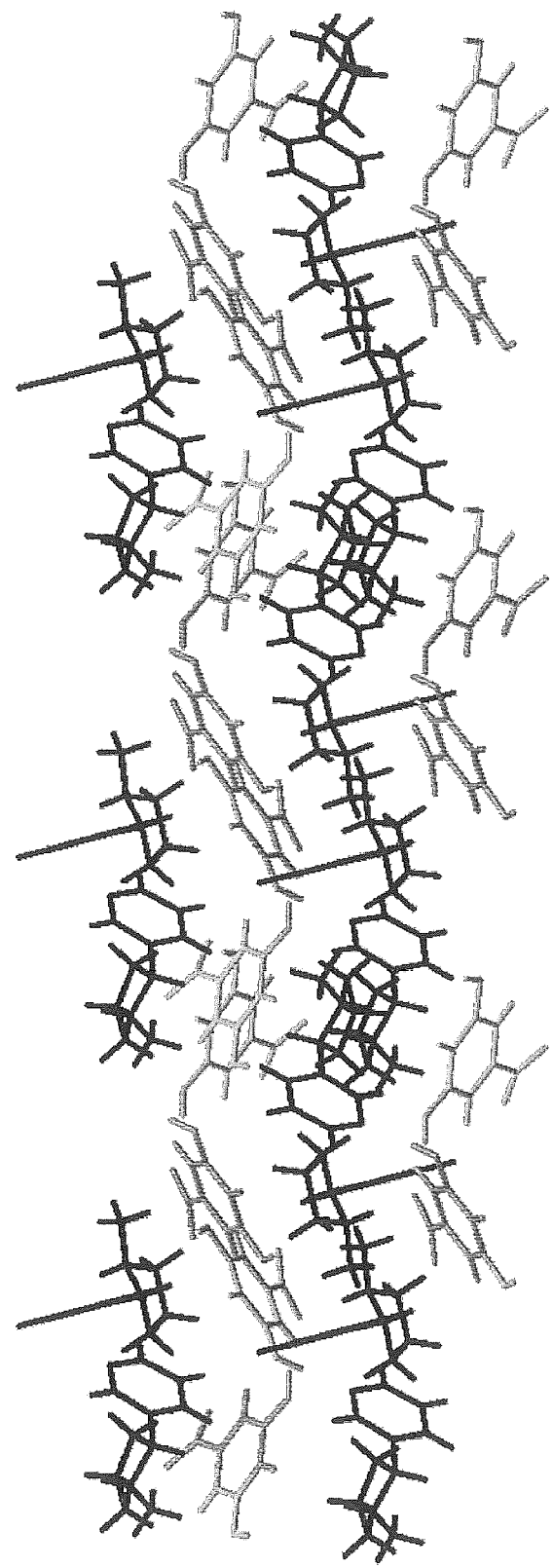
FIG. 14B is a view of the crystal packing of anhydrous nicotine 3,5-dihydroxybenzoate.

A single crystal x-ray diffraction (SCXRD) structure has been obtained for the crystalline form of anhydrous nicotine 3,5-hydroxybenzoate, as shown in FIG. 13. The SCXRD structure was obtained as described in the Experimental section of the present disclosure. Anisotropic atomic displacement ellipsoids for the non-hydrogen atoms are shown at the 50% probability level. Hydrogen bonds are shown as dashed lines. Hydrogen atoms are displayed with an arbitrarily small radius. In certain embodiments, at least a given percentage of the crystalline nicotine 3,5-dihydroxybenzoate provided as described herein is a single crystalline form. For example, in some embodiments, at least about 50%, at least about 60%, at least about 70%, at least about 80%, or at least about 90% by weight of the crystalline 3,5-dihydroxybenzoate is in a single crystalline form. A plot showing hydrogen bonding in the asymmetric unit of anhydrous nicotine 3,5-dihyroxybenzoate is presented in FIG. 14A and the crystal packing of the anhydrous nicotine 3,5-dihydroxybenzoate obtained is provided in FIG. 14B.

Consistent with a crystalline form, nicotine 3,5-dihydroxybenzoate may, in some embodiments, exhibit a relatively sharp melting point. For example, in certain embodiments, nicotine 3,5-dihydroxybenzoate can exhibit a discrete melting point with an onset of about 138° C. for the anhydrous form. The dihydrate form appears to melt at about 137° C. (with endotherms from 50-100° C.) and, although not intending to be limited by theory, it is believed that the dihydrate is being converted to the anhydrous form over the temperature range of 50-100° C. and it the converted anhydrous form then melts at about 137° C. In certain embodiments, polarized light microscopy of nicotine 3,5-dihydroxybenzoate reveals irregular particles, typically less than about 10 μm. However, it is noted that the particles may exhibit different sizes and/or shapes, which may be dependent upon the method of preparation and/or the ratio of amorphous to crystalline solid present in the analyzed sample.

In another aspect, nicotine 2,3-dihydroxybenzoate is provided. Nicotine 2,3-dihydroxybenzoate is formed from nicotine and 2,3-dihydroxybenzoic acid. In one aspect, a nicotine 2,3-dihydroxybenzoate salt is provided having a stoichiometry of about 1:1 nicotine:acid. In certain embodiments, nicotine 2,3-dihydroxybenzoate is provided in solid form and may be in crystalline and/or amorphous form.

Figure 16:
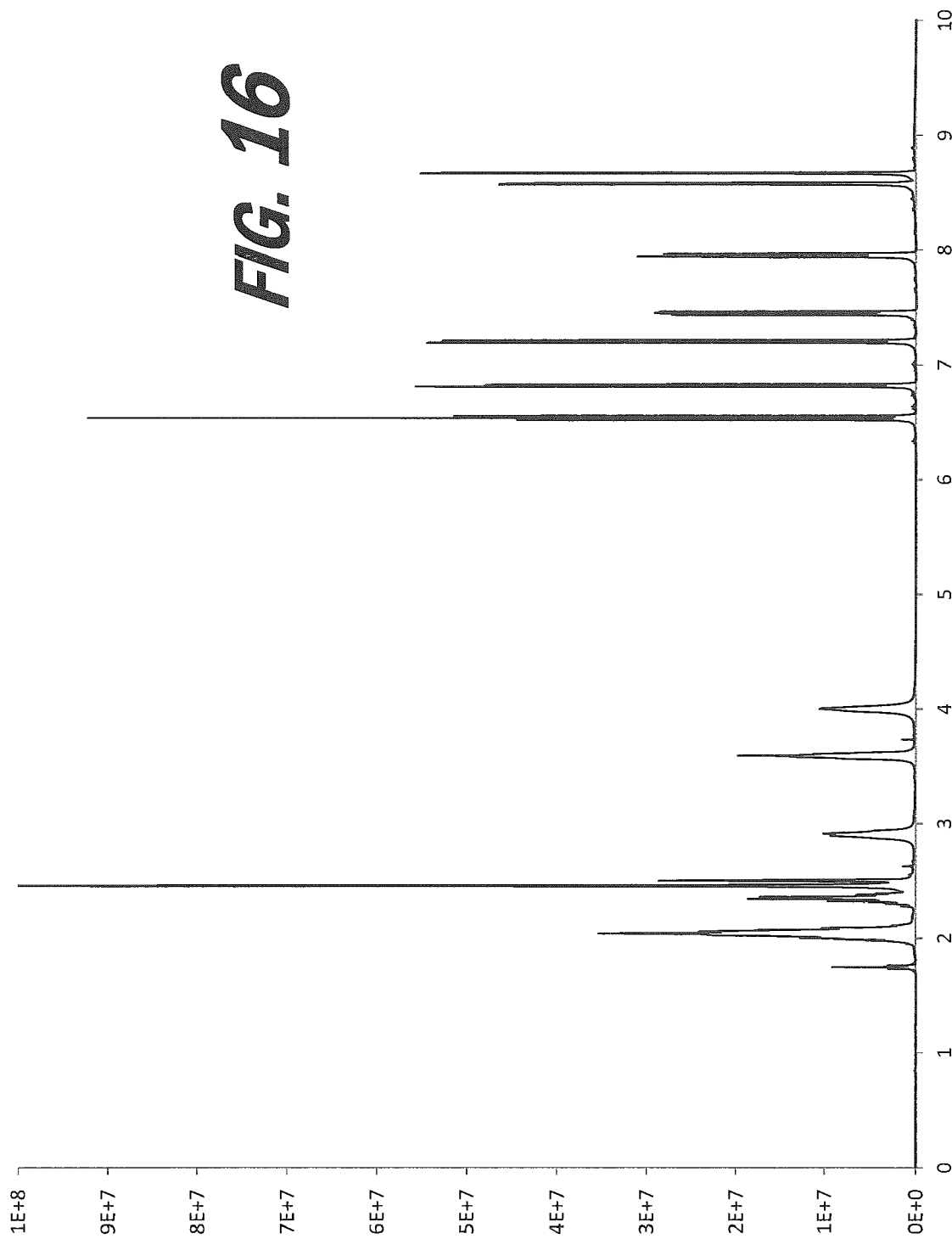
FIG. 16 is a $^1$H NMR spectrum of nicotine 2,3-dihydroxybenzoate.

In certain embodiments, nicotine 2,3-dihydroxybenzoate is provided in solid form and may be in crystalline and/or amorphous form. An exemplary x-ray powder diffraction (XRPD) pattern of a sample comprising nicotine 2,3-dihydroxybenzoate is provided in FIG. 15. The nicotine 2,3-dihydroxybenzoate can be described as exhibiting an XRPD pattern having peaks at one or more of the following 2-theta diffraction angles: 12.4°, 12.5°, 15.2°, 18.3°, 19.7°, 20.3°, 20.9°, 24.9°, 25.2°, 26.5°, and 30.4°. Full characterization data, including a table of all relevant peaks in the x-ray diffraction pattern, is provided in Example 7. A $^1$H NMR spectrum of this material is provided in FIG. 16.

Consistent with a crystalline form, nicotine 2,3-dihydroxybenzoate may, in some embodiments, exhibit a relatively sharp melting point. For example, in certain embodiments, nicotine 2,3-dihydroxybenzoate can exhibit a discrete melting point with an onset of about 157° C. for the anhydrous form. In certain embodiments, polarized light microscopy of nicotine 3,5-dihydroxybenzoate reveals irregular particles, typically less than about 10 μm. However, it is noted that the particles may exhibit different sizes and/or shapes, which may be dependent upon the method of preparation and/or the ratio of amorphous to crystalline solid present in the analyzed sample. Generally, the nicotine 2,3-dihydroxybenzoate exhibited low hygroscopicity and no change of form when exposed to humidity, properties desirable for easy handling.

In another aspect, a specific crystalline form of nicotine 1-hydroxy-2-naphthoate (i.e., nicotine xinafoate) has been isolated and identified. A salt of nicotine 1-hydroxy-2-naphthoate has been previously described. See Dezelic et al., Glasnik Drustva Hemicara Technol. Bosne Hercegoveni et al. (1961), 10:55-62, which is incorporated herein by reference. According to certain aspects of the present invention, a novel crystalline form of nicotine 1-hydroxy-2-naphthoate is provided and described according to certain parameters described herein.

Figure 17:
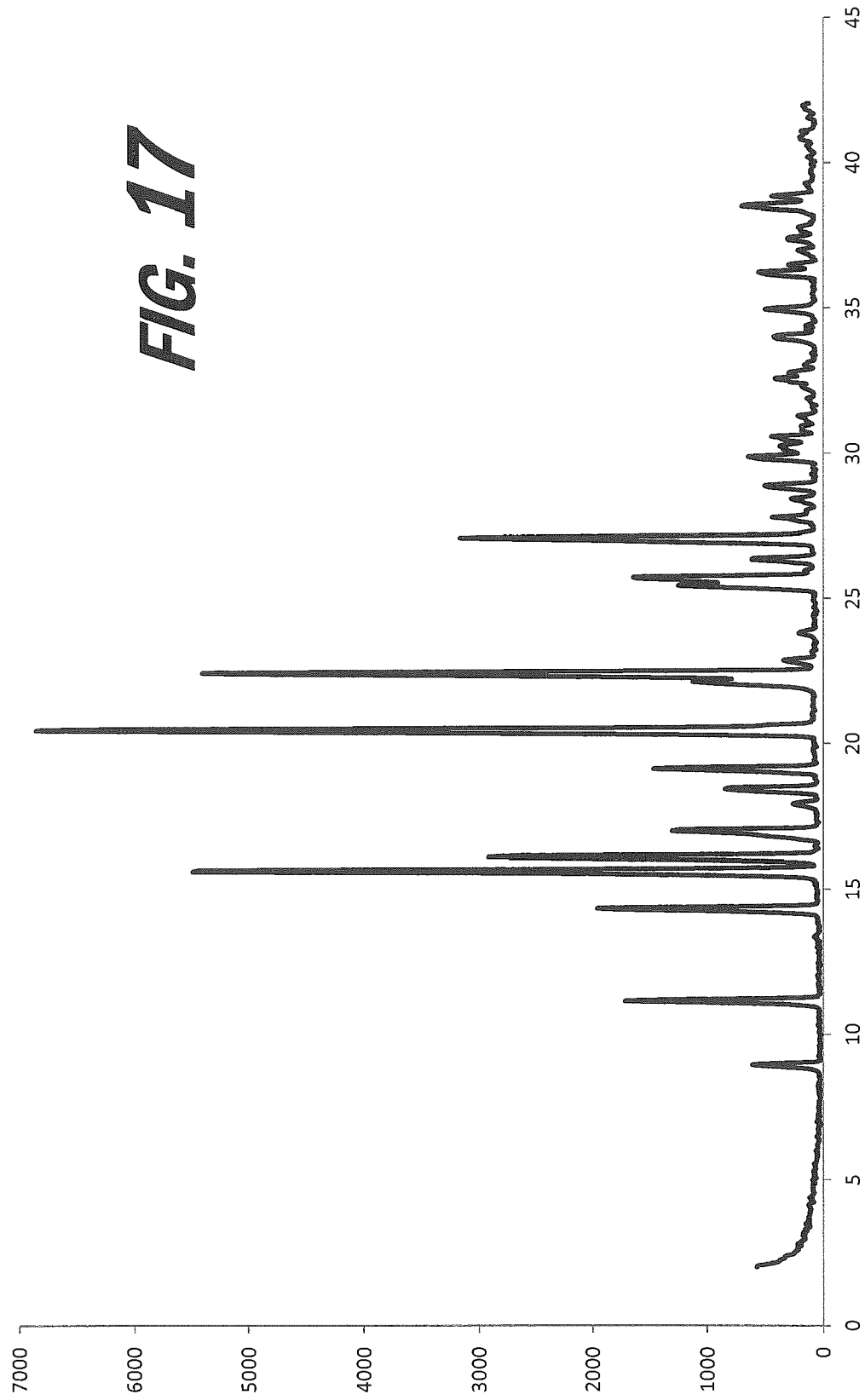
FIG. 17 is an x-ray powder diffraction pattern of nicotine 1-hydroxy-2-naphthoate.

The novel crystalline form of nicotine 1-hydroxy-2-naphthoate can, in some embodiments, be characterized by the x-ray powder diffraction (XRPD) pattern, as shown in FIG. 17. The nicotine 1-hydroxy-2-naphthoate can be described as exhibiting an XRPD pattern having peaks at one or more of the following 2-theta diffraction angles: 11.2°, 14.4°, 15.6°, 16.1°, 17.0°, 19.2°, 20.5°, 22.2°, 22.5°, 25.4°, 25.7°, and 27.1°. Full characterization data, including a table of all relevant peaks in the x-ray diffraction pattern, is provided in Example 8. The nicotine 1-hydroxy-2-naphthoate form can be described as exhibiting an XRPD pattern having peaks at one or more of the following 2θtheta diffraction angles: 15.6°, 16.1°, 20.5°, 22.5°, and 27.1°. Consistent with a crystalline form, this nicotine 1-hydroxy-2-naphthoate form exhibits a discrete melting point, with an onset between about 110° C. and about 115° C. (e.g., about 111° C.).

Figure 18:
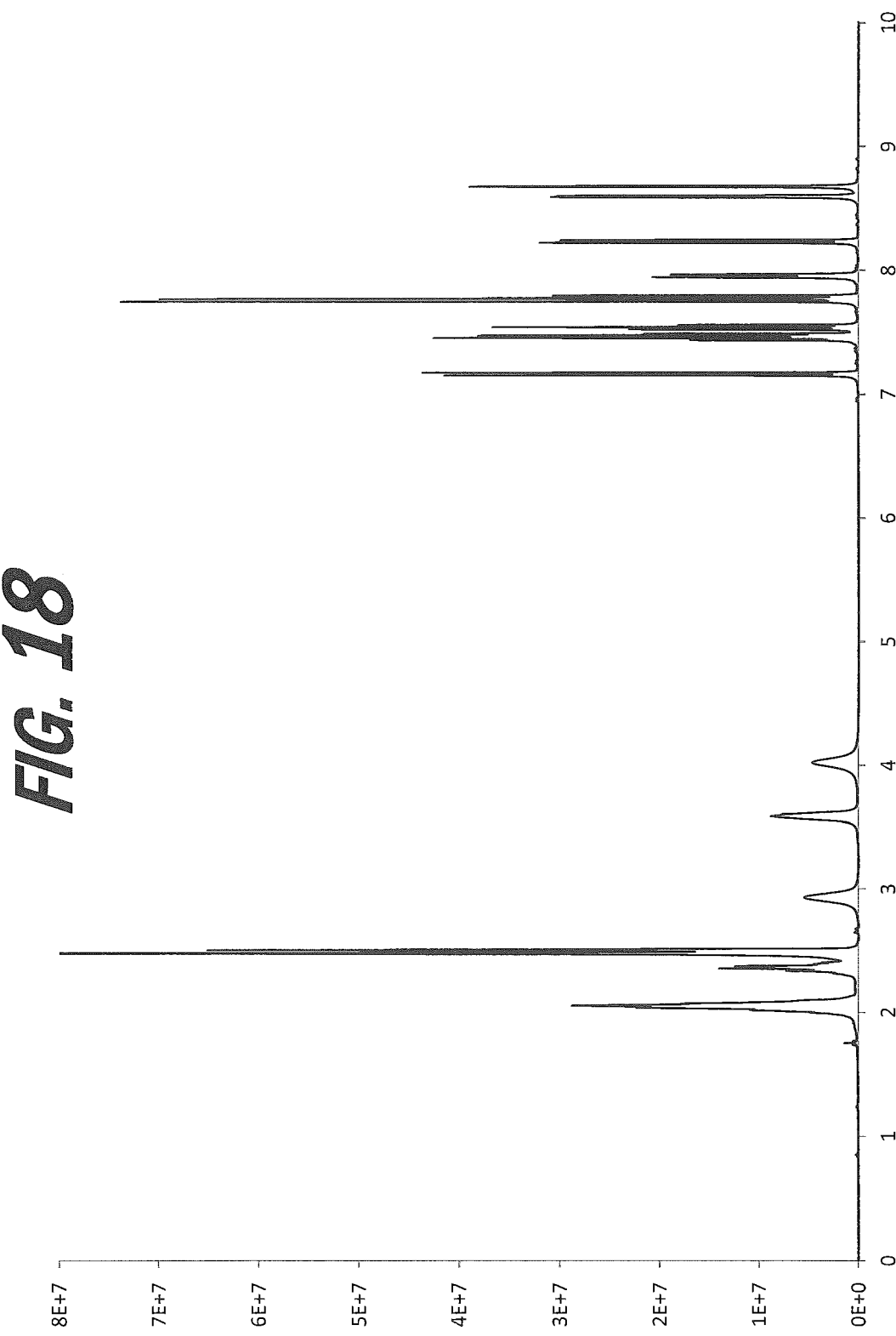
FIG. 18 is a $^1$H NMR spectrum of nicotine 1-hydroxy-2-naphthoate.

Advantageously, in certain embodiments, a sample of nicotine 1-hydroxy-2-naphthoate is provided wherein at least a particular percentage comprises the crystalline polymorphic form described herein. For example, in some embodiments, nicotine 1-hydroxy-2-naphthoate comprising at least about 70%, at least about 75%, at least about 80%, at least about 85%, at least about 90%, at least about 95%, at least about 97%, at least about 98%, or at least about 99% of the polymorphic form described herein by weight is provided A $^1$H NMR spectrum of the disclosed nicotine 1-hydroxy-2-naphthoate is provided in FIG. 18. This nicotine 1-hydroxy-2-napthoate form has certain desirable physical characteristics. For example, the nicotine 1-hydroxy-2-napthoate form disclosed herein exhibited low hygroscopicity and no change of form when exposed to humidity, properties desirable for easy handling.

One skilled in the art will understand that all diffraction pattern data provided herein should not be construed as absolute and, accordingly, the nicotine salts, co-crystals, and salt co-crystals of the invention are not limited to particles having XRPD patterns identical to FIGS. 1, 3, 5, 7, 8, 9, 11, 15, and 17. Any nicotine salts, co-crystals, or salt co-crystals having XRPD patterns substantially the same as those of FIGS. 1, 3, 5, 7, 8, 9, 11, 15, and 17 will be considered to fall within the scope of the invention. A person skilled in the art of X-ray powder diffraction is able to judge the substantial identity of X-ray powder diffraction patterns. Generally, a measurement error of a diffraction angle in an X-ray powder diffractogram is about 2-theta=0.5° or less (more suitably, about 2-theta=0.2° or less) and such degree of a measurement error should be taken into account when considering the X-ray powder diffraction pattern in FIGS. 1, 3, 5, 7, 8, 9, 11, 15, and 17 or the peak values provided herein. In other words, the peaks in FIGS. 1, 3, 5, 7, 8, 9, 11, 15, and 17 and the peak values given throughout the specification can be viewed, in certain embodiments, as being +/−0.5° or +/−0.2°. See Fundamentals of Powder Diffraction and Structural Characterization, Pecharsky and Zavalij, Kluwer Academic Publishers, 2003.

Other nicotine salts, co-crystals, and salt co-crystals are also encompassed by the present disclosure. For a list of pharmaceutically acceptable counter-ions, see Handbook of Pharmaceutical Salts—Properties, Selection, and Use, P. Heinrich Stahl, Camille G. Wermuth (Eds.) VHCA (Verlag Helvetica Chemica Acta-Zürich), Wiley-VCH (New York) 2002, which is incorporated herein by reference. For example, certain coformers useful for reaction with the nicotine, which may result in the formation of a salt, co-crystal, or salt co-crystal include, but are not limited to: acetic acid; adipic acid; ascorbic acid; capric (decanoic) acid; citric acid; D-glucuronic acid; D-gluconic acid; DL-lactic acid; L-lactic acid; galactaric (mucic) acid; hippuric (N-benzoylglycine) acid; hydrochloric acid; L-aspartic acid;

L-glutamic acid; L-glutaric acid; glycerophosphoric acid; glycolic acid; lauric acid; DL-malic acid; L-malic acid; DL-tartaric acid; L-tartaric acid; palmitic acid; phosphoric acid; sebacic (1,8-octanedicarboxylic) acid; stearic (octadecanoic) acid; succinic acid; sulfuric acid; and thiocyanic acid (HS-CN). Other exemplary coformers for reaction with the nicotine, which may result in the formation of a salt, co-crystal, or salt co-crystal include, but are not limited to, (+)-camphoric acid; 1,5-naphthalenedisulfonic acid; 1-hydroxy-2-naphthoic (xinafoic) acid; 2,5-dihydroxybenzoic (gentisic) acid; benzenesulfonic acid; benzoic acid; caprylic (octanoic) acid; cyclamic acid; ethanesulfonic acid; fumaric acid; D-glucoheptonic acid; 4-hydroxybenzoic acid; isobutyric acid; ketoglutaric (2-oxo-glutaric) acid; 2-ketobutyric acid; lactobionic acid; maleic acid; malonic acid; methanesulfonic acid; naphthalene-2-sulfonic acid; nicotinic acid; oleic (Z-octadecenoic) acid; orotic acid; oxalic acid; pamoic acid; pivalic acid; propionic acid; L-pyroglutamic acid; and p-toluenesulfonic acid.

Certain other types of coformers are generally associated with pharmacological effects and are not typically preferred for the preparation of salts, co-crystals, and salt co-crystals. Although complexes of nicotine with such coformers may not be preferred, in certain specialized embodiments, they may be reacted with nicotine to form salts, co-crystals, and/or salt co-crystals. Such coformers include, but are not limited to, (1S)-camphor-10-sulfonic acid; 4-acetamidobenzoic acid; 4-aminosalicylic acid, N-acetyl-4-aminosalicylic acid; caproic (hexanoic) acid; dichloroacetic acid; hydrobromic acid; DL-mandelic acid; L-mandelic acid; nitric acid; formic acid; salicylic acid; cinnamic (e.g., trans-cinnamic) acid; and undecylenic acid. Other exemplary coformers that may form salts, co-crystals, and/or salt co-crystals with nicotine include, but are not limited to, isothionic acid; lauric (dodecanoic) acid; 2-hydroxybenzoic acid; trans-2-hexanoic acid; trimesic acid; and 5-nitroisophthalic acid.

Various other coformers can be used to provide nicotine in the form of a salt, co-crystal, or co-crystal salt. Exemplary co-formers include, but are not limited to, L-proline, tromethamine; urea, xylitol; caffeine; glycine/glycine anhydride; vanillin; methyl 4-hydroxybenzoate (methylparaben); succinamide; L-alanine; mannitol; L-phenylalanine; saccharin; propylparaben; N-methylglucamine; L-tyrosine; gentisic acid; sorbic acid; benzoic acid; L-methionine; maltol; L-lysine, tromethamine; nicotinamide; isonicotinamide; phenylalanine; benzoquinone; terephthalaldehyde; 2,4-dihydroxybenzoic acid; and 4-hydroxybenzoic acid.

Additional coformers include pyruvic acid, 1-hydroxy-2-naphthoic acid, 4-aminobenzoic acid, 3,5-dihydroxybenzoic acid, 2,3-dihydroxybenzoic acid, 3,4-dihydroxybenzoic acid, 2,4-dihydroxybenzoic acid, vanillic acid, ethyl vanillin, isonicotinic acid, gallic acid, menthol (e.g., racemic menthol or (−)-menthol), paracetamol, aspirin, ibuprofen, naproxen, ketoprofen, flurbiprofen, glucose, serine, malic acid, acetamide, sulfacetamide, benzoic acid, 4-aminobenzoic acid, creatine, 2-hydroxyethanesulfonic acid, clofibric acid, taurine (tauric acid), iproniazid, L-histidine, L-arginine, L-asparagine, glutamine, L-cysteine, alanine, valine, isoleucine, leucine, morpholine, theronine, and N-methylglucamine.

Certain exemplary coformers that can provide a nicotine salt, co-crystal, or co-crystal salt are sugar-based acids (i.e., monosaccharides with a carboxyl group). Representative types of sugar acids include aldonic acids (e.g., glyceric acid, xylonic acid, gluconic acid, and ascorbic acid), ulosonic acids (e.g., neuraminic acid and ketodeoxyoctulosonic acid), uronic acids (e.g., glucuronic acid, galacturonic acid, and iduronic acid), and aldaric acids (e.g., tartaric acid, meso-galactaric acid/mucic acid, and D-glucaric acid/saccharic acid). In one preferred embodiment, the coformer or coformers used to provide a nicotine salt, co-crystal, or salt co-crystal according to the present disclosure is an aldaric acid, and in a particular preferred embodiment, the aldaric acid is mucic acid ((2S,3R,4S,5R)-2,3,4,5-tetrahydroxyhexanedioic acid, also referred to as galactaric or meso-galactaric acid).

Other exemplary coformers that can provide a nicotine co-crystal, salt, or co-crystal salt are polyfunctional aromatic acids. Polyfunctional aromatic acids often comprise a substituted or unsubstituted phenyl group as the aromatic component, but can alternatively comprise another aromatic moiety, e.g., pyridine, pyrazine, imidazole, pyrazole, oxazole, thiophene, naphthalene, anthracene, and phenanthrene. Substituents on the optionally substituted aromatic acids may be any type of substituent, including, but not limited to, halo (e.g., Cl, F, Br, and I); alkyl, halogenated alkyl (e.g., $CF_3$, 2-Br-ethyl, $CH_2F$, $CH_2Cl$, $CH_2CF_3$, or $CF_2CF_3$); alkenyl, hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate groups. Exemplary polyfunctional aromatic acids can be, for example:

substituted and unsubstituted aromatic dicarboxylic acids (e.g., 1,2-benzenedicarboxylic acid (phthalic acid), 1,3-benzenedicarboxylic acid (isophthalic acid), 1,4-benzenedicarboxylic acid (terephthalic acid), 2-iodo-1,3-benzenedicarboxylic acid, 2-hydroxy-1,4-benzenedicarboxylic acid, 2-nitro-1,4-benzenedicarboxylic acid, 3-fluoro-1,2-benzenedicarboxylic acid, 3-amino-1,2-benzenedicarboxylic acid, 3-nitro-1,2-benzenedicarboxylic acid, 4-bromo-1,3-benzenedicarboxylic acid, 4-hydroxy-1,3-benzenedicarboxylic acid, 4-amino-1,2-benzenedicarboxylic acid, 4-nitro-1,2-benzenedicarboxylic acid, 4-sulfo-1,2-benzenedicarboxylic acid, 4-amino-1,3-benzenedicarboxylic acid, 5-bromo-1,3-benzenedicarboxylic acid, 5-hydroxy-1,3-benzenedicarboxylic acid, 5-amino-1,3-benzenedicarboxylic acid, 5-nitro-1,3-benzenedicarboxylic acid, 5-ethynyl-1,3-benzenedicarboxylic acid, 5-cyano-1,3-benzenedicarboxylic acid, 5-nitro-1,3-benzenedicarboxylic acid, 2,5-hydroxy-1,4-benzenedicarboxylic acid, and 2,3,5,6-tetrafluoro-1,4-benzenedicarboxylic acid;

substituted and unsubstituted hydroxybenzoic acids (e.g., 2-hydroxybenzoic acid (salicylic acid), 3-hydroxybenzoic acid, 4-hydroxybenzoic acid, 2-methyl-4-hydroxybenzoic acid, 3-tert-butyl-4-hydroxybenzoic acid, 4-ethoxy-2-hydroxybenzoic acid, 3-chloro-5-hydroxybenzoic acid, 5-chloro-2-hydroxybenzoic acid, 3-bromo-4-hydroxybenzoic acid, 3-bromo-5-hydroxybenzoic acid, 4-bromo-2-hydroxybenzoic acid, 5-bromo-2-hydroxybenzoic acid, 2-fluoro-5-hydroxybenzoic acid, 3-fluoro-4-hydroxybenzoic acid, 3-fluoro-2-hydroxybenzoic acid, 3-fluoro-5-hydroxybenzoic acid, 2-fluoro-6-hydroxybenzoic acid, 4-fluoro-3-hydroxybenzoic acid, 2-fluoro-4-hydroxybenzoic acid, 5-fluoro-2-hydroxybenzoic acid, 2-amino-3-hydroxybenzoic acid, 2-amino-5-hydroxybenzoic acid, 3-amino-2-hydroxybenzoic acid, 3-amino-4-hydroxybenzoic acid, 3-amino-5-hydroxybenzoic acid, 4-amino-2-hydroxybenzoic acid, 4-amino-3-hydroxybenzoic acid, 5-amino-2-hydroxybenzoic acid (mesalamine), 5-aminomethyl-2-hydroxybenzoic acid, 4-formyl-3-hydroxybenzoic acid, 3-formyl-4-hydroxybenzoic acid, 5-(acetylamino)-2-hydroxybenzoic acid), 4-nitro-2-hydroxybenzoic acid, 3,5-diethyl-4-hydroxybenzoic acid, 3,5-di-tert-butyl-4-hydroxybenzoic acid, 3,5-diisopropyl-2-hydroxybenzoic acid, 3,4-dimethoxy-4-hydroxybenzoic acid (syringic acid), 3,5-dichloro-2-hydroxybenzoic acid, 3,5-dichloro-4-hydroxybenzoic acid, 3,6-dichloro-2-hydroxybenzoic acid, 2,3-difluoro-4-hydroxybenzoic acid, 3,4-difluoro-2-hydroxybenzoic acid, 3,5-dibromo-2-hydroxybenzoic acid, 3,5-diodo-2-hydroxybenzoic acid, 4-amino-5-chloro-2-hydroxybenzoic acid, 3,5-dinitro-2-hydroxybenzoic acid, 2,4,6-tribromo-2-hydroxybenzoic acid, 2,3,5,6-tetrafluoro-4-hydroxybenzoic acid, and 2,3,4,5-tetrafluoro-6-hydroxybenzoic acid);

substituted and unsubstituted dihydroxybenzoic acids (e.g., 2,3-dihydroxybenzoic acid (pyrocatechuic acid/hypogallic acid), 2,4-dihydroxybenzoic acid (β-resorcylic acid), 2,5-dihydroxybenzoic acid (gentisic acid/hydroquinonecarboxylic acid), 2,6-dihydroxybenzoic acid (γ-resorcylic acid), 3,4-dihydroxybenzoic acid (protocatechuic acid), 3,5-dihydroxybenzoic acid (α-resorcylic acid), 4-hydroxy-3-methoxybenzoic acid (vanillic acid), 6-methyl-2,4-dihdroxybenzoic acid (orsellenic acid), 4-bromo-3,5-dihydroxybenzoic acid, 5-bromo-2,4-dihydroxybenzoic acid, 5-bromo-3,4-dihydroxybenzoic acid, 6-carboxymethyl-2,3-dihydroxybenzoic acid, 3,5-dibromo-2,4-dihydroxybenzoic acid, 3,5-dichloro-2,6-dihydroxybenzoic acid, and 5-amino-3-chloro-2,4-dihydroxybenzoic acid); and substituted and unsubstituted trihydroxybenzoic acids (e.g., 2,3,4-trihydroxybenzoic acid, 2,4,5-trihydroxybenzoic acid, 2,4,6-trihydroxybenzoic acid (phloroglucinol carboxylic acid), and 3,4,5-trihydroxybenzoic acid (gallic acid)).

substituted and unsubstituted aromatic tricarboxylic acids (e.g., 1,2,3-benzenetricarboxylic acid, 1,2,4-benzenetricarboxylic acid (trimellitic acid); and substituted and unsubstituted aromatic tetracarboxylic acids (e.g., 1,2,3,4-benzenetetracarboxylic acid (mellophanic acid) and 1,2,4,5-benzenetetracarboxylic acid (pyromellitic acid).

Other coformers useful in certain embodiments are flavor acids, including but not limited to, 3-hydroxy-2-oxopropionic acid; 2-oxobutyric acid (2-ketobutyric acid), 3-methyl-2-oxobutanoic acid; 3-methyl-2-oxopentanoic acid; 4-methyl-2-oxopentanoic acid; and 2-oxopentanedioic acid. Additional coformers can have higher molecular weights, such as 2-oxo-3-phenylpropionic acid; 5-oxooctanoic acid; and 5-oxodecanoic acid.

It is noted that certain coformers as described herein may contain one or more chiral centers, which may be either of the (R) or (S) configuration, or which may comprise a mixture thereof. As a result, various diasteromeric nicotine salts, co-crystals and salt co-crystals may be provided according to the present disclosure. The invention includes such diastereomers, either individually, or admixed in any proportions. Certain coformers as described herein may be geometric isomers, including but not limited to cis and trans isomers across a double bond. The invention includes all nicotine salts, co-crystals, and salt co-crystals prepared with such isomers, which may be provided in the form of pure isomers or in admixture with other isomers.

The method(s) by which the nicotine salts, co-crystals, and salt co-crystals described herein can be produced can vary. In some embodiments, no solvent (or a minimal amount of solvent) is used to prepare the nicotine salts, co-crystals, and salt co-crystals. Although in so-called "solventless" methods, a solvent is commonly not used, it is noted that one or more solvents may optionally be added (typically in a small amount) to the mixture to facilitate the formation of a nicotine salt, co-crystal, or salt co-crystal. In certain embodiments, the components (i.e., the nicotine and the one or more coformers) are combined in the absence of a solvent to form a slurry. Solids comprising nicotine salts, co-crystals, and/or salt co-crystals may be isolated therefrom via common methods (e.g., filtration). The slurry may be optionally heated such that the nicotine and one or more coformers interact in melted form to produce a salt, co-crystal, or salt co-crystal. In certain embodiments, physical methods are used to combine the components (i.e., the nicotine and the one or more coformers). For example, the nicotine and the coformer(s) can be ground together mechanically (e.g., using a mortar and pestle, ball mill, or vibratory mill).

In certain embodiments, a combination of nicotine and a coformer in a given solvent (or solvents) and evaporation of that solvent can provide the desired nicotine salt, co-crystal, or salt co-crystal. Typically, in such methods, the nicotine and coformer are provided in stoichiometric amounts (i.e., no excess nicotine or coformer is added). In such methods, selection of solvent is important, as the solvent (or solvents) in which the reaction is conducted can impact the intermolecular interactions. The evaporation of solvent can be done at a controlled rate (e.g., slowly) to encourage the preparation of a single nicotine salt, co-crystal, or salt co-crystal crystal for characterization. For example, the evaporation of solvent may be effected over the course of hours, days, weeks, or months.

In some embodiments, a combination of nicotine and a coformer in a given solvent (or solvents) and addition of a non-solvent can provide the desired nicotine salt, co-crystal, or salt co-crystal. Exemplary solvents and non-solvents that can be used for the preparation of nicotine salts, co-crystals, and salt co-crystals include, but are not limited to, water, alcohols (e.g., methanol, ethanol, n-butanol, isopropanol), ethers (e.g., diethyl ether, petroleum ether), ethyl acetate, acetone, tetrahydrofuran, methylene chloride, chloroform, alkanes (e.g., pentane, hexane, heptane, octane, nonane, cyclohexane), benzene, toluene, 1,4-dioxane, and combinations thereof. In some embodiments, nicotine salts, co-crystals, and salt co-crystals can be prepared in supercritical fluids.

In other embodiments, the desired nicotine salt, co-crystal, or salt co-crystal can be prepared by freeze drying and subsequent maturation of a solution of nicotine and one or more coformers. For example, a solution may be prepared, frozen, and lyophilized to remove the solvent. A maturation solvent can then be added and the resulting solids can be obtained by common methods (e.g., filtration). Maturation solvents include, but are not limited, the types of solvents noted above.

The method of production of nicotine salts, co-crystals, and salt co-crystals as described herein may, in some embodiments, employ an excess of the coformer component. In such embodiments, it can advantageously be possible to purify the resulting salt, co-crystal, or salt co-crystal by removing excess coformer therefrom (i.e., that coformer which is not part of the structure of the salt, co-crystal, or salt co-crystal). Exemplary means for salt, co-crystal, or salt co-crystal formation that may, in certain embodiments, be applicable for the preparation of the nicotine salts, co-crystals, and salt co-crystals described herein are disclosed, for example, in U.S. Pat. No. 8,513,236 to Schultheiss et al.; U.S. Pat. No. 8,470,832 to George et al.; U.S. Pat. No. 8,466,280 to Grunenberg et al.; U.S. Pat. No. 8,415,507 to Schultheiss et al.; U.S. Pat. No. 8,350,085 to Childs; U.S. Pat. No. 8,241,371 to Hanna et al.; U.S. Pat. No. 8,212,079 to Childs; U.S. Pat. No. 8,173,625 to Brittain et al; U.S. Pat.

No. 8,163,790 to Childs; U.S. Pat. No. 8,197,592 to Imamura et al.; U.S. Pat. No. 8,058,437 to Bauer et al.; U.S. Pat. No. 7,935,817 to Blazecka et al.; U.S. Pat. No. 7,927,613 to Almarsson et al.; U.S. Pat. No. 7,452,555 to Childs; U.S. Pat. No. 7,008,742 to Molaire; U.S. Pat. App. Pub. Nos. 2013/0203806 to Chorlton et al.; 2013/0072440 to Dokou et al.; 2013/0040970 to Cosgrove et al.; 2012/0258170 to Kruthiventi et al.; 2012/0028998 to Sansone et al.; 2012/0028930 to Kalofonos et al.; 2012/0022117 to Gruss et al.; 2011/0257340 to Childs; 2011/0251426 to Hanna et al.; 2011/0236478 to Dokou et al.; 2011/0152266 to Grunenberg et al.; 2010/0204204 to Zaworotko et al; 2008/0280858 to Hanna et al., 2007/0287194 to Childs et al.; 2003/0224006 to Zaworotko et al.; and 2002/0048610 to Cima et al., which are all incorporated herein by reference in their entireties. Other references that provide exemplary means for the formation of certain nicotine salts include M. Dezelic and B. Nikolin, "Nicotine Compounds with Aromatic Acids. Part II," Glasnik Drustva Hemicara Technol. N. R. Bosne I Hercegovine, Sarajevo, 10 (1961) 55-62 and M. Dezelic and D. Tomic, "Nicotine Compounds with Aromatic Acids," Kem. Vjestnik 17 (1943):39-57, which are incorporated herein by reference.

For the preparation of nicotine mucate, in one embodiment, the salt is provided by combining the acid and nicotine in the absence of solvent. In some embodiments, an excess of nicotine is added to the reaction mixture and, advantageously, excess nicotine is removed (e.g., by vacuum and/or by washing/filtration, such as with THF, heptane, and/or EtOAc).

For the preparation of the novel polymorphic form of nicotine 4-acetamidobenzoate described herein, in one embodiment, the salt is provided by combining the acid and nicotine in the absence of solvent. For example, in one embodiment, 4-acetamidobenzoic acid is suspended in the minimum amount of nicotine required to produce a mobile slurry, which is stirred/shaken to form the nicotine salt. In another embodiment, a solvent (e.g., THF) is used to facilitate salt formation. For example, 4-acetamidobenzoic acid can be dissolved in THF, nicotine can be added thereto, and the resulting mixture can be stirred/shaken to produce the salt. The solvent can be removed (e.g., by evaporation) to provide the desired nicotine 4-acetamidobenzoate form. In some embodiments, the solid is washed, e.g., with THF, heptane, and/or EtOAc.

For the preparation of the novel polymorphic form of nicotine gentisate described herein, in one embodiment, the salt is provided by combining the acid and nicotine in the absence of solvent. For example, in one embodiment, gentisic acid is suspended in the minimum amount of nicotine required to produce a mobile slurry, which is stirred/shaken to form the nicotine salt. In another embodiment, a solvent (e.g., THF) is used to facilitate salt formation. For example, 4-acetamidobenzoic acid can be dissolved in THF, nicotine can be added thereto, and the resulting mixture can be stirred/shaken to produce the salt. The solvent can be removed (e.g., by evaporation) to provide the desired nicotine 4-acetamidobenzoate. In some embodiments, the solid is washed, e.g., with THF and/or heptane.

For the preparation of the nicotine 3,5-dihydroxybenzoate described herein, in one embodiment, the salt is provided by combining the acid and nicotine in a solvent (e.g., THF or acetone). For example, 3,5-dihydroxybenzoic acid can be dissolved in THF or acetone, followed by nicotine; the resulting mixture can be stirred/shaken to give the solid salt. The solvent can be removed (e.g., by evaporation) and optionally washed as described above (e.g., with heptane) to provide the desired 3,5-dihydroxybenzoate. In certain embodiments, this method provides the anhydrous form, which can readily be converted to a hydrated form, such as the dihydrate form described herein (e.g., by exposing the anhydrous form to elevated humidity levels, e.g., 96% relative humidity at 25° C. for 16 h). It is understood that varying amounts of humidity, temperature, and time may provide the hydrated (e.g., dihydrate) form.

For the preparation of nicotine 2,3-dihydroxybenzoate as described herein, in one embodiment, the salt can be prepared in neat nicotine (in the absence of solvent). In another embodiment, a solvent can be employed. For example, 2,3-dihydroxybenzoic acid can be dissolved in THF, followed by nicotine; the resulting mixture can be stirred/shaken to give the solid salt. The solvent can be removed (e.g., by evaporation) and optionally washed as described above (e.g., with heptane) to provide the desired nicotine 2,3-dihydroxybenzoate.

For the preparation of the nicotine 1-hydroxy-2-naphthoate form described herein, in one embodiment, the salt can be prepared in neat nicotine (in the absence of solvent). In another embodiment, a solvent can be employed. For example, 1-hydroxy-2-naphthoic acid can be dissolved in THF, followed by nicotine; the resulting mixture can be stirred/shaken to give the solid salt. The solvent can be removed (e.g., by evaporation) and optionally washed as described above (e.g., with heptane) to provide the desired polymorphic crystalline form of nicotine 1-hydroxy-2-naphthoate.

Desirably, single crystal x-ray diffraction (SCXRD) can be used in some embodiments to determine the makeup of the solids (i.e., the nicotine salts, co-crystals, and salt co-crystals). However, suitable, x-ray quality crystals cannot always be readily produced. Therefore, a variety of other solid state spectroscopic techniques can be used including, but not limited to, x-ray powder diffraction (XRPD), Raman spectroscopy, FTIR spectroscopy, vibrational spectroscopy, polarized light microscopy (PLM), and solid state NMR. The nicotine salts, co-crystals, and salt co-crystals described herein may be further characterized, for example, using such techniques as $^{13}C$ NMR and $^1H$ NMR (in a suitable solvent, e.g., in $D_2O$ or DMSO-$d_6$) to evaluate the chemical structure, Gravimetric Vapor Sorption (GVS) to evaluate the hygroscopicity, thermogravimetric analysis (TGA) and differential scanning calorimetry (DSC) to evaluate the thermal properties, and/or chromatography (e.g., HPLC) in a suitable solvent to evaluate the purity. Products as described herein can be further analyzed via Karl Fischer Titration (KF) to determine the water content.

It is noted that, in certain cases, it is difficult to distinguish between co-crystals and salts. Typically, distinguishing a salt from a co-crystal requires evidence of proton transfer, which may not be straightforward to identify even with single crystal x-ray diffraction. In other terms, distinguishing a salt from a co-crystal generally requires evidence of ionic interactions, as opposed to merely non-ionic interactions. Accordingly, although the novel compositions described herein are described as salts, it is noted that in some embodiments, it may not be known whether a given product exists in salt, co-crystal, or salt co-crystal form or in some type of intermediate form (e.g., wherein the proton has not been transferred to a basic site, but may reside in space between the donor conformer and acceptor).

The nicotine salts, co-crystals, and salt co-crystals described herein can be incorporated into various products, including tobacco-containing products. The important characteristics of nicotine salts, co-crystals, and salt co-crystals for use in different types of products vary, as will be discussed in detail below.

The nicotine salts, co-crystals, and salt co-crystals provided herein can, in some embodiments, be used as compositions in the manufacture of smoking articles. For example, salts, co-crystals, and salt co-crystals prepared in accordance with the present invention can be mixed with casing materials and applied to tobacco as a casing ingredient or as a top dressing. Still further, salts, co-crystals, and salt co-crystals of the present disclosure can be incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in U.S. Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Typically, the amount of nicotine salt, co-crystal, or salt co-crystal incorporated into a smoking article is that amount sufficient to provide the desired amount of free nicotine in the mainstream smoke produced therefrom. For example, in some embodiments, the smoking article may provide nicotine in an amount of about 0.1 mg to about 10 mg, about 0.5 mg to about 9 mg, or about 1 mg to about 8 mg. Accordingly, the amount of nicotine salt, co-crystal, or salt co-crystal incorporated into the smoking article can be, for example, that amount sufficient to produce these amounts of nicotine when the article is used.

Figure 19:
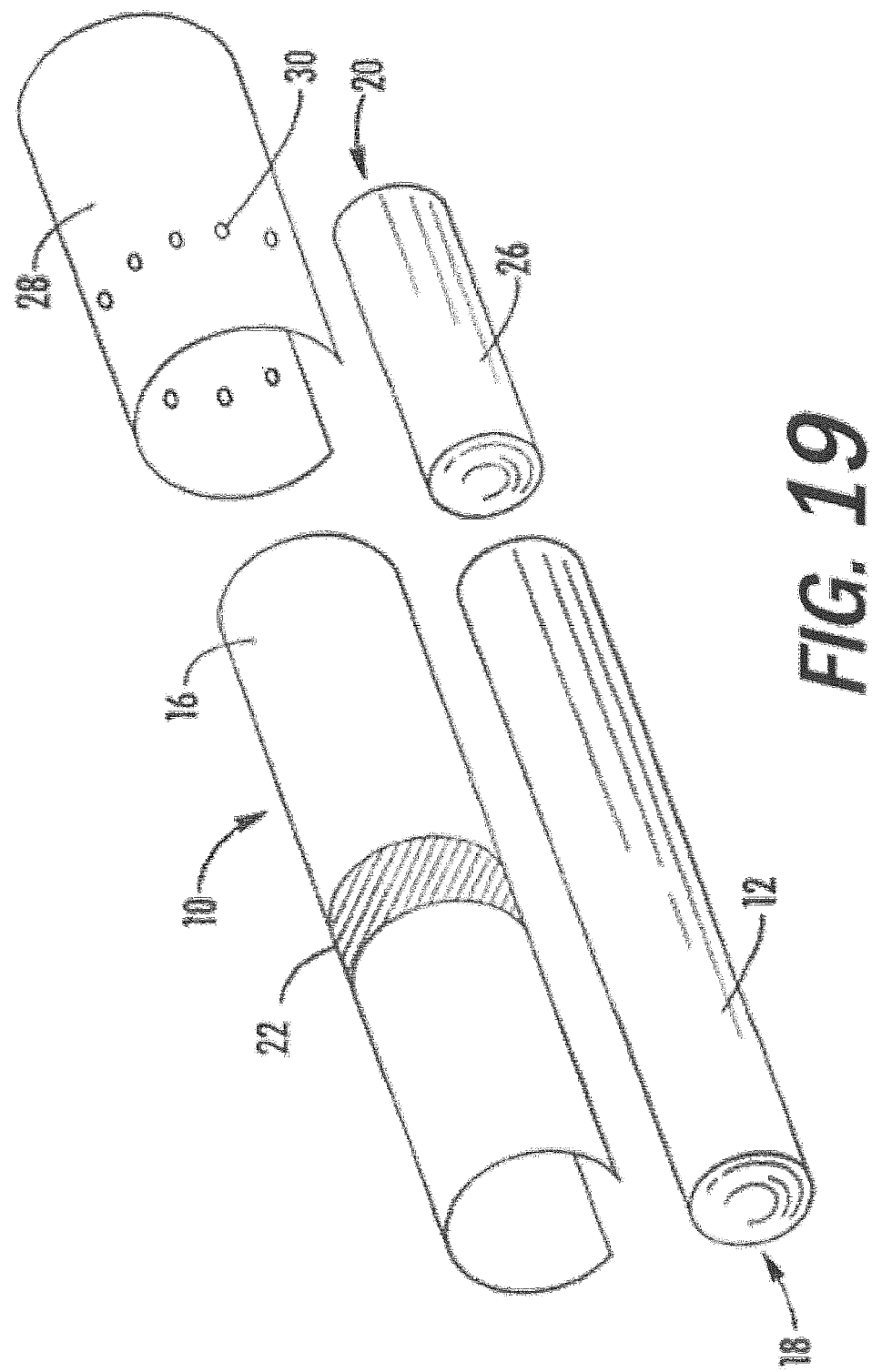
FIG. 19 is an exploded perspective view of a smoking article having the form of a cigarette, showing the smokable material, the wrapping material components, and the filter element of the cigarette.

Referring to FIG. 19, there is shown a smoking article 10 in the form of a cigarette and possessing certain representative components of a smoking article that can contain the formulation of the present invention. The cigarette 10 includes a generally cylindrical rod 12 of a charge or roll of smokable filler material (e.g., about 0.3 g to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The salts of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

The temperature at which nicotine, the coformer component (or components), and any degradation products thereof are released from a nicotine salt, co-crystal, or salt co-crystal can be a relevant consideration in the context of smoking articles. It is typically important that nicotine is released from the salt, co-crystal, or salt co-crystal (i.e., that the nicotine transfers to the mainstream smoke and is delivered to the user) at the burn temperature of the smoking article. It can also be important in some embodiments to ensure that certain undesirable coformers and/or degradation products thereof are not transferred to the mainstream smoke (and delivered to the user). The relevant temperature may vary slightly, depending upon the specific location(s) of the salt, co-crystal, or salt co-crystal within the smoking article. For example, in certain embodiments, the temperature at which a smoking article burns (and thus the temperature to which the salt is exposed) can be between at least about 100° C., at least about 200° C., or at least about 500° C., including between about 100° C. and about 500° C. in certain regions of a smoking article and between about 600° C. and about 900° C. in other regions of a smoking article. These considerations can impact selection of the salts, co-crystals, or salt co-crystals that are suitable for a particular application.

In other embodiments, the nicotine salts, co-crystals, and salt co-crystals disclosed herein can be incorporated within smokeless tobacco products. Representative smokeless tobacco compositions according to the present invention can have various types of formats and configurations, and as a result, the character, nature, behavior, consistency, shape, form, size and weight of the composition can vary. In some embodiments, the nicotine salts, co-crystals, and salt co-crystals disclosed herein can be incorporated into smokeless tobacco products, such as loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. The shape of a representative composition can be generally spherical, cylindrical (e.g., ranging from the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, capsule, and caplet types of products. Various types of smokeless tobacco products are described or referenced in U.S. Pat. Pub. Nos. 2013/0206150 to Duggins et al.; 2013/0074855 to Holton, Jr.; 2012/0118310 to Cantrell et al.; 2012/0138073 to Cantrell et al.; 2012/0138074 to Cantrell et al.; and 2012/0152265 to Dube et al., which are all incorporated herein by reference.

Figure 20:
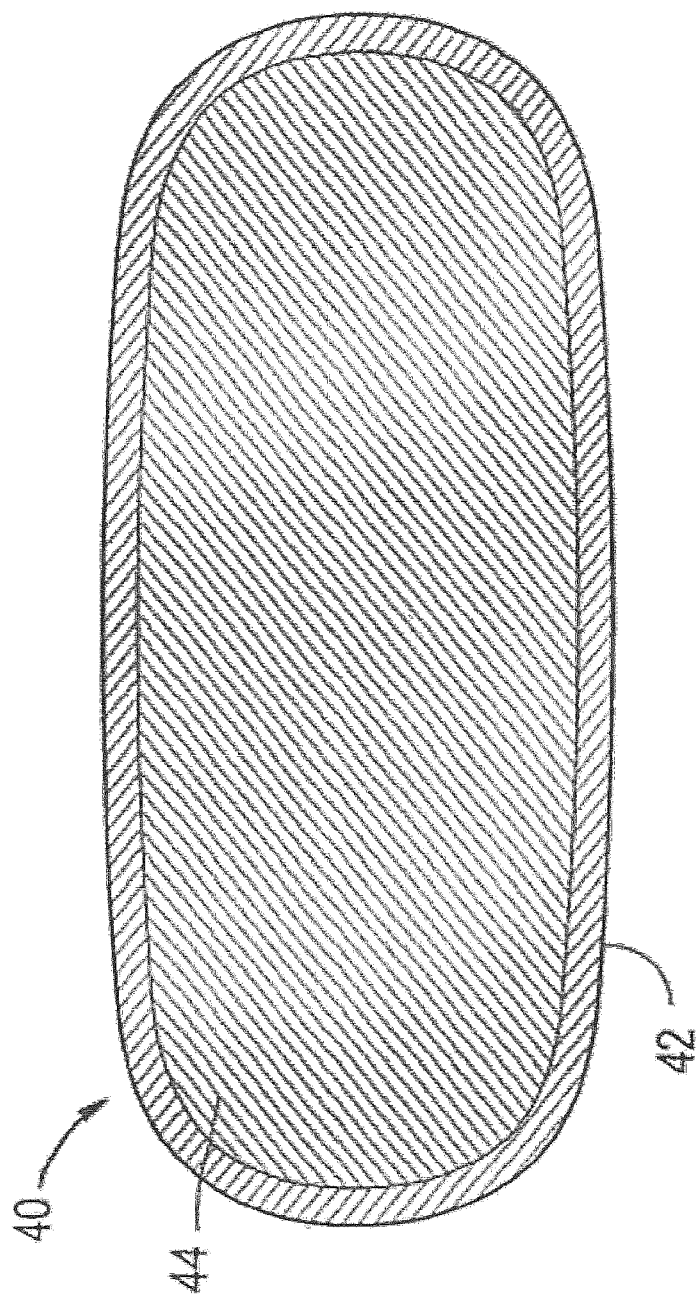
FIG. 20 is a cross-sectional view of a smokeless tobacco product embodiment, taken across the width of the product, showing an outer pouch filled with a smokeless tobacco composition of the invention.

Referring to FIG. 20, a representative snus type of tobacco product comprising one or more nicotine salts, co-crystals, or salt co-crystals according to the present disclosure is shown. In particular, FIG. 20 illustrates a smokeless tobacco product 40 having a water-permeable outer pouch 42 containing a smokeless tobacco composition 44. Any of the components of the tobacco product can comprise one or more nicotine salts, co-crystals, or salt co-crystals, according to the present disclosure (e.g., the interior or exterior of the pouch lining or a portion of the smokeless tobacco composition contained therein).

Other exemplary smokeless tobacco products into which the salts, co-crystals, and salt co-crystals described herein can be incorporated can have the form of a gum, lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; U.S. Pat. Pub. Nos. 2013/0074855 and 2013/0078307 to Holton, Jr.; 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; and 2013/0312774 to Holton, Jr., which are all incorporated herein by reference.

One representative type of smokeless tobacco product comprising one or more of the nicotine salts, co-crystals, or salt co-crystals described herein is a lozenge, e.g., as substantially described in U.S. Pat. App. Pub. Nos. 2013/0312774, 2013/0074856, and 2013/0074855, all to Holton, Jr., which are incorporated herein by reference. Such lozenges can comprise, in addition to one or more nicotine salts, co-crystals, or salt-co-crystals, a majority of one or more sugar alcohols (e.g., isomalt and maltitol syrup), e.g., in an amount of at least about 50% by weight, at least about 70% by weight, at least about 80% by weight, or at least about 90% by weight. Other ingredients of particular interest in such lozenge products include, but are not limited to, salts (e.g., NaCl), sweeteners (e.g., sucralose), and one or more flavorings.

The amount of nicotine salt, co-crystal, or salt co-crystal incorporated within a smokeless tobacco composition can vary and can be dependent, in part, on the specific type of smokeless tobacco composition. Clearly, the amount of a given nicotine salt, co-crystal, or salt co-crystal to be incorporated within a product will depend on the desired nicotine content of that product, and can be calculated based on the mass of the coformer and the stoichiometry of the salt, co-crystal, or salt co-crystal. Exemplary amounts include from about 0.1% by weight of the consumable material to about 10% by weight of the consumable or inhalable material. For example, for a lozenge, the amount of nicotine salt, co-crystal, or salt co-crystal is at least about 0.5%, generally at least about 1%, often at least about 1.5%, often at least about 2%, often at least about 2.5%, and frequently at least about 3% by weight of the product, e.g., about 0.5% to about 10%, including about 1% to about 5% by weight of the product. The amount of nicotine salt, co-crystal, or salt co-crystal can be determined based on the desired nicotine content in the lozenge.

Various other substances can be added to the smokeless tobacco compositions comprising the nicotine salts, co-crystals, or salt co-crystals of the present invention. For example, excipients such as fillers or carriers for active ingredients (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, gum arabic, lecithin, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No. 10), and lubricants or processing aids (e.g., calcium stearate or magnesium stearate) are added to the compositions in certain embodiments. Other exemplary types of ingredients include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), effervescing materials such as certain acid/base combinations, oral care additives (e.g., thyme oil, *eucalyptus* oil, and zinc), preservatives (e.g., potassium sorbate, and the like), syrups (e.g., honey, high fructose corn syrup, and the like), and mixtures thereof. In certain embodiments, the smokeless tobacco composition can include lipid components that provide a meltable composition that melts (as opposed to merely dissolving) in the oral cavity, such as compositions set forth in U.S. Pat. Pub. No. 2012/0037175 to Cantrell et al., which is incorporated by reference herein. Exemplary encapsulated additives that can be included within the smokeless tobacco products disclosed herein are described, for example, in WO 2010/132444 to Atchley, which has been previously incorporated by reference herein. See also, the smokeless tobacco ingredients set forth in U.S. Pat. Pub. Nos. 2012/0055494 to Hunt et al. and 2012/0199145 to Byrd et al., which are incorporated by reference herein.

The manners and methods used to formulate and manufacture the smokeless tobacco product can vary. Ingredients, including the nicotine salts, co-crystals, or salt co-crystals described herein, can be combined and processed into the desired composition by techniques such as extrusion, compression, molding, spraying, and the like. It is noted that certain considerations noted above for electronic smoking articles are not relevant in the context of a smokeless tobacco product. For example, nicotine salts, co-crystals, or salt co-crystals that are useful in smokeless tobacco products need not transfer to aerosol form at a given temperature. In smokeless tobacco products, the main consideration is that the nicotine salt, co-crystal, or salt co-crystal contained therein can provide nicotine when the smokeless tobacco product is placed in the mouth of the user (i.e., at some point during residence of the smokeless tobacco product in the mouth of the user). Accordingly, certain nicotine salts, co-crystals, or salt co-crystals that are useful for one type of tobacco product may not be useful for others.

In certain embodiments, the nicotine salts, co-crystals, and salt co-crystals provided according to the present disclosure are incorporated within electronic smoking articles.

Figure 21:
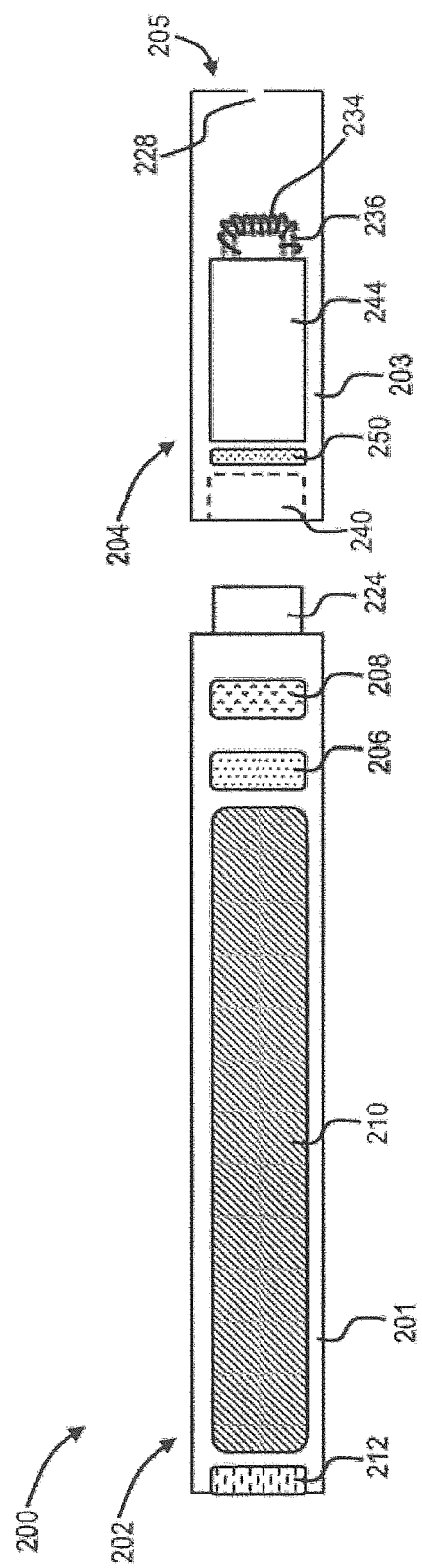
FIG. 21 is a cross-sectional view of an electronic smoking article, which can encompass a variety of combinations of components useful in forming an electronic aerosol delivery device.

An exemplary embodiment of an electronic smoking article 200 incorporating a nicotine salt, co-crystal, or salt co-crystal according to the present disclosure is shown in FIG. 21. As illustrated therein, a control body 202 can be formed of a housing 201 that can include a control component 206, a flow sensor 208, a battery 210, and an LED 212. The electronic smoking article also may comprise a cartridge 204 that can be formed of a housing 203 enclosing a reservoir 244 that is in fluid communication with a transport element 236 adapted to wick or otherwise transport an aerosol precursor composition stored in the reservoir to a heater 234 (e.g., a resistive heating wire that may be coiled around at least a portion of the transport element). Exemplary reservoirs and transport elements are disclosed in U.S. Pat. Pub. No. 2014/0261487 to Chapman et al., and exemplary heaters are disclosed in U.S. Pat. Pub. No. 2014/0157583 to Ward et al., the disclosures of which are incorporated herein by reference in their entireties. An opening 228 may be present in the cartridge housing 203 at a mouthend 205 thereof to allow for egress of formed aerosol from the cartridge 204. Such components are representative of the components that may be present in a control body and/or cartridge and are not intended to limit the scope of components that are encompassed by the present disclosure.

The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. Other types of connections (e.g., a screw thread connection) also are encompassed. The electronic smoking article 200 may be adapted for air intake, which may be provided in a coupler as described, for example, in U.S. Pat. Pub. No. 2014/0261408 to DePiano et al., the disclosure of which is incorporated herein by reference in its entirety. The cartridge 204 also may include one or more electronic components 250, which may include an IC, a memory component, a sensor, or the like. The electronic component 250 may be adapted to communicate with the control component 206 so as to provide an input. See, for example, U.S. Pat. Pub. Nos. 2014/0096781 to Sears et al. and 2014/0096782 to Ampolini et al., the disclosures of which are incorporated herein by reference in their entirety.

The electronic smoking article can encompass a variety of combinations of components useful in forming an electronic aerosol delivery device. Reference is made for example to the following: a reservoir and heater system for controllable delivery of multiple aerosolizable materials disclosed in U.S. Pat. Pub. No. 2014/0000638 to Sebastian et al.; microheaters as disclosed in U.S. Pat. Pub. No. 2014/0060554 to Collett et al.; carbon-based cartridges and components thereof, as disclosed U.S. Pat. Pub. No. 2013/0255702 to Griffith, Jr. et al.; single-use cartridges as disclosed in U.S. Pat. Pub. No. 2014/0060555 to Chang et al.; aerosol precursor transport elements, such as disclosed in U.S. Pat. Pub. No. 2014/0209105 to Sears et al.; charging components, such as an adaptor disclosed in U.S. Pat. Pub. No. 2014/0261495 to Novak, III et al.; vibration components, such as disclosed in U.S. Pat. Pub. No. 2015/0020825 to Galloway et al.; and batteries, such as disclosed in U.S. Pat. Pub. No. 2010/0028766 to Peckerar et al.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

In certain embodiments, the aerosol precursor comprises a nicotine salt, co-crystal, or salt co-crystal as disclosed herein. In one embodiment, the aerosol precursor composition can comprise, for example, a polyhydric alcohol (e.g., glycerin, propylene glycol, or a combination thereof), water, a nicotine salt, co-crystal, or salt co-crystal as described herein, and a flavorant (e.g., menthol). Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Flavoring agents also can include acidic or basic characteristics (e.g., organic acids, such as levulinic acid, succinic acid, and pyruvic acid). Representative types of aerosol precursor compositions are set forth in U.S. Pat. No. 4,793,365 to Sensabaugh, Jr. et al.; U.S. Pat. No. 5,101,839 to Jakob et al.; U.S. Pat. Pub. No. 2013/0008457 to Zheng et al.; and Chemical and Biological Studies on New Cigarette Prototypes that Heat Instead of Burn Tobacco, R. J. Reynolds Tobacco Company Monograph (1988). The disclosures of all of the foregoing documents are incorporated herein by reference in their entireties.

One or more acid components can be included within the aerosol precursor, e.g., to modify the sensory characteristics of the aerosol precursor and the aerosol produced therefrom. Organic acids particularly may be incorporated into the aerosol precursor to affect the flavor, sensation, and/or organoleptic properties of nicotine. Such organic acids can be included in the aerosol precursor with nicotine in varying amounts ranging from greater than equimolar to less than equimolar (based on total organic acid content) with the nicotine. A range of organic acids can be used in accordance with such embodiments, e.g., as set forth in Perfetti, *Beitrage Tabakforschung Int.*, 12, 43-54 (1983), which is incorporated herein by reference. Certain exemplary organic acids that may be useful include, but are not limited to, such acids as tartaric acid, ascorbic acid, fumaric acid, citric acid, malic acid, lactic acid, aspartic acid, salicylic acid, 4-amino salicylic acid, N-acetyl-4-aminosalicylic acid, p-toluenesulfonic acid, succinic acid, pyruvic acid, formic acid, acetic acid, propionic acid, isobutyric acid, butyric acid, alpha-methylbutyric acid, 2-ketobutyric acid, isovaleric acid, beta-methylvaleric acid, caproic acid, 2-furoic acid, phenylacetic acid, heptanoic acid, octanoic acid, nonanoic acid, oxalic acid, malonic acid, glycolic acid, levulinic acid, 4-aminobenzoic acid, 4-acetamidobenzoic acid, 3-hydroxybenzoic acid, 2,5-dihydroxybenzoic acid, 2,3-dihydroxybenzoic acid, 2,4-dihydroxybenzoic acid, 3,4-dihydroxybenzoic acid, vanillic acid, mucic acid, cyclamic acid, benzenesulfonic acid, 2-hydroxyethanesulfonic acid, 1-hydroxy-2- naphthoic acid, ketoglutaric acid, D-glucuronic acid, maleic acid, glutamic acid, L-pyroglutamic acid, nicotinic acid, isonicotinic acid, gallic acid, phthalic acid, mandelic acid, hippuric acid, cinnamic acid, adipic acid, orotic acid, sorbic acid, clofibric acid, tauric acid, and combinations of two or more such organic acids. By using a nicotine salt, co-crystal, or salt co-crystal in place of nicotine, it may be possible in certain embodiments to reduce and or eliminate the amount of acid advantageously incorporated within the aerosol precursor.

The amount of aerosol precursor composition that is used within the smoking article is such that the article exhibits acceptable sensory and organoleptic properties, and desirable performance characteristics. For example, it is highly preferred that sufficient aerosol precursor composition components, such as glycerin and/or propylene glycol, be employed in order to provide for the generation of a visible mainstream aerosol that in many regards resembles the appearance of tobacco smoke. Typically, the amount of aerosol-generating material incorporated into the smoking article is in the range of about 1.5 g or less, about 1 g or less, or about 0.5 g or less. The amount of aerosol precursor composition can be dependent upon factors such as the number of puffs desired per cartridge used with the smoking article. It is desirable for the aerosol-generating composition not to introduce significant degrees of unacceptable off-taste, filmy mouth-feel, or an overall sensory experience that is significantly different from that of a traditional type of cigarette that generates mainstream smoke by burning tobacco cut filler. The selection of the particular aerosol-generating material and reservoir material, the amounts of those components used, and the types of tobacco material used, can be altered in order to control the overall chemical composition of the mainstream aerosol produced by the smoking article.

Typically, the amount of nicotine incorporated into an aerosol precursor of an electronic smoking article is that amount sufficient to provide the desired amount of free nicotine in the aerosol produced therefrom. For example, the article may provide nicotine in an amount of about 0.01 mg to about 0.5 mg, about 0.05 mg to about 1 mg, about 0.08 mg to about 0.5 mg, about 0.1 mg to about 0.3 mg, or about 0.15 mg to about 0.25 mg per puff on the article. Accordingly, the amount of nicotine salt, co-crystal, or salt co-crystal incorporated into the aerosol precursor can be, for example, that amount sufficient to produce these amounts of nicotine when the article is used.

When the nicotine salts, co-crystals, or salt co-crystals described herein are used in electronic smoking articles, the temperature at which nicotine is released into aerosol form from the salt, co-crystal, or salt co-crystal is an important consideration. It is typically important that nicotine is released from the salt, co-crystal, or salt co-crystal (i.e., that the nicotine transfers to aerosol form) at the operating temperature of the electronic smoking articles. Although not intended to be limiting, exemplary operating temperatures of electronic smoking articles are within the range of about 100° C. to about 500° C. (e.g., about 120° C. to about 300° C.). Accordingly, selection of an appropriate nicotine salt, co-crystal, or salt co-crystal for incorporation into such products can depend, in part, on the characteristics of the bond between the nicotine and the coformer and the volatility of the salt, co-crystal, or salt co-crystal. For example, nicotine citrate may not be a good salt for an electronic smoking article because it is not sufficiently volatile.

Furthermore, in some embodiments, the temperature at which the coformer component (or components) is released from a nicotine salt, co-crystal, or salt co-crystal can be a relevant consideration. As it may not be advantageous for certain coformers (e.g., certain acids) to be present in the aerosol (and delivered to the user), it can be important to consider the temperature at which not only the nicotine, but also the coformer of the nicotine salt, co-crystal, or salt co-crystal transfers to aerosol form. In other embodiments, the coformer(s) of a given nicotine salt, co-crystal, or salt co-crystal may be desirably contained in the aerosol and desirably delivered to the user. In such cases, it may be advantageous to ensure that such coformer(s) are sufficiently volatile at the temperature of use of the electronic smoking article. Additionally, any degradation products produced via heating nicotine salts, co-crystals, or salt co-crystals to the relevant temperature (i.e., the typical operation temperature of an electronic smoking article) should also be evaluated and taken into consideration during product preparation and selection for a particular application. In particular, in certain embodiments, acid degradation products produced via heating nicotine salts, co-crystals, or salt co-crystals to the relevant temperature should be evaluated and taken into consideration.

Accordingly, in certain embodiments, following preparation of the nicotine salts, co-crystals, or salt co-crystals described herein, they are analyzed to evaluate whether the nicotine and/or coformer and/or degradation products thereof transfer from the aerosol precursor to the aerosol. Such analysis can be conducted, for example, by high performance liquid chromatography and/or gas chromatography of the condensate collected from the aerosol. Both the presence and amount of nicotine and/or coformer and/or degradation products thereof is evaluated to determine whether a given salt, co-crystal, or salt co-crystal is a good candidate for incorporation within an electronic smoking article.

In still further embodiments, nicotine salts, co-crystals, and/or salt co-crystals disclosed herein may be incorporated within pharmaceutical products. For example, a nicotine salt, co-crystal, or salt co-crystal can be used as a replacement for, or in addition to, the nicotine in nicotine-containing pharmaceutical products. Such products can be used for treatment of a wide variety of conditions, diseases, and disorders responsive to stimulation of one or more types of nicotinic acetylcholinergic receptors (nAChRs). The products can be used to treat those types of conditions, diseases, and disorders that have been reported to be treatable through the use or administration of nicotine as an agonist of nAChRs. As such, the products can be used to treat various CNS conditions, diseases, and disorders, and the compositions also can be used as smoking cessation aids (i.e., as components of NRT). The combined amount of nicotine present (including nicotine present as the salt, co-crystal, and/or salt co-crystal form and, optionally, any one or more other forms of nicotine) is preferably that amount effective to treat some symptoms of, or prevent occurrence of the symptoms of, a condition, disease, or disorder from which the subject or patient suffers. Exemplary conditions, diseases or disorders that can be treated include cognitive disorders such as Alzheimer's disease and attention deficit disorder, schizophrenia, Parkinson's disease, Tourette's syndrome, ulcerative colitis, dry eye disease, hypertension, depression, overactive bladder, obesity, seven year itch/scabies, and hemorrhoids. Such products may also find use as a treatment to reduce stress or pain and/or as a smoking cessation aid.

The shape of the pharmaceutical products can resemble a wide variety of pill, tablet, lozenge, capsule, caplet, pouch and gum types of products that traditionally have been employed for the administration of pharmaceutical types of products. The general nature of a representative composition can be soft or hard to the feel, or of intermediate softness or hardness; and as such, the composition can be considered to be malleable, flexible, chewy, resilient, brittle, or the like. Pharmaceutical products containing nicotine salts, co-crystals, or salt co-crystals as provided herein are not limited to oral products, and such compositions as creams (including salves, ointments, and pastes), liquids (e.g., sprays or enemas), and the like are also encompassed by the present invention as well. In addition, the nicotine salts, co-crystals, and salt co-crystals disclosed herein can also be incorporated within various devices for delivery, such as inhalers (e.g., metered dose inhalers, dry powder inhalers, and nebulizers). Pharmaceutical products according to the present invention can contain, in addition to a nicotine salt, co-crystal, and/or salt co-crystal as described herein, one or more pharmaceutically acceptable components, e.g., excipients (e.g., salts, sweeteners, fillers, flavorants, antiadherents, glidants, preservatives and antioxidants, surfactants, dyes or pigments, lubricants, and/or processing aids). The application as written focuses on the incorporation of novel nicotine salts, co-crystals, and salt co-crystals. However, it is noted that, in some embodiments, known nicotine salts can be employed in compositions disclosed herein to provide novel compositions and/or novel products incorporating such compositions. For example, although not intended to be limiting, known salts such as nicotine L-malate (CAS RN 253180-13-1), nicotine 4-acetamidobenzoic acid salt (CAS RN 110441-65-1), nicotine 3-hydroxybenzoic acid (CAS RN 1644394-41-1, disclosed, for example, in Int. App. Pub. No. WO2015/006652), nicotine 2,5-dihydroxybenzoic acid (CAS RN 6012-21-1), nicotine 4-aminosalicylic acid salt (1-hydroxy-4-amino benzoic acid salt) (CAS RN 20334-41-2), nicotine salicylic acid salt (2-hydroxybenzoic acid salt) (CAS RN 29790-52-1), nicotine phthalic acid salt (1,2-benzene dicarboxylic acid salt) (CAS RN 88660-55-3), nicotine N-acetyl-4-aminosalicylic acid salt (N-acetyl-2-hydroxy-4-aminobenzoic acid salt) (CAS RN 900789-26-6), and/or nicotine di-L-(+)-tartrate dihydrate (CAS RN 6019-06-3) can be used in the compositions and products disclosed herein.

It is further noted that, although the application as written focuses on the formation of nicotine salts, co-crystals, and salt co-crystals and on the incorporation of such formed nicotine salts, co-crystals, and salt co-crystals into various products, it may be possible, in some embodiments, to form such nicotine salts, co-crystals, and salt co-crystals in situ. For example, nicotine can be combined with one or more coformers as broadly described herein, and optionally, other components (e.g., those types of components typically contained in the product to be formed), and a nicotine salt, co-crystal, or salt co-crystal is formed in situ. In other words, although it is often advantageous for reasons disclosed herein, isolation and/or purification of the nicotine salt, co-crystal, or salt co-crystal is not required in all embodiments prior to introduction into a product.

For example, in one embodiment, an aerosol precursor of an electronic smoking article can be prepared by mixing a nicotine salt, co-crystal, or salt co-crystal with desired aerosol precursor components (e.g., carriers and flavorants) or can be prepared by mixing nicotine, a coformer (e.g., an acid), and desired aerosol precursor components. See, for example, the methods of incorporating certain salts into aerosol devices in Int. App. Pub. No. WO2014/182736 to Ploom, Inc., which is incorporated herein by reference.

Aspects of the present invention are more fully illustrated by the following examples, which are set forth to illustrate certain aspects of the present invention and are not to be construed as limiting thereof.

EXPERIMENTAL

General

X-Ray Powder Diffraction (XRPD)

X-Ray Powder Diffraction patterns are collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. A weekly performance check is carried out using a certified standard NIST 1976 Corundum (flat plate). The beam divergence, i.e., the effective size of the X-ray beam on the sample, is approximately 4 mm. A θ-θ continuous scan mode is employed with a sample—detector distance of 20 cm which gives an effective 2θ range of 3.2°-29.7°. Typically the sample is exposed to the X-ray beam for 120 seconds. The software used for data collection is GADDS for XP/2000 4.1.43 and the data are analyzed and presented using Diffrac Plus EVA v13.0.0.2 or v15.0.0.0.

Samples run under ambient conditions are prepared as flat plate specimens of powder, without grinding. Approximately 1-2 mg of the sample is lightly pressed on a glass slide to obtain a flat surface. Samples run under non-ambient conditions are mounted on a silicon wafer with heat-conducting compound. The sample is heated to the appropriate temperature at 20° C./min and subsequently held isothermally for 1 minute before data collection was initiated.

Single Crystal X-Ray Diffraction (SCXRD)

Data are collected on an Oxford Diffraction Supernova Dual Source, Cu at Zero, Atlas CCD diffractometer equipped with an Oxford Cryosystems Cobra cooling device. The data are collected using CuKα radiation. Structures are typically solved using either the SHELXS or SHELXD programs and refined with the SHELXL program as part of the Bruker AXS SHELXTL suite (V6.10). Unless otherwise stated, hydrogen atoms attached to carbon atoms are placed geometrically and allowed to refine with a riding isotropic displacement parameter. Hydrogen atoms attached to a heteroatom are located in a difference Fourier synthesis and are allowed to refine freely with an isotropic displacement parameter.

Example 1

Salts of Nicotine with Mucic Acid

A screening experiment is first conducted to evaluate a solvent free method for the formation of a salt of mucic acid. The required amount of mucic acid (relative to 100 μL nicotine) is weighed into HPLC vials. (S)-Nicotine is dispensed into each vial and the vials are shaken at room temperature for three days. Solids are sampled and characterized by XRPD. As indicated in Table 1, the XRPD analysis results indicate that the solid formed in the vial includes a new crystalline phase form, indicative of the formation of a mucic acid salt.

TABLE 1

XRPD analysis of nicotine mucate

| Stoichiometry (Nicotine:mucic acid) | Form of Product | Results of XRPD Analysis |
|---|---|---|
| 2:1 | Solid | Input acid + new peaks |
| 1:1 | Solid | Input acid + new peaks |
| 1:2 | Solid | Input acid + new peaks |

Various screening experiments were next conducted to evaluate alternative means for the preparation of mucate salts of nicotine, as the slurrying method in neat nicotine was found to be challenging for repetition on a larger scale.

An experiment is conducted to evaluate the preparation of a mucate salt via slow evaporation from water. (S)-Nicotine (100 µL) is dispensed into an HPLC vial along with enough mucic acid to make salts having a 2:1, 1:1, and 1:2 ratio nicotine:mucic acid. Water is added in 100 µL aliquots until a clear solution is obtained or after 2000 µL has been added. The mixture of 2:1 nicotine:mucic acid produced a clear solution after 100 µL of water was added; however, no solid was isolated. The mixtures of 1:1 and 1:2 nicotine:mucic acid are poorly soluble in water and did not produce a clear solution even after the addition of 2000 µL water and these experiments were abandoned.

An experiment is conducted to evaluate the preparation of a mucate salt via antisolvent-mediated salt formation. One equivalent of mucic acid (relative to 100 µL nicotine) is added to an HPLC vial and (S)-nicotine (100 µL) is dispensed into the vial. Ethanol is added in 1 mL aliquots until a clear solution is obtained or after 5 mL has been added. The mixture did not produce a clear solution even after the addition of 5 mL ethanol and this experiment was abandoned.

An experiment is conducted to evaluate the preparation of a mucate salt in tetrahydrofuran (THF). A saturated solution of mucic acid in THF is prepared and filtered prior to use. A portion (2 mL) of this stock solution is added to each of three separate HPLC vials and a given amount of (S)-nicotine is dispensed into each vial (25 µL, 50 µL, or 100 µL). The vials are shaken at room temperature for three days and all three vials contain clear solutions. The solutions are cooled to 4° C. for 24 hours and allowed to evaporate. No solids are formed.

Additional attempts to prepare the mucate salt from ethanol/water and isopropyl alcohol/water systems failed, again due to poor solubility of the acid. An attempt to prepare the mucate salt from DMSO/antisolvent systems also failed to produce the solid mucate salt.

Therefore, to prepare nicotine mucate on a larger scale, mucic acid (5.2 g, 25 mmol) is suspended in (S)-nicotine (10 mL) and stirred at room temperature under argon overnight. To the resulting gummy mixture is added a further 10 mL nicotine and the mixture is stirred for a further 60 h. The solids formed in the mixture are isolated by filtration, washed with cold THF and heptane, and dried. The solid is further slurried in ethyl acetate for 50 hours at room temperature under argon, isolated by filtration, washed with ethyl acetate and heptane, and dried to give a pink solid (7.21 g, 94.2% yield).

The solid is analyzed by various techniques, including XRPD, the pattern of which is shown in FIG. 1. Representative peak listings for the XPRD of nicotine mucate are provided in Table 2.

TABLE 2

XPRD peak listings for nicotine mucate

| Caption | Angle (2-Theta°) | d value (Angstrom) | Intensity (Count) | Intensity (%) |
|---|---|---|---|---|
| 7.072° | 7.072 | 12.48977 | 140 | 3.2 |
| 7.985° | 7.985 | 11.0628 | 1106 | 25.5 |
| 10.879° | 10.879 | 8.12588 | 1340 | 30.9 |
| 12.543° | 12.543 | 7.05143 | 106 | 2.4 |
| 13.028° | 13.028 | 6.78977 | 234 | 5.4 |
| 13.807° | 13.807 | 6.4084 | 349 | 8.1 |
| 14.289° | 14.289 | 6.19336 | 2315 | 53.4 |
| 15.009° | 15.009 | 5.89798 | 2642 | 61 |
| 15.449° | 15.449 | 5.73081 | 2974 | 68.6 |
| 15.851° | 15.851 | 5.5866 | 1487 | 34.3 |
| 16.834° | 16.834 | 5.26237 | 1121 | 25.9 |
| 17.237° | 17.237 | 5.14037 | 811 | 18.7 |
| 18.163° | 18.163 | 4.88041 | 426 | 9.8 |
| 19.660° | 19.66 | 4.51189 | 4333 | 100 |
| 19.930° | 19.93 | 4.45142 | 1130 | 26.1 |
| 20.412° | 20.412 | 4.34734 | 3905 | 90.1 |
| 21.287° | 21.287 | 4.17062 | 404 | 9.3 |
| 21.714° | 21.714 | 4.08949 | 1391 | 32.1 |
| 22.141° | 22.141 | 4.01166 | 1737 | 40.1 |
| 22.455° | 22.455 | 3.95618 | 1021 | 23.6 |
| 22.796° | 22.796 | 3.89791 | 805 | 18.6 |
| 22.986° | 22.986 | 3.86611 | 920 | 21.2 |
| 23.870° | 23.87 | 3.72488 | 1759 | 40.6 |
| 24.614° | 24.614 | 3.61396 | 437 | 10.1 |
| 25.149° | 25.149 | 3.53815 | 130 | 3 |
| 25.642° | 25.642 | 3.47127 | 209 | 4.8 |
| 26.135° | 26.135 | 3.4069 | 714 | 16.5 |
| 26.874° | 26.874 | 3.31492 | 554 | 12.8 |
| 27.212° | 27.212 | 3.27449 | 417 | 9.6 |
| 27.558° | 27.558 | 3.23418 | 707 | 16.3 |
| 27.833° | 27.833 | 3.20282 | 423 | 9.8 |
| 28.202° | 28.202 | 3.16177 | 598 | 13.8 |
| 28.657° | 28.657 | 3.11256 | 256 | 5.9 |
| 29.237° | 29.237 | 3.05217 | 1221 | 28.2 |
| 29.498° | 29.498 | 3.02568 | 739 | 17.1 |
| 30.001° | 30.001 | 2.9761 | 1233 | 28.5 |
| 30.800° | 30.8 | 2.90074 | 1841 | 42.5 |
| 31.855° | 31.855 | 2.807 | 551 | 12.7 |
| 32.525° | 32.525 | 2.75068 | 185 | 4.3 |
| 32.810° | 32.81 | 2.72747 | 265 | 6.1 |
| 33.216° | 33.216 | 2.69505 | 306 | 7.1 |
| 33.611° | 33.611 | 2.66427 | 243 | 5.6 |
| 34.144° | 34.144 | 2.62388 | 504 | 11.6 |
| 34.499° | 34.499 | 2.59766 | 597 | 13.8 |
| 34.999° | 34.999 | 2.56169 | 629 | 14.5 |
| 35.577° | 35.577 | 2.52142 | 290 | 6.7 |
| 36.132° | 36.132 | 2.48392 | 282 | 6.5 |
| 36.724° | 36.724 | 2.44524 | 506 | 11.7 |
| 37.341° | 37.341 | 2.40627 | 533 | 12.3 |
| 37.756° | 37.756 | 2.38072 | 1127 | 26 |
| 39.373° | 39.373 | 2.28663 | 353 | 8.1 |
| 39.853° | 39.853 | 2.26015 | 379 | 8.7 |
| 40.383° | 40.383 | 2.23171 | 311 | 7.2 |
| 41.002° | 41.002 | 2.19948 | 344 | 7.9 |
| 41.326° | 41.326 | 2.18297 | 291 | 6.7 |
| 41.681° | 41.681 | 2.1652 | 275 | 6.3 |
| 41.873° | 41.873 | 2.15568 | 315 | 7.3 |

Figure 2:
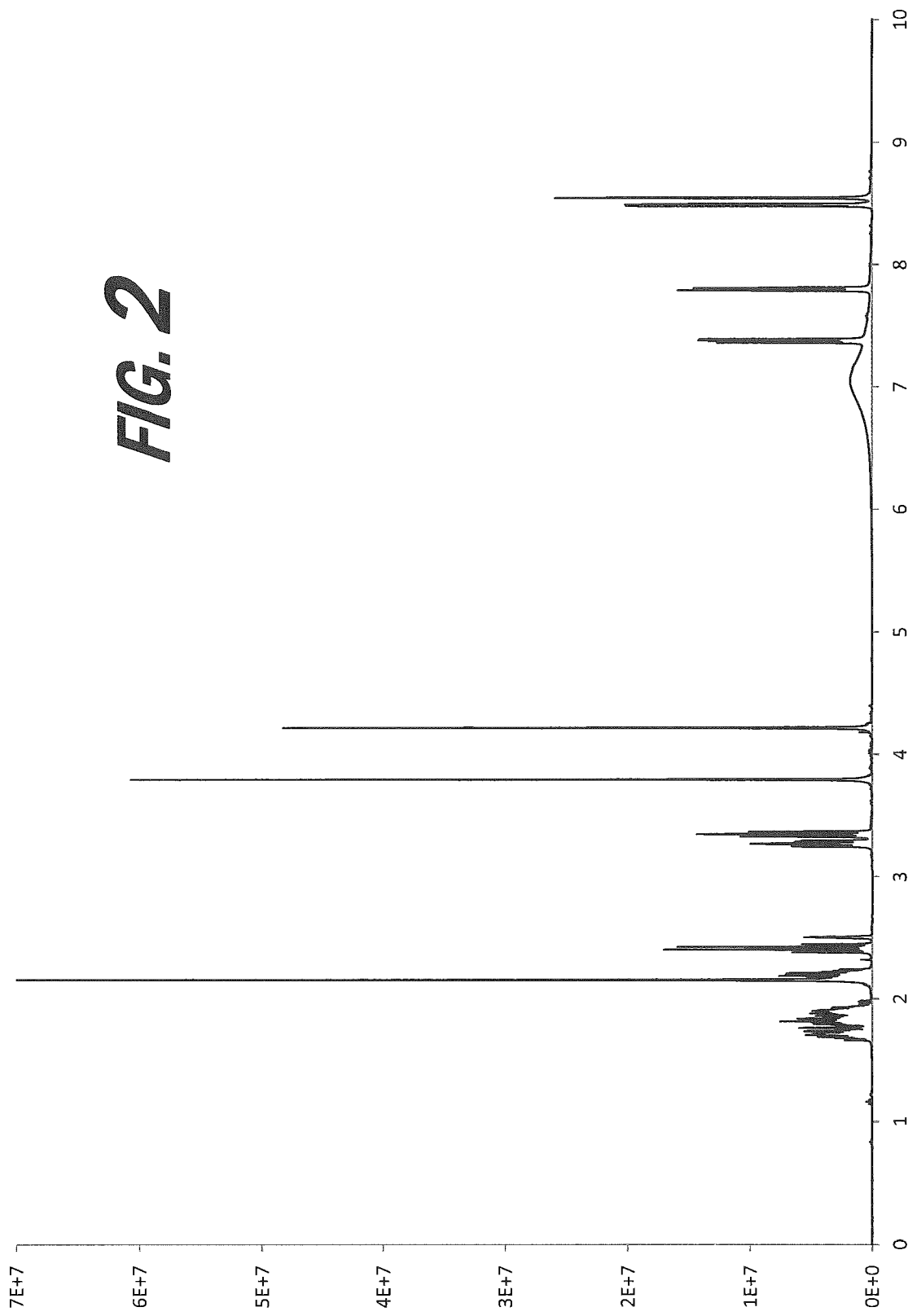
FIG. 2 is a $^1$H NMR spectrum of nicotine mucate.

The sample is further analyzed by methods including $^1$H NMR, as shown in FIG. 2, (indicating that the solid consists of 0.72 equivalents of acid—true stoichiometry of this form is unknown); PLM (indicating irregular birefringent particles, typically <10 µm); TGA (indicating 91% mass loss from 25-260° C. in multiple unresolved steps; DSC (indicating a sharp endotherm onset at 123° C. (73 J/g) and a broad endotherm onset at 133° C. (27 J/g)); and GVS (indicating water uptake of 60% from 0-90% RH, although the actual water uptake is likely higher, as equilibrium was not reached at 90% RH). The solid is rather hygroscopic.

Example 2

Salts of Nicotine with 4-acetamidobenzoic Acid

A screening experiment is first conducted to evaluate a solvent free method for the formation of a salt of 4-acetamidobenzoic acid. 4-Acetamidobenzoic acid (111 mg) is suspended in the minimum amount of (S)-nicotine required to produce a mobile slurry (400 μL). The slurry is shaken at room temperature for 48 hours. Resulting white, powdery solids are isolated by filtration and are sampled and characterized by XRPD, which indicates a new crystalline form.

Screening is next conducted to evaluate alternative means for the preparation of 4-acetamidobenzoate salts of nicotine, as the slurrying method in neat nicotine was found to be challenging for repetition on a larger scale.

An experiment is conducted to evaluate a solvent-based method for the formation of a salt of 4-acetamidobenzoic acid. The 4-acetamidobenzoic acid is dissolved in the minimum amount of THF (400 μL) and (S)-nicotine (1 eq.) is added. The solution is covered and left to stand at room temperature overnight, then at 4° C. for 24 hours and −18° C. for 24 hours. Only trace solids were present in the mixture at each point. The cover is removed and the solvent is allowed to evaporate, giving a crystalline solid. The solid is sampled and characterized by XRPD as a crystalline solid, and the results thereof are consistent with those calculated based on the single crystal structure of nicotine 4-acetamidobenzoate salt (see FIG. 3).

On a larger scale, 4-acetamidobenzoic acid (5.55 g, 31 mmol) is dissolved in THF (280 mL) at room temperature. The slightly cloudy solution is passed through a 0.45 μm PTFE filter and then (S)-nicotine (5 mL, 31 mmol) is added in 1 mL aliquots. The resulting clear solution is stirred at room temperature for 10 minutes and then concentrated to approximately ⅓ its original volume. The solution is seeded with 2 mg of previously prepared nicotine 4-acetamidobenzoate, causing rapid crystallization to occur. The mixture is shaken at room temperature for 5 minutes and allowed to stand for 1 hour. The solid is isolated by filtration, washed with ethyl acetate and heptane, and dried to give 5.42 g white solid (51% yield).

The solid is analyzed by XRPD, the pattern of which is shown in FIG. 3. FIG. 3 compares the experimental XRPD data, obtained at room temperature, against an XRPD pattern calculated from single crystal x-ray data at 100K. Representative peak listings for the (experimental) XRPD of nicotine 4-acetamidobenzoateare are provided in Table 3.

TABLE 3

XPRD peak listings for nicotine 4-acetamidobenzoate

| Caption | Angle (2-Theta°) | d value (Angstrom) | Intensity (Count) | Intensity (%) |
|---|---|---|---|---|
| 4.648° | 4.648 | 18.99512 | 671 | 8.7 |
| 8.876° | 8.876 | 9.95463 | 983 | 12.8 |
| 10.034° | 10.034 | 8.80827 | 903 | 11.7 |
| 13.964° | 13.964 | 6.33687 | 526 | 6.8 |
| 14.472° | 14.472 | 6.11543 | 2032 | 26.4 |
| 15.049° | 15.049 | 5.88254 | 1779 | 23.1 |
| 15.741° | 15.741 | 5.62534 | 305 | 4 |
| 15.945° | 15.945 | 5.55387 | 481 | 6.3 |
| 16.839° | 16.839 | 5.26087 | 3749 | 48.7 |
| 17.346° | 17.346 | 5.10841 | 289 | 3.8 |
| 17.854° | 17.854 | 4.96415 | 7695 | 100 |
| 18.628° | 18.628 | 4.7595 | 928 | 12.1 |
| 20.134° | 20.134 | 4.40667 | 6451 | 83.8 |
| 20.438° | 20.438 | 4.34193 | 1282 | 16.7 |
| 20.733° | 20.733 | 4.28088 | 1033 | 13.4 |
| 21.288° | 21.288 | 4.17039 | 1956 | 25.4 |
| 22.516° | 22.516 | 3.94566 | 329 | 4.3 |
| 22.739° | 22.739 | 3.90742 | 530 | 6.9 |
| 23.265° | 23.265 | 3.82026 | 3867 | 50.3 |
| 23.661° | 23.661 | 3.75728 | 1622 | 21.1 |
| 24.268° | 24.268 | 3.66459 | 373 | 4.8 |
| 24.798° | 24.798 | 3.58754 | 786 | 10.2 |
| 25.408° | 25.408 | 3.50272 | 616 | 8 |
| 25.720° | 25.72 | 3.46098 | 420 | 5.5 |
| 26.077° | 26.077 | 3.41442 | 216 | 2.8 |
| 26.864° | 26.864 | 3.31606 | 1298 | 16.9 |
| 27.322° | 27.322 | 3.26157 | 212 | 2.8 |
| 27.633° | 27.633 | 3.22553 | 233 | 3 |
| 27.878° | 27.878 | 3.1977 | 730 | 9.5 |
| 28.228° | 28.228 | 3.15892 | 1077 | 14 |
| 28.544° | 28.544 | 3.12464 | 683 | 8.9 |
| 28.882° | 28.882 | 3.0888 | 299 | 3.9 |
| 29.189° | 29.189 | 3.05699 | 839 | 10.9 |
| 30.051° | 30.051 | 2.97131 | 168 | 2.2 |
| 30.473° | 30.473 | 2.93113 | 606 | 7.9 |
| 30.818° | 30.818 | 2.89909 | 677 | 8.8 |
| 31.745° | 31.745 | 2.81647 | 321 | 4.2 |
| 32.221° | 32.221 | 2.77598 | 281 | 3.7 |
| 32.501° | 32.501 | 2.75266 | 419 | 5.4 |
| 33.466° | 33.466 | 2.67545 | 261 | 3.4 |
| 33.909° | 33.909 | 2.64149 | 257 | 3.3 |
| 34.456° | 34.456 | 2.60081 | 265 | 3.4 |
| 34.995° | 34.995 | 2.56197 | 246 | 3.2 |
| 35.655° | 35.655 | 2.51608 | 150 | 1.9 |
| 36.128° | 36.128 | 2.48423 | 190 | 2.5 |
| 36.527° | 36.527 | 2.45796 | 235 | 3.1 |
| 37.342° | 37.342 | 2.40618 | 194 | 2.5 |
| 37.766° | 37.766 | 2.38014 | 359 | 4.7 |
| 38.199° | 38.199 | 2.35413 | 361 | 4.7 |
| 39.177° | 39.177 | 2.2976 | 445 | 5.8 |
| 39.579° | 39.579 | 2.27516 | 415 | 5.4 |
| 40.298° | 40.298 | 2.23621 | 485 | 6.3 |
| 41.539° | 41.539 | 2.17224 | 189 | 2.5 |

The solid is further analyzed by various techniques, including $^1$H NMR (indicating that the solid consists of 1.04 equivalents of acid); PLM (indicating irregular birefringent laths up to 75 μm in length); TGA (indicating 64% mass loss from 25-360° C. in two unresolved steps); DSC (indicating a sharp endotherm onset at 134° C. (151 J/g) and a broad endotherm onset at 143° C. (43 J/g)); and GVS (indicating water uptake of 5% from 0-80% RH and 20% from 80-90% RH). XRPD analysis following GVS indicates that the solid is unchanged.

Figure 4C:
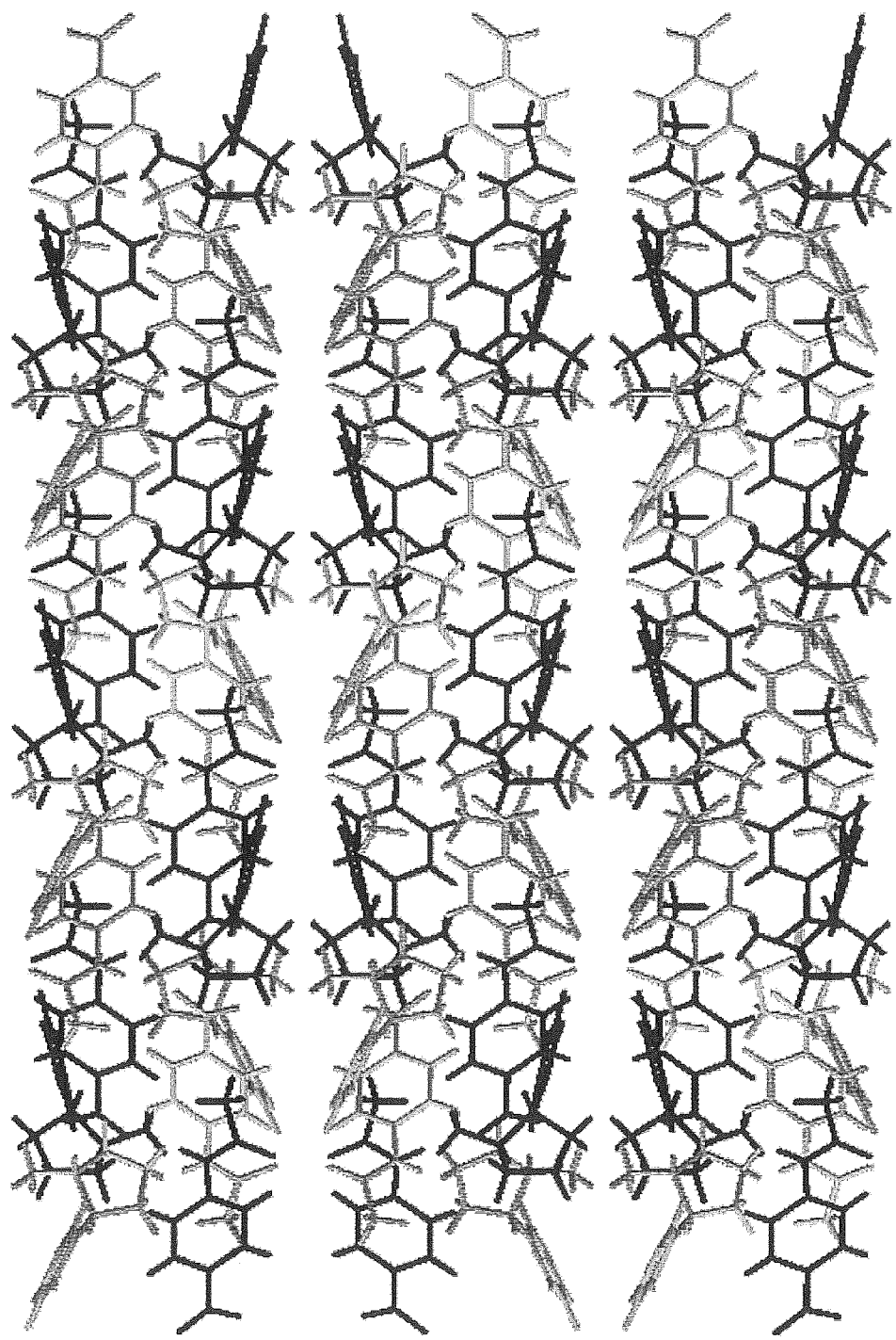

Crystal structures obtained for two independent molecules of nicotine 4-acetamidobenzoate are shown in FIGS. 4A and 4B. The crystal packing of the nicotine 4-acetamidobenzoate obtained is provided in FIG. 4C, wherein nicotine molecules are shown in grey and acid molecules are shown in black.

Crystallographic parameters for the isolated form are provided in Table 4. The structure solution was obtained by direct methods, full-matrix least-squares refinement on $F^2$ with weighting $w^{-1}=\sigma_2(F_o^2)+(0.0575P)^2+(1.5000P)$, where $P=(F_o^2+2F_c^2)/3$, anisotropic displacement parameters. Empirical absorption correction using spherical harmonics, implemented in SCALE3 ABSPACK scaling algorithm. Absolute structure parameter=0.04(16) (Also known as the Flack parameter, this should be approximately zero for the correct absolute stereochemistry, and approximately unity for the inverted absolute structure (within the standard uncertainty). Cf. Flack H D (1983), *Acta Cryst*. A39, 876-

881). The SCXRD structure provided confirmation that the nicotine has S absolute stereochemistry. Final $wR^2=\{\Sigma[w(F_o^2-F_c^2)^2]/\Sigma[w(F_o^2)^2]^{1/2}\}=0.0976$ for all data, conventional $R_1=0.0356$ on F values of 6624 reflections with $F_o>4\sigma(F_o)$, S=1.001 for all data and 471 parameters. Final $\Delta/\sigma$(max) 0.000, $\Delta/\sigma$(mean), 0.000. Final difference map between +0.193 and −0.207 e Å$^{-3}$.

TABLE 4

Crystallographic parameters for nicotine 4-acetamidobenzoate

| | |
|---|---|
| Molecular formula | $C_{19}H_{23}N_3O_3$ |
| Molecular weight | 341.4 |
| Crystal system | Monoclinic |
| Space group | C2  a  19.6640(10) Å, α  90°, |
| | b  12.6374(8) Å,  β  96.063(5)°, |
| | c  14.2489(8) Å,  γ  90° |
| V | 3521.1(3) Å$^3$ |
| Z | 8 |
| $D_c$ | 1.288 g · cm$^{-3}$ |
| μ | 0.717 mm$^{-1}$ |
| Source, λ | Cu—K(alpha), 1.54178 Å |
| F(000) | 1456 |
| T | 100(1) K |
| Crystal | Colorless prism, 0.18 × 0.1 × 0.07 mm |
| Data truncated to | 0.80 Å |
| $\theta_{max}$ | 74.47° |
| Completeness | 99.5% |
| Reflections | 17816 |
| Unique reflections | 7005 |
| $R_{int}$ | 0.0227 |
| Abs. Struct. Para. | 0.04(16) |

Example 3

Salts of Nicotine with Gentisic (2,5-hydroxybenzoic) Acid

A screening experiment is first conducted to evaluate a solvent free method for the formation of a salt of gentisic acid. Gentisic acid (95 mg) is suspended in the minimum amount of (S)-nicotine required to produce a mobile slurry (200 μL). The slurry is shaken at room temperature for 48 hours. Resulting pinkish solids are isolated by filtration and are sampled and characterized by XRPD, which indicates a new crystalline form.

An experiment is conducted to evaluate a solvent-based method for the formation of a salt of gentisic acid. The gentisic acid is dissolved in the minimum amount of THF (200 μL) and (S)-nicotine (1 eq.) is added. The solution is covered and left to stand at room temperature overnight, then at 4° C. for 24 hours and −18° C. for 24 hours. A clear solution was present in the mixture at each point. The cover is removed and the solvent is allowed to evaporate, but resulted in no isolated solid.

On a larger scale, gentisic acid (4.75 g, 31 mmol) is dissolved in THF (50 mL) at room temperature. (S)-Nicotine (5 mL, 31 mmol) is added in 1 mL aliquots and the resulting clear solution is stirred at room temperature for 10 minutes. The solution is seeded with 2 mg of previously prepared nicotine gentisate, causing rapid crystallization to occur and the mixture is stirred at room temperature for 10 minutes. The solid is isolated by filtration, washed with cold THF and heptane, and dried to give 7.20 g white solid (74% yield).

The solid is analyzed by XRPD, the pattern of which is shown in FIG. 5. FIG. 5 compares the experimental XRPD data, obtained at room temperature, against an XRPD pattern calculated from single crystal x-ray data at 100K. Representative peak listings for the (experimental) XPRD of nicotine gentisate are provided in Table 5.

TABLE 5

XPRD peak listings for nicotine gentisate

| Caption | Angle (2-Theta°) | d value (Angstrom) | Intensity (Count) | Intensity (%) |
|---|---|---|---|---|
| 10.212° | 10.212 | 8.65523 | 277 | 3.4 |
| 11.663° | 11.663 | 7.58125 | 1668 | 20.4 |
| 12.243° | 12.243 | 7.22334 | 902 | 11 |
| 13.000° | 13 | 6.80452 | 3280 | 40 |
| 14.127° | 14.127 | 6.26419 | 178 | 2.2 |
| 14.608° | 14.608 | 6.05916 | 1682 | 20.5 |
| 18.273° | 18.273 | 4.85113 | 2192 | 26.7 |
| 19.017° | 19.017 | 4.66305 | 8195 | 100 |
| 19.393° | 19.393 | 4.57338 | 2090 | 25.5 |
| 19.968° | 19.968 | 4.44301 | 1368 | 16.7 |
| 20.194° | 20.194 | 4.39387 | 3896 | 47.5 |
| 20.551° | 20.551 | 4.3183 | 952 | 11.6 |
| 21.000° | 21 | 4.22689 | 4159 | 50.8 |
| 22.096° | 22.096 | 4.01964 | 2474 | 30.2 |
| 23.080° | 23.08 | 3.85046 | 275 | 3.4 |
| 23.407° | 23.407 | 3.79738 | 867 | 10.6 |
| 24.385° | 24.385 | 3.64735 | 573 | 7 |
| 24.615° | 24.615 | 3.61376 | 1518 | 18.5 |
| 25.231° | 25.231 | 3.52691 | 1904 | 23.2 |
| 25.884° | 25.884 | 3.43935 | 902 | 11 |
| 26.191° | 26.191 | 3.39982 | 4509 | 55 |
| 26.837° | 26.837 | 3.31935 | 1327 | 16.2 |
| 27.133° | 27.133 | 3.28378 | 390 | 4.8 |
| 28.545° | 28.545 | 3.12455 | 362 | 4.4 |
| 30.390° | 30.39 | 2.93891 | 897 | 10.9 |
| 31.056° | 31.056 | 2.87737 | 1361 | 16.6 |
| 31.855° | 31.855 | 2.80696 | 1458 | 17.8 |
| 32.241° | 32.241 | 2.77428 | 303 | 3.7 |
| 33.375° | 33.375 | 2.68254 | 368 | 4.5 |
| 33.825° | 33.825 | 2.64785 | 187 | 2.3 |
| 34.452° | 34.452 | 2.60111 | 205 | 2.5 |
| 34.712° | 34.712 | 2.58224 | 257 | 3.1 |
| 35.111° | 35.111 | 2.55381 | 417 | 5.1 |
| 36.392° | 36.392 | 2.46677 | 198 | 2.4 |
| 36.742° | 36.742 | 2.44411 | 215 | 2.6 |
| 37.007° | 37.007 | 2.42721 | 174 | 2.1 |
| 37.349° | 37.349 | 2.40576 | 524 | 6.4 |
| 37.869° | 37.869 | 2.37391 | 375 | 4.6 |
| 38.193° | 38.193 | 2.35451 | 541 | 6.6 |
| 38.592° | 38.592 | 2.33106 | 143 | 1.7 |
| 39.651° | 39.651 | 2.27124 | 501 | 6.1 |
| 40.271° | 40.271 | 2.23769 | 190 | 2.3 |
| 40.793° | 40.793 | 2.21022 | 510 | 6.2 |
| 41.644° | 41.644 | 2.16701 | 404 | 4.9 |

The solid is further analyzed by various techniques, including $^1$H NMR (indicating that the solid consists of 1.00 equivalents of acid); PLM (indicating irregular birefringent laths up to 100 μm in length); TGA (indicating 95% mass loss from 25-280° C.); DSC (indicating a sharp endotherm onset at 149° C. (102 J/g)); and GVS (indicating water uptake of 0.3% from 0-90% RH). XRPD analysis following GVS indicates that the solid is unchanged. The gentisic acid salt compares well to commercially available nicotine ditartrate dihydrate in terms of thermal stability.

A crystal structure obtained for a molecule of nicotine gentisate is shown in FIG. 6A. The crystal packing of the nicotine gentisate obtained is provided in FIG. 6B, wherein nicotine molecules are shown in grey and acid molecules are shown in black.

Crystallographic parameters for the isolated form are provided below in Table 6. The structure solution was obtained by direct methods, full-matrix least-squares refinement on $F^2$ with weighting $w^{-1}=s^2(F_o^2)+(0.0720P)^2+(0.0060P)$, where $P=(F_o^2+2F_c^2)/3$, anisotropic displacement parameters. Empirical absorption correction using spherical harmonics, implemented in SCALE3 ABSPACK scaling algorithm. Absolute structure parameter=0.4(3). Final $wR^2=\{S[w(F_o^2-F_c^2)^2]/S[w(F_o^2)^2]^{1/2}\}=0.1342$, for all data, conventional $R_1=0.0472$ on F values of 2025 reflections with $F_o>4s(F_o)$, $S=1.004$ for all data and 221 parameters. Final D/s(max) 0.000, D/s(mean), 0.000. Final difference map between +0.173 and −0.219 e Å$^{-3}$.

Collected data was not suitable for determination of the absolute configuration, so the stereochemistry of the nicotine moiety was fixed as per the input material and as per the structure determined in Example 2 (i.e., with the S enantiomer of nicotine).

TABLE 6

Crystallographic parameters for nicotine 2,5-dihydroxybenzoate

| | |
|---|---|
| Molecular formula | $C_{17}H_{20}N_2O_4$ |
| Molecular weight | 316.35 |
| Crystal system | Monoclinic |
| Space group | $P2_1$  A  8.1984(7) Å,  α  90°, |
| | B  10.9394(9) Å,  β  112.589(11)°, |
| | C  9.2257(9) Å  γ  90°, |
| V | 763.94(13) Å$^3$ |
| Z | 2 |
| $D_c$ | 1.375 g · cm$^{-3}$ |
| μ | 0.812 mm$^{-1}$ |
| Source, λ | Cu—K(alpha), 1.54178 Å |
| F(000) | 336 |
| T | 100(1) K |
| Crystal | colorless plate, 0.10 × 0.05 × 0.02 mm, |
| Data truncated to | 0.80 Å |
| $θ_{max}$ | 26.37° |
| Completeness | 99.5% |
| Reflections | 12079 |
| Unique reflections | 6914 |
| $R_{int}$ | 0.0778 |
| Abs. Struct. Para. | 0.4(3) |

Example 4

Salts of Nicotine with 3-hydroxybenzoic Acid

A screening experiment is first conducted to evaluate a solvent free method for the formation of a salt of 3-hydroxybenzoic acid. 3-Hydroxybenzoic acid (85 mg) is suspended in the minimum amount of (S)-nicotine required to produce a mobile slurry (200 μL). The slurry is shaken at room temperature for 48 hours. The resulting gum is sampled and characterized by XRPD (showing that the sample deliquesced).

On a larger scale, 3-hydroxybenzoic acid (4.25 g, 31 mmol) is dissolved in THF (50 mL) at room temperature by stirring for 10 minutes. (S)-Nicotine (5 mL, 31 mmol) is added in 1 mL aliquots with constant stirring and the resulting clear solution is stirred at room temperature for 10 minutes. The solution is seeded with 2 mg of previously prepared nicotine 3-hydroxybenzoate, causing rapid crystallization to occur and the mixture is stirred at room temperature for 1 hour. The solid is isolated by filtration, washed with cold THF and heptane, and dried to give 4.81 g white solid (52% yield).

Figure 7:
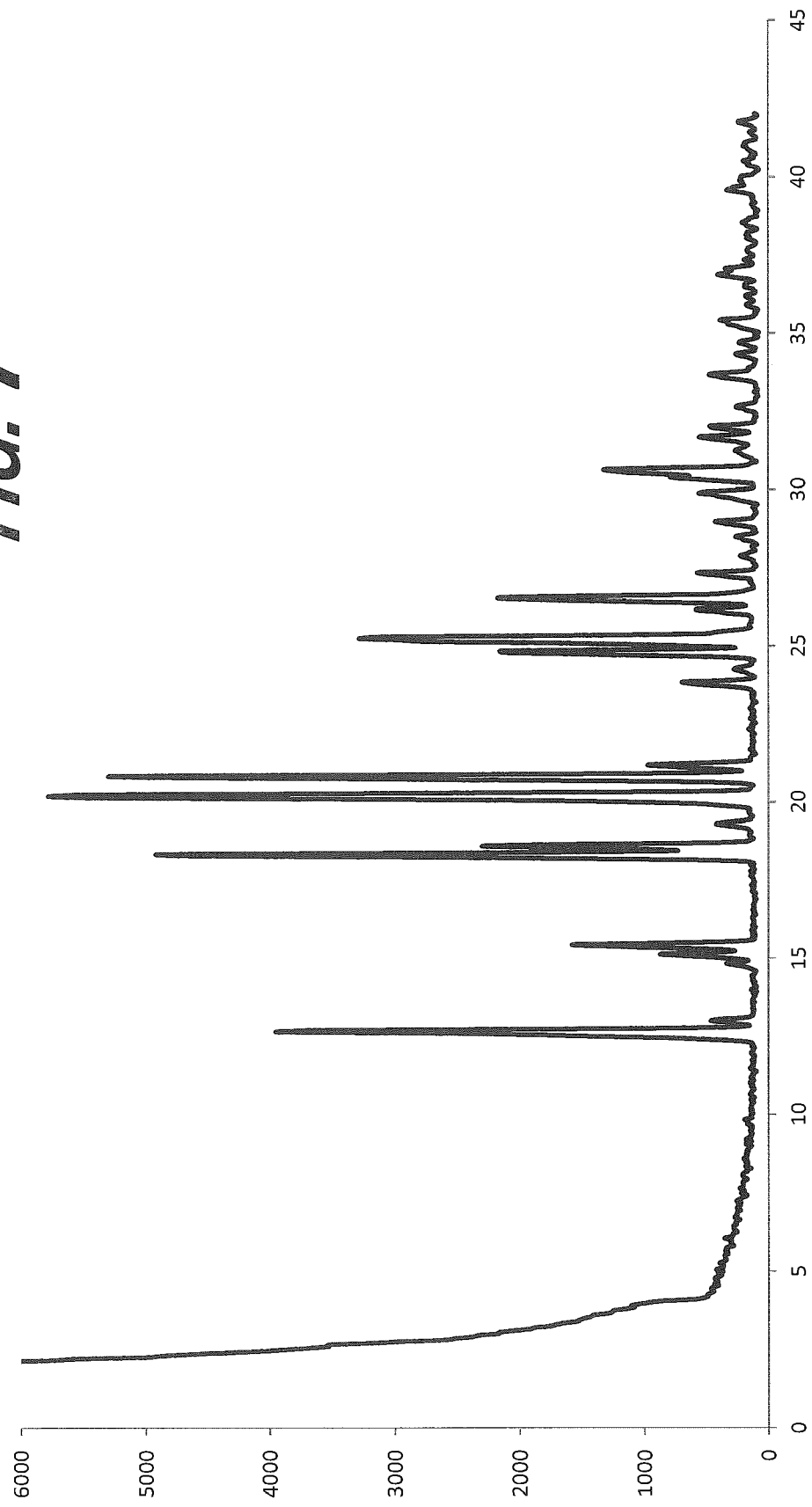
FIG. 7 is an x-ray powder diffraction pattern of nicotine 3-hydroxybenzoate.

The solid is analyzed by XRPD, the pattern of which is shown in FIG. 7. Representative peak listings for the XPRD of nicotine 3-hydroxybenzoate are provided in Table 7.

TABLE 7

XPRD peak listings for nicotine 3-hydroxybenzoate

| Caption | Angle (2-Theta°) | d value (Angstrom) | Intensity (Count) | Intensity (%) |
|---|---|---|---|---|
| 12.655° | 12.655 | 6.98936 | 3944 | 68.2 |
| 12.994° | 12.994 | 6.80778 | 459 | 7.9 |
| 14.792° | 14.792 | 5.98419 | 332 | 5.7 |
| 15.143° | 15.143 | 5.84607 | 860 | 14.9 |
| 15.394° | 15.394 | 5.75143 | 1564 | 27.1 |
| 18.324° | 18.324 | 4.8377 | 4891 | 84.6 |
| 18.591° | 18.591 | 4.76894 | 2301 | 39.8 |
| 19.304° | 19.304 | 4.59425 | 417 | 7.2 |
| 20.186° | 20.186 | 4.39555 | 5781 | 100 |
| 20.814° | 20.814 | 4.26426 | 5235 | 90.6 |
| 21.150° | 21.15 | 4.1974 | 967 | 16.7 |
| 23.810° | 23.81 | 3.73403 | 686 | 11.9 |
| 24.265° | 24.265 | 3.66505 | 273 | 4.7 |
| 24.796° | 24.796 | 3.58772 | 2158 | 37.3 |
| 25.216° | 25.216 | 3.52901 | 3287 | 56.9 |
| 26.155° | 26.155 | 3.4044 | 576 | 10 |
| 26.494° | 26.494 | 3.36162 | 2164 | 37.4 |
| 27.303° | 27.303 | 3.26382 | 562 | 9.7 |
| 27.865° | 27.865 | 3.19919 | 221 | 3.8 |
| 28.466° | 28.466 | 3.13305 | 261 | 4.5 |
| 28.967° | 28.967 | 3.07994 | 418 | 7.2 |
| 29.874° | 29.874 | 2.9885 | 556 | 9.6 |
| 30.331° | 30.331 | 2.94445 | 786 | 13.6 |
| 30.604° | 30.604 | 2.91886 | 1324 | 22.9 |
| 31.235° | 31.235 | 2.86129 | 263 | 4.5 |
| 31.678° | 31.678 | 2.82231 | 549 | 9.5 |
| 32.000° | 32 | 2.79461 | 464 | 8 |
| 32.650° | 32.65 | 2.74042 | 255 | 4.4 |
| 33.667° | 33.667 | 2.65992 | 466 | 8.1 |
| 34.283° | 34.283 | 2.61358 | 258 | 4.5 |
| 34.700° | 34.7 | 2.58309 | 229 | 4 |
| 35.367° | 35.367 | 2.53587 | 380 | 6.6 |
| 35.868° | 35.868 | 2.50164 | 167 | 2.9 |
| 36.176° | 36.176 | 2.48103 | 176 | 3 |
| 36.547° | 36.547 | 2.45667 | 183 | 3.2 |
| 36.885° | 36.885 | 2.43495 | 402 | 7 |
| 37.377° | 37.377 | 2.40403 | 187 | 3.2 |
| 37.654° | 37.654 | 2.38696 | 164 | 2.8 |
| 38.101° | 38.101 | 2.35996 | 171 | 3 |
| 38.509° | 38.509 | 2.3359 | 203 | 3.5 |
| 39.080° | 39.08 | 2.3031 | 128 | 2.2 |
| 39.625° | 39.625 | 2.27266 | 327 | 5.7 |
| 39.960° | 39.96 | 2.25439 | 217 | 3.8 |
| 40.481° | 40.481 | 2.22654 | 193 | 3.3 |
| 41.024° | 41.024 | 2.1983 | 198 | 3.4 |
| 41.425° | 41.425 | 2.17798 | 146 | 2.5 |
| 41.762° | 41.762 | 2.16119 | 234 | 4 |

The solid is further analyzed by various techniques, including $^1$H NMR (indicating that the solid consists of 1.03 equivalents of acid); PLM (indicating irregular sharp edged particles); TGA (indicating 89% mass loss from 25-360° C. in two unresolved steps); DSC (indicating a sharp endotherm onset at 123° C. (131 J/g)); and GVS (indicating water uptake of 0.5% from 0-80% RH and 5% from 80-90% RH). XRPD analysis following GVS indicates that the solid is unchanged.

Example 5

Salts of Nicotine with L-malic Acid

A screening experiment is first conducted to evaluate a solvent free method for the formation of a salt of L-malic acid. The required amount of L-malic acid (relative to 100 μL nicotine) is weighed into HPLC vials in 2:1, 1:1, and 1:2 ratios of nicotine:acid. (S)-Nicotine is dispensed into each vial and the vials are shaken at room temperature for three days. Solids are sampled and characterized by XRPD.

An experiment is conducted to evaluate the preparation of a L-malic acid salt via slow evaporation from water. (S)-

Nicotine (100 μL) is dispensed into an HPLC vial along with enough mucic acid to make salts having a 2:1, 1:1, and 1:2 ratio nicotine:L-malic acid. Water is added in 100 μL aliquots until a clear solution is obtained or after 2000 μL has been added. All mixtures of nicotine and L-malic acid produced a clear solution after 200 μL of water was added; however, no solid was isolated.

An experiment is conducted to evaluate the preparation of a L-malate salt via antisolvent-mediated salt formation. One equivalent of L-malic acid (relative to 100 μL nicotine) is added to an HPLC vial and (S)-nicotine (100 μL) is dispensed into the vial.

Ethanol is added in 1 mL aliquots until a clear solution is obtained or after 5 mL has been added. After the addition of 2000 μL of ethanol, a clear solution was afforded. EtOAc was then added in 1 mL portions until either persistent cloudiness was noted or 10 mL had been added. After the addition of 3000 μL, a material was noted to be oiling out. The mixture was placed at 4° C. overnight and, after this time, was observed to be a sticky gum. The mixture was then placed at −18° C. for a week and, after this time, was observed to be a sticky gum. The gum was placed in an incubator and maturated between ambient temperature and 50° C. at 8 h intervals for a period of 1 week, after which time the mixture appeared to be a viscous solution.

An experiment is conducted to evaluate the preparation of an L-malate salt by freeze drying and subsequent maturation. Stock solutions are prepared by combining (S)-nicotine (120 μL) with one equivalent of the acid in water (12 mL). The solution is shaken at room temperature to give a clear homogenous phase. A portion of the relevant stock solution (1 mL) is dispensed into each of 10 vials, which are frozen and lyophilized overnight to remove water. An aliquot of maturation solvent (100 μL of acetone, EtOH, IPA, toluene, dioxane, IPAc, TBME, acetone+5% water, EtOH+5% water, IPA+5% water) is added to each vial and the vials are shaken at room temperature for 4 days. The vial containing IPA provided a solid malate salt as determined by XRPD. The vials containing IPAc and TBME were observed to comprise an oil/gum; all other vials were observed to comprise clear solutions.

To prepare nicotine L-malate on a larger scale, malic acid (2.84 g, 21 mmol) is dissolved in THF (30 mL) by stirring for 10 minutes at room temperature. (S)-Nicotine (5.0 mL, 31 mmol) is added, causing instant precipitation of a white solid. The slurry is seeded with 2 mg previously-prepared nicotine L-malate and stirred at room temperature overnight. The solids formed in the mixture are isolated by filtration, washed with cold THF and heptane, and dried to give a white solid (5.78 g, 92% yield).

Figure 8:
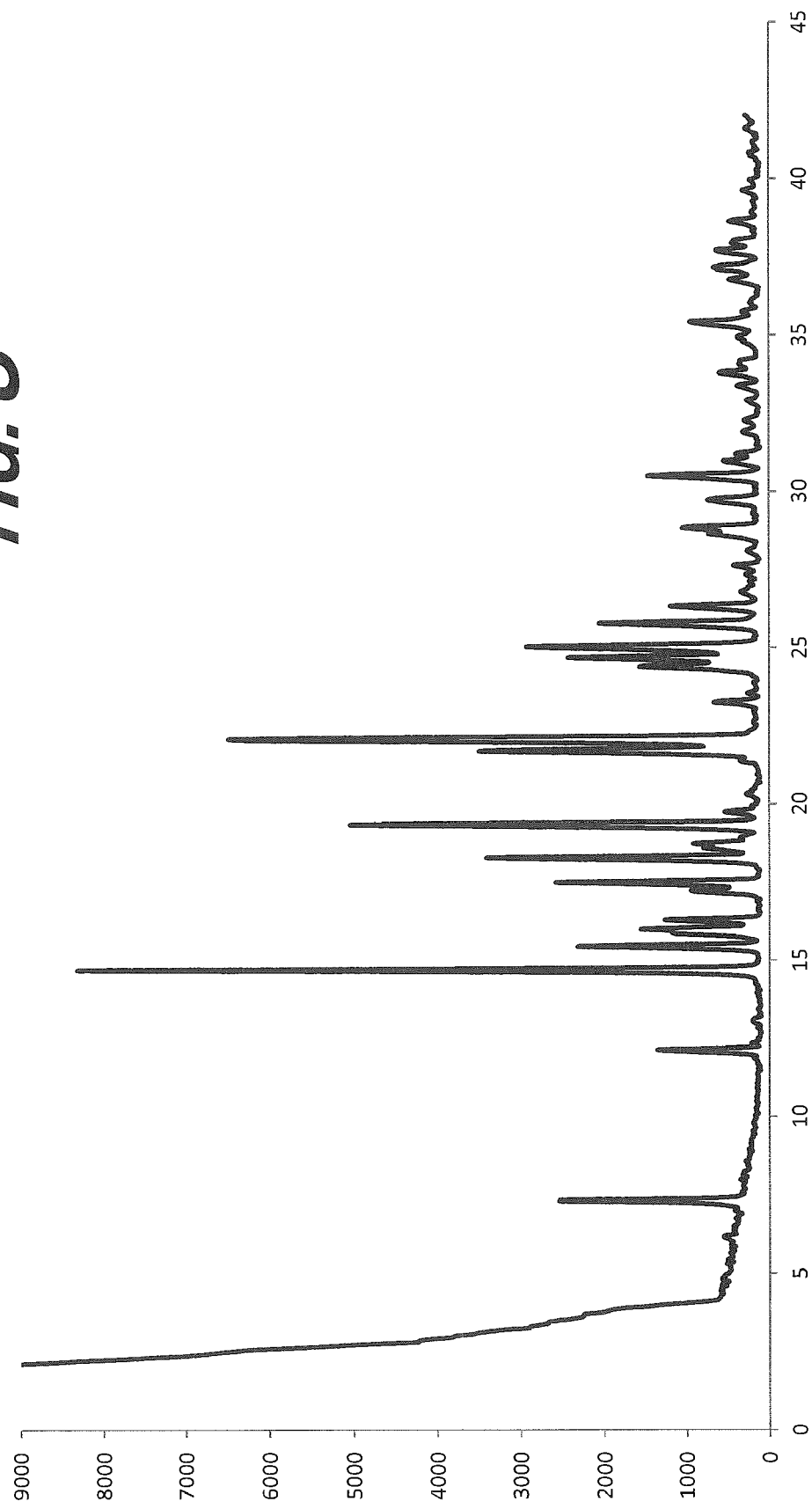
FIG. 8 is an x-ray powder diffraction pattern of nicotine malate.

The solid is analyzed by XRPD, the pattern of which is shown in FIG. 8. Representative peak listings for the XRPD of nicotine L-malate are provided in Table 8.

TABLE 8

XPRD peak listings for nicotine L-malate

| Caption | Angle (2-Theta°) | d value (Angstrom) | Intensity (Count) | Intensity (%) |
|---|---|---|---|---|
| 6.128° | 6.128 | 14.41077 | 546 | 6.6 |
| 7.343° | 7.343 | 12.0284 | 2526 | 30.4 |
| 12.147° | 12.147 | 7.28016 | 1328 | 16 |
| 13.082° | 13.082 | 6.76194 | 197 | 2.4 |
| 14.671° | 14.671 | 6.0332 | 8306 | 100 |
| 15.444° | 15.444 | 5.73289 | 2296 | 27.6 |
| 15.957° | 15.957 | 5.54959 | 1551 | 18.7 |

TABLE 8-continued

XPRD peak listings for nicotine L-malate

| Caption | Angle (2-Theta°) | d value (Angstrom) | Intensity (Count) | Intensity (%) |
|---|---|---|---|---|
| 16.238° | 16.238 | 5.45436 | 1243 | 15 |
| 17.237° | 17.237 | 5.1402 | 937 | 11.3 |
| 17.462° | 17.462 | 5.0747 | 2565 | 30.9 |
| 18.243° | 18.243 | 4.85897 | 3377 | 40.7 |
| 18.594° | 18.594 | 4.7681 | 843.8 | 10.2 |
| 18.710° | 18.71 | 4.73894 | 912 | 11 |
| 19.326° | 19.326 | 4.58921 | 5039 | 60.7 |
| 19.736° | 19.736 | 4.49465 | 528 | 6.4 |
| 20.308° | 20.308 | 4.36932 | 269 | 3.2 |
| 21.395° | 21.395 | 4.14979 | 406 | 4.9 |
| 21.713° | 21.713 | 4.08969 | 3481 | 41.9 |
| 22.049° | 22.049 | 4.0282 | 6470 | 77.9 |
| 23.256° | 23.256 | 3.82176 | 655 | 7.9 |
| 23.586° | 23.586 | 3.76907 | 260 | 3.1 |
| 24.404° | 24.404 | 3.6445 | 1566 | 18.9 |
| 24.652° | 24.652 | 3.6084 | 2414 | 29.1 |
| 24.999° | 24.999 | 3.55907 | 2912 | 35.1 |
| 25.759° | 25.759 | 3.45584 | 2057 | 24.8 |
| 26.302° | 26.302 | 3.38568 | 1188 | 14.3 |
| 26.764° | 26.764 | 3.32829 | 340 | 4.1 |
| 27.303° | 27.303 | 3.26373 | 281 | 3.4 |
| 27.632° | 27.632 | 3.22571 | 419 | 5 |
| 28.097° | 28.097 | 3.17334 | 259 | 3.1 |
| 28.636° | 28.636 | 3.11478 | 724 | 8.7 |
| 28.830° | 28.83 | 3.09429 | 1045 | 12.6 |
| 29.712° | 29.712 | 3.00437 | 731 | 8.8 |
| 30.476° | 30.476 | 2.93084 | 1466 | 17.6 |
| 30.965° | 30.965 | 2.88562 | 533 | 6.4 |
| 31.231° | 31.231 | 2.86168 | 395 | 4.8 |
| 31.928° | 31.928 | 2.80076 | 310 | 3.7 |
| 32.266° | 32.266 | 2.77221 | 296 | 3.6 |
| 32.901° | 32.901 | 2.72014 | 261 | 3.1 |
| 33.362° | 33.362 | 2.68357 | 379 | 4.6 |
| 33.784° | 33.784 | 2.65102 | 587 | 7.1 |
| 34.096° | 34.096 | 2.62746 | 358 | 4.3 |
| 34.928° | 34.928 | 2.56677 | 375 | 4.5 |
| 35.394° | 35.394 | 2.534 | 943 | 11.4 |
| 35.778° | 35.778 | 2.50772 | 320 | 3.9 |
| 36.037° | 36.037 | 2.49025 | 224 | 2.7 |
| 36.762° | 36.762 | 2.44282 | 469 | 5.6 |
| 37.168° | 37.168 | 2.41704 | 654 | 7.9 |
| 37.677° | 37.677 | 2.38558 | 622 | 7.5 |
| 37.960° | 37.96 | 2.36839 | 439 | 5.3 |
| 38.625° | 38.625 | 2.32916 | 468 | 5.6 |
| 39.599° | 39.599 | 2.27409 | 315 | 3.8 |
| 39.951° | 39.951 | 2.25488 | 226 | 2.7 |
| 40.808° | 40.808 | 2.20948 | 237 | 2.9 |
| 41.183° | 41.183 | 2.19021 | 193 | 2.3 |
| 41.591° | 41.591 | 2.16965 | 279 | 3.4 |

The solid is further analyzed by various techniques, including $^1$H NMR (indicating that the solid consists of 1.07 equivalents of acid); PLM (indicating irregular birefringent particles typically <25 μm); TGA (indicating 91% mass loss from 25-260° C.); DSC (indicating a small endotherm onset at 107° C. (1 J/g), a sharp endotherm onset at 120° C. (120 J/g), and a broad endotherm onset at 168° C. (452 J/g)); and GVS (indicating water uptake of 70% from 0-90% RH, although the actual water uptake was likely actually higher, as equilibrium was not reached at 90% RH). The small endotherm onset may be possible evidence of the existence of a second polymorph. XRPD analysis following GVS indicates that the solid deliquesced.

Example 6

Salts of Nicotine with 3,5-dihydroxybenzoic Acid

A screening experiment is first conducted to evaluate the formation of a nicotine salt with 3,5-dihydroxybenzoic acid by crystallization from neat nicotine. 3,5-Dihydroxybenzoic acid (25 mg) is combined with (S)-nicotine (100 µL) and the mixture is shaken at room temperature overnight. The 3,5-dihydroxybenzoic acid dissolves in the nicotine; no solid is observed.

An experiment is conducted to evaluate the preparation of a 3,5-dihydroxybenzoic acid salt via crystallization from THF. 3,5-Dihydroxybenzoic acid (~40 mg) is dispensed into a vial and THF is added in aliquots, with brief vortexing after each addition. Addition was stopped when 10 volumes have been added, as a clear solution was obtained. (S)-Nicotine (1 molar equivalent) is then added to the vial and the vial is shaken at room temperature overnight. The resulting mixture is a clear solution; no solid is isolated.

An experiment is conducted to evaluate the preparation of a 3,5-dihydroxybenzoic acid salt via crystallization from water. 3,5-Dihydroxybenzoic acid (~50 mg) is dispensed into a vial and water is added in aliquots, with 10 minutes of stirring at 80° C. after each addition. Addition was stopped when 3 volumes have been added, as a clear solution was obtained. (S)-Nicotine (1 molar equivalent, 52.6 mg) is then added to the vial and the vial is left to stand at room temperature overnight. After 24 hours, the mixture is still a clear solution and is placed at 5° C.; however, no solid is observed even after evaporation of the liquid.

An experiment is conducted to evaluate the preparation of a 3,5-dihydroxybenzoic acid salt via crystallization from ethanol. 3,5-Dihydroxybenzoic acid (~50 mg) is dispensed into a vial and ethanol is added in aliquots, with 10 minutes of stirring at 70° C. after each addition. Addition is stopped when 3 volumes have been added, as a clear solution was obtained. (S)-Nicotine (1 molar equivalent, 52.6 mg) is then added to the vial and the vial is left to stand at room temperature overnight. After 24 hours, the mixture was still a clear solution and is placed at 5° C.; however, no solid is observed even after evaporation of the liquid.

An experiment is conducted to evaluate the preparation of a 3,5-dihydroxybenzoic acid salt via crystallization from acetone. 3,5-Dihydroxybenzoic acid (~50 mg) is dispensed into a vial and acetone is added in aliquots, with 10 minutes of stirring at 50° C. after each addition. Addition is stopped when 10 volumes have been added, as a clear solution was obtained. (S)-Nicotine (1 molar equivalent, 52.6 mg) is then added to the vial and the vial is left to stand at room temperature overnight. A solid formed in the vial at room temperature following evaporation; however, attempts to characterize the solid by XPRD failed, as the solid turned to a gum. This preparation from acetone is repeated to explore maturation as a method to induce crystallization by mixing 50 mg 3,5-dihydroxybenzoic acid, 10 volumes of acetone, and 1 equivalent nicotine in a vial. The resulting mixture is cycled between room temperature and 50° C. at 8 hour intervals for a period of 2 weeks. A solid is obtained and analyzed by XPRD (indicating a new form) and $^1$H NMR (indicating a 1:1 salt). This material is further analyzed, as the crystals obtained allowed an SCXRD structure to be collected (indicating that the material is an anhydrous salt). The crystal structure is provided at FIG. 13.

On a larger scale, 3,5-dihydroxybenzoic acid (5.66 g) is dissolved in THF (56 mL) at 50° C. (S)-Nicotine (5.9 mL, 1 eq.) is added, followed by seeds of previously prepared nicotine 3,5-dihydroxybenzoate (about 1 mg). After cooling to 25° C. and stirring for about 16 h, the solid is isolated by filtration, washed with heptane (2×2 mL) and dried under vacuum at room temperature for about 16 h to give 7.55 g (65% yield) of white solid. The dihydrate form (nicotine 3,5-dhydroxybenzoate dihydrate) is prepared by placing anhydrous nicotine 3,5-dihydroxybenzoate (100 mg) into an open glass vial and exposing the nicotine 3,5-dihydroxybenzoate to an atmosphere of 96% RH at 25° C. for 16 h. The sample is removed from the vial and characterized by XRPD to confirm that the dihydrated form has been obtained.

The change in form of the anhydrous 3,5-dihydroxybenzoate salt upon exposure to varying humidity levels is indicative of an ability for this salt to exist in one or more hydrated forms. A GVS experiment appeared to show conversion to mono- and di-hydrated forms as well as suggesting the existence of another anhydrous form (with GVS water uptake 0-90% RH of 10% for the anhydrous form). While VH-XRPD experiments confirmed the existence of the dihydrate (exhibiting the same XRPD diffractogram as material resulting from storage of Form 1 at 25° C./96% RH), it was not possible to observe the putative monohydrate and alternative anhydrous form. The dihydrate was subsequently prepared by exposure of the anhydrous form to humidity (converted during storage at 40° C. and 75% relative humidity and at 25° C. and 96% relative humidity). Thermal analysis of this (converted) form show that it can convert back to the known anhydrate upon heating. No events thought to represent phase transitions were observed in the DSC thermogram for any of the salts, the only events being apparent melts. Specifically, the anhydrous form exhibited a melt onset at 138° C. and the dihydrate form exhibited endotherms from 50-100° C. and a melt onset at 137° C.

The anhydrous form is further analyzed by PLM (indicating irregular particles typically <10 µm), and both the anhydrous and dihydrate forms are analyzed by $^1$H NMR (indicating a 1:1 stoichiometry for both forms). A single crystal x-ray diffraction study is performed on the anhydrous nicotine 3,5-dihydroxybenzoate and the structure solved as shown in the ellipsoid plot of FIG. 13 (this is the form made during the small-scale screening study, which is a different form than that obtained during the larger-scale production). A plot showing hydrogen bonding in the asymmetric unit of anhydrous nicotine 3,5-dihydroxybenzoate is provided in FIG. 14A and a plot showing crystal packing for this salt is provided in FIG. 14B.

Figure 9:
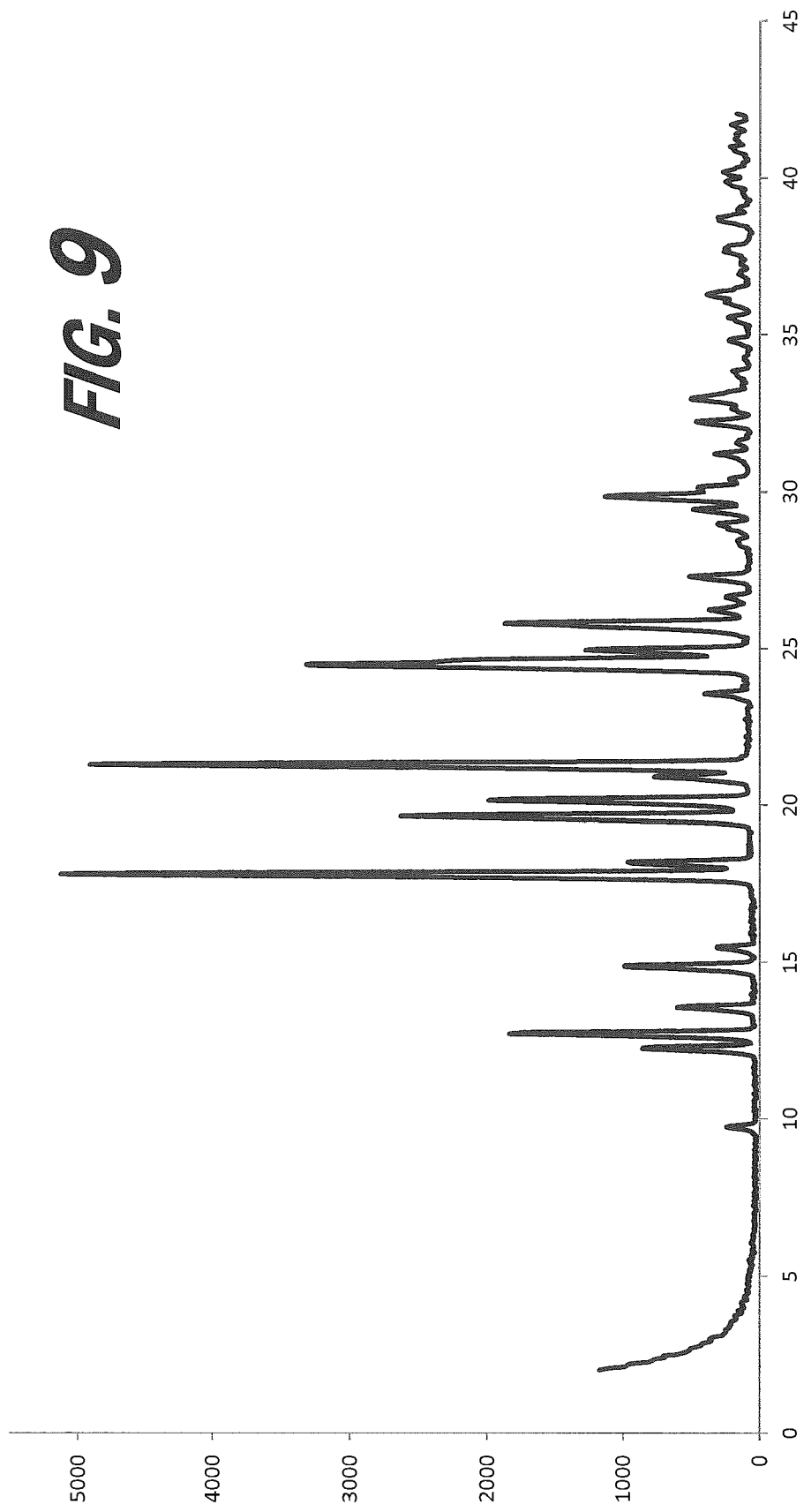
FIG. 9 is an x-ray powder diffraction pattern of anhydrous nicotine 3,5-dihydroxybenzoate, showing the experimental pattern and the pattern calculated from the single crystal x-ray structure.

Both solids (the anhydrous form and the dihydrate form) are analyzed by XRPD, the patterns of which are shown in FIGS. 9 and 11, respectively. Representative peak listings for the XRPD of anhydrous nicotine 3,5-dihydroxybenzoate are provided in Table 9 and representative peak listings for the XRPD of nicotine 3,5-dhydroxybenzoate dihydrate are provided in Table 10.

TABLE 9

XRPD peak listings for anhydrous nicotine 3,5-dihydroxybenzoate

| Angle (2-Theta°) | Intensity (Count) | Intensity (%) |
|---|---|---|
| 9.8 | 238 | 4.6 |
| 12.3 | 850 | 16.6 |
| 12.7 | 1831 | 35.7 |
| 13.6 | 588 | 11.5 |
| 14.9 | 988 | 19.3 |
| 15.5 | 303 | 5.9 |
| 17.8 | 5125 | 100.0 |
| 18.2 | 962 | 18.8 |
| 19.7 | 2631 | 51.3 |
| 20.2 | 1983 | 38.7 |
| 20.9 | 758 | 14.8 |
| 21.3 | 4907 | 95.7 |

TABLE 9-continued

XRPD peak listings for anhydrous nicotine 3,5-dihydroxybenzoate

| Angle (2-Theta°) | Intensity (Count) | Intensity (%) |
|---|---|---|
| 23.6 | 394 | 7.7 |
| 24.5 | 3311 | 64.6 |
| 24.9 | 1274 | 24.9 |
| 25.8 | 1870 | 36.5 |
| 26.2 | 362 | 7.1 |
| 26.6 | 244 | 4.8 |
| 27.3 | 503 | 9.8 |
| 28.4 | 159 | 3.1 |
| 29.0 | 298 | 5.8 |
| 29.4 | 477 | 9.3 |
| 29.8 | 1136 | 22.2 |
| 30.1 | 441 | 8.6 |
| 30.4 | 219 | 4.3 |
| 31.2 | 323 | 6.3 |
| 31.5 | 166 | 3.2 |
| 32.2 | 452 | 8.8 |
| 32.6 | 202 | 3.9 |
| 32.9 | 489 | 9.5 |
| 33.8 | 194 | 3.8 |
| 34.8 | 218 | 4.3 |
| 35.5 | 227 | 4.4 |
| 36.0 | 253 | 4.9 |
| 36.3 | 378 | 7.4 |
| 37.0 | 135 | 2.6 |
| 37.6 | 261 | 5.1 |
| 38.7 | 300 | 5.9 |
| 39.9 | 250 | 4.9 |
| 40.2 | 266 | 5.2 |

TABLE 10

XRPD peak listings for nicotine 3,5-dihydroxybenzoate dihydrate

| Angle (2-Theta°) | Intensity (Count) | Intensity (%) |
|---|---|---|
| 10.7 | 3131 | 92.9 |
| 12.5 | 884 | 26.2 |
| 12.7 | 274 | 8.1 |
| 13.4 | 1575 | 46.7 |
| 15.0 | 2036 | 60.4 |
| 16.5 | 203 | 6.0 |
| 17.2 | 3518 | 104.3 |
| 17.3 | 2575 | 76.4 |
| 19.0 | 2608 | 77.3 |
| 21.4 | 3372 | 100.0 |
| 21.6 | 1152 | 34.2 |
| 22.2 | 2475 | 73.4 |
| 22.6 | 1210 | 35.9 |
| 22.9 | 1392 | 41.3 |
| 24.3 | 1835 | 54.4 |
| 25.1 | 2470 | 73.3 |
| 25.5 | 3201 | 94.9 |
| 25.8 | 618 | 18.3 |
| 26.2 | 278 | 8.2 |
| 26.5 | 442 | 13.1 |
| 26.8 | 542 | 16.1 |
| 27.1 | 357 | 10.6 |
| 27.8 | 195 | 5.8 |
| 29.2 | 539 | 16.0 |
| 29.4 | 629 | 18.7 |
| 29.7 | 1144 | 33.9 |
| 30.2 | 331 | 9.8 |
| 31.4 | 159 | 4.7 |
| 31.9 | 265 | 7.9 |
| 32.2 | 125 | 3.7 |
| 32.6 | 180 | 5.3 |
| 33.2 | 338 | 10.0 |
| 33.9 | 195 | 5.8 |
| 34.4 | 260 | 7.7 |
| 34.9 | 379 | 11.2 |
| 35.3 | 148 | 4.4 |

TABLE 10-continued

XRPD peak listings for nicotine 3,5-dihydroxybenzoate dihydrate

| Angle (2-Theta°) | Intensity (Count) | Intensity (%) |
|---|---|---|
| 35.7 | 265 | 7.9 |
| 36.1 | 138 | 4.1 |
| 36.4 | 169 | 5.0 |
| 37.4 | 158 | 4.7 |
| 37.7 | 275 | 8.2 |
| 38.1 | 163 | 4.8 |
| 38.5 | 351 | 10.4 |
| 38.9 | 131 | 3.9 |
| 40.4 | 209 | 6.2 |
| 40.9 | 315 | 9.3 |
| 41.5 | 170 | 5.0 |
| 42.0 | 451 | 13.4 |

Figure 10:
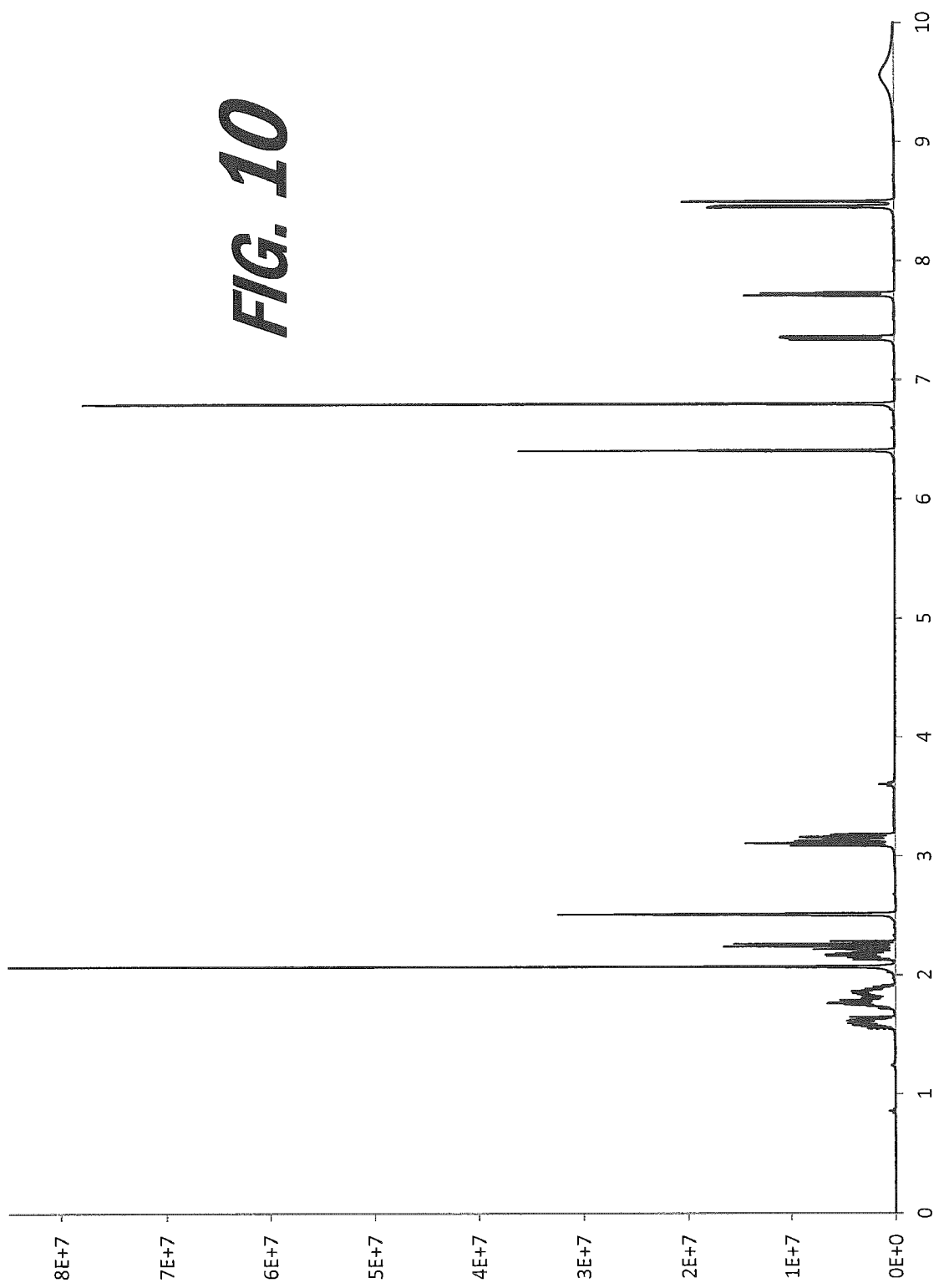
FIG. 10 is a $^1$H NMR spectrum of anhydrous nicotine 3,5-dihydroxybenzoate.
Figure 12:
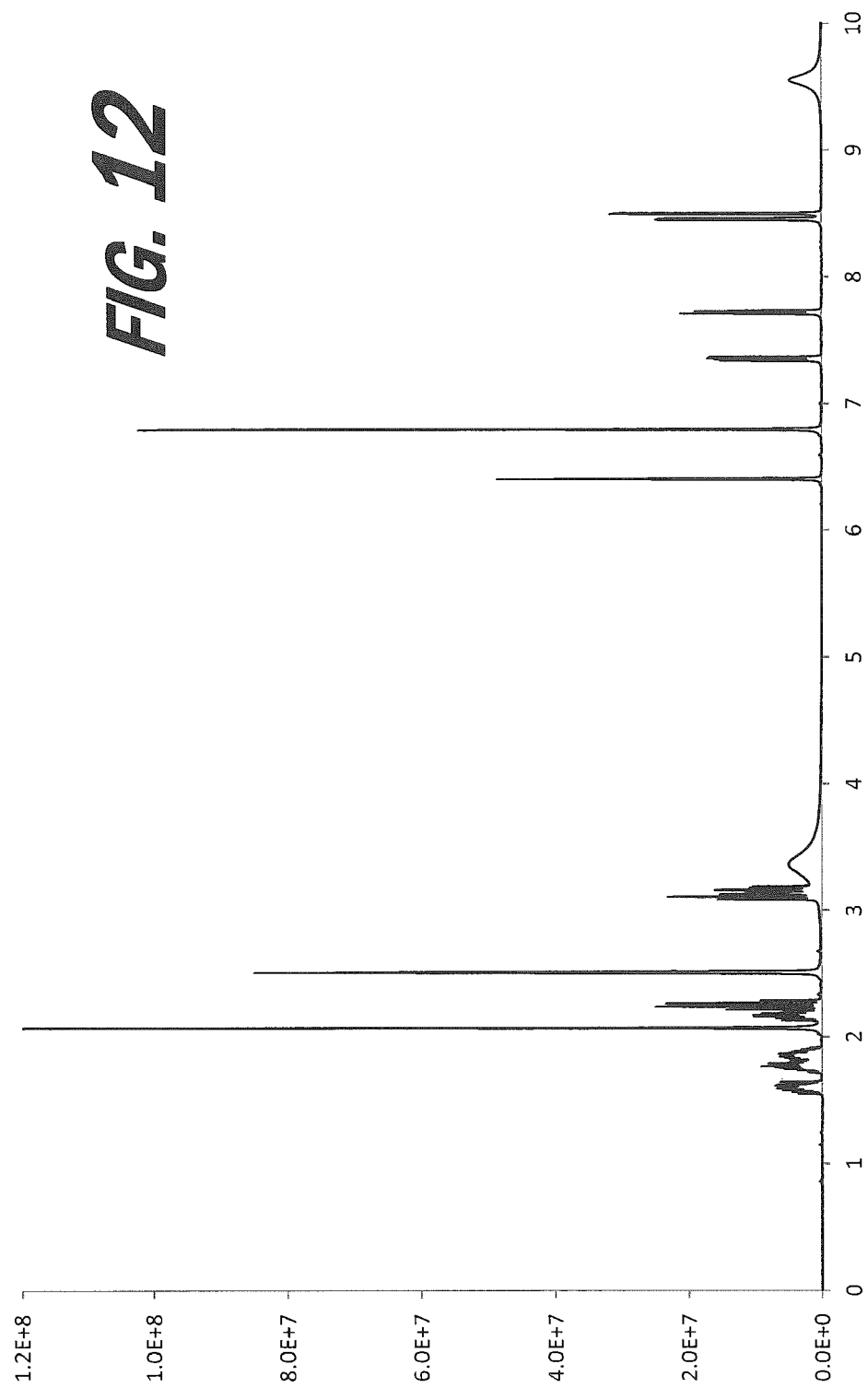
FIG. 12 is a $^1$H NMR spectrum of nicotine 3,5-dihydroxybenzoate dihydrate.

The anhydrous form and the dihydrate form of nicotine 3,5-dihydroxybenzoate are further analyzed by various techniques, including $^1$H NMR, as shown in FIGS. 10 and 12, respectively. Note that the broad resonance at about 9.6 ppm in both of these NMR spectra is believed to arise from the COOH acidic proton and reflects its environment in the DMSO solution in which it was analyzed, which is not necessarily the same as in the solid. In the solid state, the proton is expected to be on the nitrogen atom of the nicotine, as proton transfer will have occurred, but in the DMSO solution, the salt is understood to be in equilibrium with the dissociated species.

Crystallographic parameters for the isolated form are provided below in Table 11. The structure solution was obtained by direct methods, full-matrix least-squares refinement on $F^2$ with weighting $w^{-1}=1/[\sigma^2 (F_o^2)+(0.0659P)^2+0.2704P]$, where $P=(F_o^2+2F_c^2)/3$, anisotropic displacement parameters. Semi-empirical absorption correction using direct methods, implemented in SHELXTL. Absolute structure parameter=0.02(7). Final $wR^2=0.0992$ for all data, conventional $R_1=0.0383$ on F values of 6431 reflections with $F_o>4s(F_o)$, S=1.050 for all data. Final difference map between +0.186 and −0.224 e Å$^{-3}$.

TABLE 11

Crystallographic parameters for nicotine 3,5-dihydroxybenzoate

| | |
|---|---|
| Molecular formula | $C_{17}H_{20}N_2O_4$ |
| Molecular weight | 316.35 |
| Crystallization solvent | Tetrahydrofuran |
| Crystallization method | Maturation |
| Crystal system | Monoclinic |
| Space group | P2$_1$   a   7.84902(9) Å   α   90° |
| | b   13.74501(18) Å   β   96.0438(11)° |
| | c   15.03350(17) Å   γ   90° |
| V | 1612.87(3) Å$^3$ |
| Z | 4 |
| D$_c$ | 1.303 Mg/m$^{-3}$ |
| μ | 0.770 mm$^{-1}$ |
| Source, λ | Cu—K(alpha), 1.54178 Å |
| F(000) | 672 |
| T | 100(2) K |
| Crystal | colorless prism, 0.200 × 0.200 × 0.160 mm |
| Abs. Struct. Para. | 0.02(7) |

Example 7

Salts of Nicotine with 2,3-dihydroxybenzoic Acid

A screening experiment is first conducted to evaluate the formation of a nicotine salt with 2,3-dihydroxybenzoic acid by crystallization from neat nicotine. 2,3-Dihydroxybenzoic acid (~25 mg) is combined with (S)-nicotine (100 μL) and the mixture is shaken at room temperature overnight. The resulting solid material is sampled and characterized by XPRD (showing a new form). The study is repeated on a 100 mg scale, with the solids produced being isolated by filtration, washed with heptane (2×1 mL) and characterized by XPRD and $^1$H NMR (which indicated a 1:1 stoichiometry).

An experiment is conducted to evaluate the preparation of a 2,3-dihydroxybenzoic acid salt via crystallization from THF. 2,3-Dihydroxybenzoic acid (~40 mg) is dispensed into a vial and THF is added in aliquots, with brief vortexing after each addition. Addition is stopped when 10 volumes have been added, as a clear solution is obtained. (S)-Nicotine (1 molar equivalent) is then added to the vial and the vial is shaken at room temperature overnight. The resulting mixture is a clear solution; no solid is observed.

An experiment is conducted to evaluate the preparation of a 2,3-dihydroxybenzoic acid salt via crystallization from water. 2,3-Dihydroxybenzoic acid (~50 mg) is dispensed into a vial and water is added in aliquots, with 10 minutes of stirring at 80° C. after each addition. Addition is stopped when 20 volumes have been added, as a clear solution is obtained. (S)-Nicotine (1 molar equivalent, 52.6 mg) is then added to the vial and the vial was left to stand at room temperature overnight. After 24 hours, the mixture is still a clear solution and is placed at 5° C.; however, no solid is observed even after evaporation of the liquid.

An experiment is conducted to evaluate the preparation of a 2,3-dihydroxybenzoic acid salt via crystallization from ethanol. 2,3-Dihydroxybenzoic acid (~50 mg) is dispensed into a vial and ethanol is added in aliquots, with 10 minutes of stirring at 70° C. after each addition. Addition is stopped when 3 volumes have been added, as a clear solution is obtained. (S)-Nicotine (1 molar equivalent, 52.6 mg) is then added to the vial and the vial was left to stand at room temperature overnight. After 24 hours, the mixture is still a clear solution and is placed at 5° C.; however, no solid is observed, even after evaporation of the liquid.

An experiment is conducted to evaluate the preparation of a 2,3-dihydroxybenzoic acid salt via crystallization from acetone. 2,3-Dihydroxybenzoic acid (~50 mg) is dispensed into a vial and acetone is added in aliquots, with 10 minutes of stirring at 50° C. after each addition. Addition is stopped when 10 volumes have been added, as a clear solution is obtained. (S)-Nicotine (1 molar equivalent, 52.6 mg) is then added to the vial and the vial is left to stand at room temperature overnight. No solid is observed and the solvent is allowed to evaporate; however, no solid is observed even after evaporation.

To prepare nicotine 2,3-dihydroxybenzoate on a larger scale, 2,3-dihydroxybenzoic acid (4.47 g) is dissolved in THF (8.9 mL) at room temperature. Although unsuccessful on a smaller scale (as noted above), (S)-nicotine (4.7 mL) is added, causing instant precipitation of a crystalline solid. The slurry is diluted with further THF (3 mL) and stirred at room temperature for 1 hour. The solid present is isolated by filtration, washed with heptane (2×3 mL), and dried under vacuum at room temperature for about 60 hours to give an off-white solid (7.90 g, 86% yield). Although not intended to be limiting, it is believed that the failed attempt at salt crystallization from THF on a small scale (with success of salt preparation from THF on a larger scale) is due to dilution effects. The small scale crystallization attempt was performed using an excess of THF and it is believed that, under such conditions, the solid remained solubilized and no precipitate was observed due to the presence of this excess of THF. However, with less THF relative to the 2,3-dihydroxybenzoid acid in the large scale method, a solid was formed.

The solid is analyzed by XRPD, the pattern of which is shown in FIG. 12. Representative peak listings for the XPRD of nicotine 2,3-dihydroxybenzoate are provided in Table 12.

TABLE 12

XRPD peak listings for nicotine 2,3-dihydroxybenzoate

| Angle (2-Theta°) | Intensity (Count) | Intensity (%) |
| --- | --- | --- |
| 9.7 | 87 | 2.4 |
| 12.4 | 2824 | 77.9 |
| 12.5 | 3002 | 82.8 |
| 13.1 | 172 | 4.7 |
| 14.7 | 338 | 9.3 |
| 15.2 | 1117 | 30.8 |
| 15.5 | 475 | 13.1 |
| 18.3 | 3625 | 100.0 |
| 19.4 | 297 | 8.2 |
| 19.7 | 1542 | 42.5 |
| 19.9 | 209 | 5.8 |
| 20.3 | 2486 | 68.6 |
| 20.9 | 3179 | 87.7 |
| 23.7 | 268 | 7.4 |
| 23.9 | 360 | 9.9 |
| 24.9 | 3298 | 91.0 |
| 25.2 | 2149 | 59.3 |
| 26.2 | 820 | 22.6 |
| 26.5 | 1350 | 37.2 |
| 26.7 | 148 | 4.1 |
| 27.4 | 447 | 12.3 |
| 27.8 | 118 | 3.3 |
| 28.4 | 271 | 7.5 |
| 28.9 | 297 | 8.2 |
| 29.3 | 258 | 7.1 |
| 29.5 | 339 | 9.4 |
| 29.6 | 410 | 11.3 |
| 30.4 | 1392 | 38.4 |
| 31.2 | 179 | 4.9 |
| 31.8 | 321 | 8.9 |
| 32.0 | 314 | 8.7 |
| 32.7 | 217 | 6.0 |
| 33.3 | 347 | 9.6 |
| 33.6 | 234 | 6.5 |
| 34.4 | 197 | 5.4 |
| 35.6 | 332 | 9.2 |
| 36.6 | 384 | 10.6 |
| 37.0 | 396 | 10.9 |
| 37.5 | 182 | 5.0 |
| 37.7 | 161 | 4.4 |
| 38.1 | 145 | 4.0 |
| 38.6 | 156 | 4.3 |
| 39.0 | 230 | 6.3 |
| 39.8 | 290 | 8.0 |
| 40.6 | 181 | 5.0 |
| 41.1 | 273 | 7.5 |

The nicotine 2,3-dihydroxybenzoate solid is further analyzed by various techniques, including $^1$H NMR (indicating that the salt has a 1:1 stoichiometry); PLM (indicating irregular plates up to about 150 μm); TGA (indicating a 2-stage mass loss from 150° C.); DSC (indicating a melt onset at 157° C.); and GVS (indicating water uptake of 0.12% from 0-90% RH).

Example 8

Salts of nicotine with 1-hydroxy-2-naphthoic acid

A screening experiment is first conducted to evaluate the formation of a nicotine salt with 2,3-dihydroxybenzoic acid by crystallization from neat nicotine. 1-Hydroxy-2-naphthoic acid (~25 mg) is combined with (S)-nicotine (100 μL) and the mixture is shaken at room temperature overnight. The resulting solid material is sampled and characterized by XPRD (showing a new form). The study is repeated on a 100 mg scale, with the solids produced being isolated by filtration, washed with heptane (2×1 mL) and characterized by XPRD and $^1$H NMR (which indicated a 1:1 stoichiometry).

An experiment is conducted to evaluate the preparation of a 1-hydroxy-2-naphthoic acid salt via crystallization from THF. 1-Hydroxy-2-naphthoic acid (~40 mg) is dispensed into a vial and THF is added in aliquots, with brief vortexing after each addition. Addition is stopped when 10 volumes have been added, as a clear solution is obtained. (S)-Nicotine (1 molar equivalent) is then added to the vial and the vial is shaken at room temperature overnight. The resulting mixture is a clear solution and a solid salt is obtained after evaporation (providing the same XPRD pattern as obtained by preparation in neat nicotine).

An experiment is conducted to evaluate the preparation of a 1-hydroxy-2-naphthoic acid salt via crystallization from water. 1-Hydroxy-2-naphthoic acid (~50 mg) is dispensed into a vial and water is added in aliquots, with 10 minutes of stirring at 80° C. after each addition. A solution of the acid in water was never obtained (after 20 volumes of water were added). (S)-Nicotine (1 mol. eq.) was added and the slurry was stirred at 80° C. overnight. No change in XRPD pattern as compared with the acid was observed, indicating no formation of a salt form.

An experiment is conducted to evaluate the preparation of a 1-hydroxy-2-naphthoic acid salt via crystallization from ethanol. 1-hydroxy-2-naphthoic acid (~50 mg) is dispensed into a vial and ethanol is added in aliquots, with 10 minutes of stirring at 70° C. after each addition. Addition is stopped when 10 volumes have been added, as a clear solution is obtained. (S)-Nicotine (1 molar equivalent, 52.6 mg) is then added to the vial and the vial is left to stand at room temperature overnight. A solid is observed in the vial at room temperature; however, attempts to characterize the solid by XPRD failed, as the solid turned to a gum. This preparation from ethanol was repeated to explore maturation as a method to induce crystallization by mixing 50 mg 1-hydroxy-2-naphthoic acid, 10 volumes of ethanol, and 1 equivalent nicotine in a vial. The resulting mixture was cycled between room temperature and 50° C. at 8 hour intervals for a period of 2 weeks. Only a clear solution was obtained.

An experiment is conducted to evaluate the preparation of a 1-hydroxy-2-naphthoic acid salt via crystallization from acetone. 1-Hydroxy-2-naphthoic acid (~50 mg) is dispensed into a vial and acetone is added in aliquots, with 10 minutes of stirring at 50° C. after each addition. Addition is stopped when 10 volumes have been added, as a clear solution is obtained. (S)-Nicotine (1 molar equivalent, 52.6 mg) is then added to the vial and the vial is left to stand at room temperature overnight. No solid is observed and the solvent was allowed to evaporate; however, no solid was isolated even after evaporation.

To prepare nicotine 1-hydroxy-2-naphthoate on a larger scale, 1-hydroxy-2-naphthoic acid (5.02 g) is dissolved in THF (10.0 mL) at room temperature. (S)-Nicotine (4.3 mL) is added, followed by seeds of the desired salt form (~1 mg), causing instant precipitation of a crystalline solid. The slurry is stirred at room temperature for 30 minutes and the solid present is then isolated by filtration, washed with heptane (2×2 mL), and dried under vacuum at room temperature for about 16 hours to give a buff-colored solid (6.49 g, 69% yield).

The solid is analyzed by XRPD, the pattern of which is shown in FIG. 17. Representative peak listings for the XPRD of nicotine 1-hydroxy-2-naphthoate are provided in Table 13.

TABLE 13

XRPD peak listings for nicotine 1-hydroxy-2-naphthoate

| Angle (2-Theta°) | Intensity (Count) | Intensity (%) |
|---|---|---|
| 9.0 | 604 | 11.0 |
| 11.2 | 1708 | 31.3 |
| 14.4 | 1937 | 35.3 |
| 15.6 | 5486 | 100.0 |
| 16.1 | 2911 | 53.1 |
| 17.0 | 1309 | 23.9 |
| 18.0 | 262 | 4.8 |
| 18.5 | 842 | 15.3 |
| 19.2 | 1469 | 26.8 |
| 20.5 | 6843 | 124.7 |
| 22.2 | 1125 | 20.5 |
| 22.5 | 5337 | 97.3 |
| 22.9 | 339 | 6.2 |
| 23.8 | 211 | 3.8 |
| 25.4 | 1251 | 22.8 |
| 25.7 | 1637 | 29.8 |
| 26.3 | 606 | 11.0 |
| 27.1 | 3128 | 57.0 |
| 27.8 | 433 | 7.9 |
| 28.4 | 274 | 5.0 |
| 28.9 | 495 | 9.0 |
| 29.9 | 633 | 11.5 |
| 30.2 | 375 | 6.8 |
| 30.6 | 435 | 7.9 |
| 31.0 | 98 | 1.8 |
| 31.3 | 218 | 4.0 |
| 32.3 | 185 | 3.4 |
| 32.6 | 407 | 7.4 |
| 32.7 | 297 | 5.4 |
| 33.0 | 165 | 3.0 |
| 34.0 | 416 | 7.6 |
| 34.9 | 493 | 9.0 |
| 36.2 | 547 | 10.0 |
| 36.5 | 300 | 5.5 |
| 37.1 | 90 | 1.6 |
| 37.4 | 307 | 5.6 |
| 37.8 | 215 | 3.9 |
| 38.5 | 693 | 12.6 |
| 38.8 | 437 | 8.0 |

The nicotine 1-hydroxy-2-naphthoate solid is further analyzed by various techniques, including $^1$H NMR (indicating that the salt has a 1:1 stoichiometry); PLM (indicating irregular particles up to about 100 μm); TGA (indicating a 2-stage mass loss from 130° C.); DSC (indicating a melt onset at 111° C.); and GVS (indicating water uptake of 0.16% from 0-90% RH).

Example 9

Pyrolysis Studies

Several salts of nicotine, including nicotine mucate, nicotine 4-acetamidobenzoate, nicotine gentisate, nicotine 3-hydroxybenzoate, nicotine L-malate, nicotine 3,5-dihydroxybenzoate, nicotine 2,3-dihydroxybenzoate, and nicotine 1-hydroxy-2-naphthoate are pyrolyzed at 650° C. in helium to evaluate pyrolysis products generated from each salt upon heating. In all samples, high yields of nicotine are generated, indicating that nicotine is liberated from the salt at this elevated temperature.

The instrumentation used in the experiment was a filament pyrolyzer in line with a GC/MS instrument. During the pyrolysis process, compounds typically released (in addition to nicotine) were the decarboxylated molecules corresponding to the analyzed acid, free carbon dioxide, and water. For most salts, no decomposition of nicotine is observed.

Example 10

Salt-Containing Lozenges

Several salts of nicotine, including nicotine mucate, nicotine salicylate, nicotine 4-acetamidobenzoate, nicotine gentisate, nicotine 3-hydroxybenzoate, nicotine L-malate, nicotine 3,5-dihydroxybenzoate, nicotine 2,3-dihydroxybenzoate, and nicotine 1-hydroxy-2-naphthoate are incorporated into smokeless tobacco products in the form of lozenges. The lozenges can generally comprise components disclosed in U.S. Pat. App. Pub. No. 2013/0078307 to Holton, Jr., which is incorporated herein by reference. For example, representative lozenges can comprise isomalt, maltitol syrup, flavorant(s), water, and a nicotinic compound (with one or more of the nicotine salts, co-crystals, or salt co-crystals disclosed herein used in place of the nicotinic compounds disclosed in the reference). The amount of nicotine salt, co-crystal, or salt co-crystal included in each lozenge is that amount sufficient to provide 2 mg nicotine (adjusted based on the weight of the particular coformer). The sensory (e.g., taste and mouthfeel) characteristics and/or the stability of lozenges can, in some embodiments, be affected by the selection of nicotine salt, co-crystal, or salt co-crystal.

It is noted that, in some embodiments, one or more components are commonly introduced in nicotine-containing lozenges to preclude volatilization of the nicotine therein (e.g., including, but not limited to, citric acid). The nicotine salts, co-crystals, and salt co-crystals disclosed herein may, in some embodiments, be incorporated into a lozenge without such a component, as providing nicotine in this form may, itself, prevent volatilization of the nicotine.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A salt of nicotine and 3,5-dihydroxybenzoic acid, wherein the salt is in an anhydrous form characterized by an X-ray powder diffraction pattern having peaks at one or more of the following 2-theta diffraction angles: 12.7, 17.8, 19.7, 20.2, 21.3, 24.5, 24.9, 25.8, and 29.8.

2. The salt of claim 1, wherein at least about 50% of the salt is in crystalline form.

3. The salt of claim 1, wherein at least about 70% of the salt is in crystalline form.

4. The salt of claim 1, wherein at least about 80% of the salt is in crystalline form.

5. The salt of claim 1, wherein at least about 90% of the salt is in crystalline form.

6. The salt of claim 1, wherein the salt exhibits a discrete melting point with an onset of about 138° C.

7. The salt of claim 1, characterized by an X-ray powder diffraction pattern having peaks at two or more of the following 2-theta diffraction angles: 12.7, 17.8, 19.7, 20.2, 21.3, 24.5, 24.9, 25.8, and 29.8.

8. The salt of claim 1, characterized by an X-ray powder diffraction pattern having peaks at three or more of the following 2-theta diffraction angles: 12.7, 17.8, 19.7, 20.2, 21.3, 24.5, 24.9, 25.8, and 29.8.

9. The salt of claim 1, characterized by an X-ray powder diffraction pattern having peaks at four or more of the following 2-theta diffraction angles: 12.7, 17.8, 19.7, 20.2, 21.3, 24.5, 24.9, 25.8, and 29.8.

10. The salt of claim 1, characterized by an X-ray powder diffraction pattern having peaks at five or more of the following 2-theta diffraction angles: 12.7, 17.8, 19.7, 20.2, 21.3, 24.5, 24.9, 25.8, and 29.8.

11. The salt of claim 1, characterized by an X-ray powder diffraction pattern having peaks at six or more of the following 2-theta diffraction angles: 12.7, 17.8, 19.7, 20.2, 21.3, 24.5, 24.9, 25.8, and 29.8.

12. The salt of claim 1, characterized by an X-ray powder diffraction pattern having peaks at seven or more of the following 2-theta diffraction angles: 12.7, 17.8, 19.7, 20.2, 21.3, 24.5, 24.9, 25.8, and 29.8.

13. The salt of claim 1, characterized by an X-ray powder diffraction pattern having peaks at eight or more of the following 2-theta diffraction angles: 12.7, 17.8, 19.7, 20.2, 21.3, 24.5, 24.9, 25.8, and 29.8.

14. The salt of claim 1, characterized by an X-ray powder diffraction pattern having peaks at all of the following 2-theta diffraction angles: 12.7, 17.8, 19.7, 20.2, 21.3, 24.5, 24.9, 25.8, and 29.8.

* * * * *